US011806515B2

(12) United States Patent
Diaz et al.

(10) Patent No.: US 11,806,515 B2
(45) Date of Patent: Nov. 7, 2023

(54) SYSTEM AND METHOD FOR COLLECTING INJECTION INFORMATION

(71) Applicant: Credence Medsystems, Inc., Menlo Park, CA (US)

(72) Inventors: Stephen H. Diaz, Palo Alto, CA (US); Alan E. Shluzas, San Carlos, CA (US); John F. Shanley, Emerald Hills, CA (US); Jeff Tillack, Foster City, CA (US); John Merhige, Subury, MA (US); Frank Litvack, Los Angeles, CA (US); Dan Thayer, Tustin, CA (US)

(73) Assignee: Credence MedSystems, Inc., Menlo Park, CA (US)

( * ) Notice: Subject to any disclaimer, the term of this patent is extended or adjusted under 35 U.S.C. 154(b) by 164 days.

(21) Appl. No.: 17/169,806

(22) Filed: Feb. 8, 2021

(65) Prior Publication Data

US 2021/0236742 A1  Aug. 5, 2021

Related U.S. Application Data

(63) Continuation of application No. 15/985,354, filed on May 21, 2018, now Pat. No. 10,912,895.
(Continued)

(51) Int. Cl.
*A61M 5/32* (2006.01)
*A61M 5/315* (2006.01)
(Continued)

(52) U.S. Cl.
CPC .......... *A61M 5/3221* (2013.01); *A61M 5/172* (2013.01); *A61M 5/178* (2013.01);
(Continued)

(58) Field of Classification Search
CPC ................ A61M 5/3221; A61M 5/172; A61M 5/31533; A61M 5/3157
See application file for complete search history.

(56) References Cited

U.S. PATENT DOCUMENTS 9,775,957 B2  10/2017  Despa et al.
10,052,441 B2  8/2018  Searle et al.
(Continued)

FOREIGN PATENT DOCUMENTS

WO  WO 2011/117212 A1  9/2011
WO  WO 2014/152704 A1  9/2014
(Continued)

OTHER PUBLICATIONS

PCT International Preliminary Report on Patentability (Chapter I of the Patent Cooperation Treaty) for PCT/US2018/033721, Applicant: Credence MedSystems, Inc., Form PCT/ISA/326 and 373, dated Nov. 28, 2019.
(Continued)

*Primary Examiner* — Bradley J Osinski
(74) *Attorney, Agent, or Firm* — Vista IP Law Group LLP

(57) ABSTRACT

A system for measuring injection of a liquid medicine includes a syringe body having proximal and distal ends, a syringe interior, and a syringe flange at the proximal end thereof. The system also includes a stopper member disposed in the syringe interior. The system further includes a plunger member coupled to the stopper member and configured to be manipulated to insert the stopper member distally in the syringe interior relative to the syringe body. Moreover, the system includes a needle coupled to the syringe body at the distal end thereof. In addition, the system includes a sensor flange removably coupled to a syringe body. The sensor flange includes a sensor to measure an injection characteristic and a processor to analyze the injec-
(Continued)

tion characteristic to determine an occurrence of an injection event.

20 Claims, 32 Drawing Sheets

Related U.S. Application Data

(60) Provisional application No. 62/508,508, filed on May 19, 2017.

(51) Int. Cl.
    *A61M 5/172*     (2006.01)
    *A61M 5/178*     (2006.01)
    *G16H 20/17*     (2018.01)

(52) U.S. Cl.
CPC ...... *A61M 5/3157* (2013.01); *A61M 5/31533* (2013.01); *A61M 5/3202* (2013.01); *A61M 5/3232* (2013.01); *A61M 5/31501* (2013.01); *A61M 2005/3223* (2013.01); *A61M 2205/33* (2013.01); *A61M 2205/332* (2013.01); *A61M 2205/3306* (2013.01); *A61M 2205/3375* (2013.01); *A61M 2205/3569* (2013.01); *A61M 2205/43* (2013.01); *A61M 2205/502* (2013.01); *G16H 20/17* (2018.01)

(56) References Cited

U.S. PATENT DOCUMENTS

| | | | |
|---|---|---|---|
| 10,086,147 | B2 | 10/2018 | Despa et al. |
| 10,258,745 | B2 | 4/2019 | Despa et al. |
| 10,292,641 | B2 | 5/2019 | Bureau et al. |
| 10,568,575 | B2 | 2/2020 | Martin et al. |
| 10,668,226 | B2 | 6/2020 | Searle et al. |
| 10,704,944 | B2 | 6/2020 | Searle et al. |
| 10,912,895 | B2 | 2/2021 | Diaz et al. |
| 2011/0009812 | A1 | 1/2011 | Brown |
| 2015/0174342 | A1 | 6/2015 | Mitrosky et al. |
| 2016/0030673 | A1 | 2/2016 | White et al. |
| 2016/0213856 | A1 | 7/2016 | Despa et al. |
| 2016/0259913 | A1 | 9/2016 | Yu et al. |
| 2017/0136185 | A1 | 5/2017 | Rios et al. |
| 2018/0161513 | A1 | 1/2018 | Richards et al. |
| 2019/0298931 | A1 | 10/2019 | Despa et al. |

FOREIGN PATENT DOCUMENTS

| | | |
|---|---|---|
| WO | WO 2015/136564 A1 | 9/2015 |
| WO | WO 2015/171778 A1 | 11/2015 |
| WO | WO 2016/140853 A1 | 9/2016 |

OTHER PUBLICATIONS

PCT International Search Report for PCT/US2018/033721, Applicant: Credence Medsystems, Inc., Form PCT/ISA/210 and 220, dated Aug. 13, 2018 (7 pages).
PCT Written Opinion of the International Search Authority for PCT/US2018/033721, Applicant: Credence Medsystems, Inc., Form PCT/ISA/237, dated Aug. 13, 2018 (6 pages).
Non-Final Office Action for U.S. Appl. No. 15/985,354 dated Jun. 24, 2020.
Amendment Response to NFOA for U.S. Appl. No. 15/985,354 dated Sep. 10, 2020.
Notice of Allowance for U.S. Appl. No. 15/985,354 dated Oct. 2, 2020.
Foreign OA for CN Patent Appln. No. 201880047354.8 dated Jun. 1, 2021 (with English translation).
Foreign OA for JP Patent Appln. No. 2019-563268 dated Aug. 3, 2021.
Foreign OA for Brazilian Patent Appn. No. BR 11 2019 024399 2 dated Sep. 8, 2021.
Foreign OA Response for Brazilian Patent Appn. No. BR 11 2019 024399 2 dated Dec. 17, 2021.
Foreign Response for CN Patent Appln. No. 201880047354.8 dated Oct. 18, 2021.
Foreign OA for CN Patent Appln. No. 201880047354.8 dated Dec. 24, 2021.
Foreign Response for CN Patent Appln. No. 201880047354.8 dated Mar. 7, 2022.
Foreign NOA for CN Patent Appln. No. 201880047354.8 dated Apr. 20, 2022.
Foreign OA for IN Patent Appln. No. 201947051640 dated Mar. 2, 2022 In English.
Foreign Response for IN Patent Appln. No. 201947051640 dated Aug. 30, 2022 In English.
Foreign Response for JP Patent Appln. No. 2019-563268 dated Nov. 2, 2021.
Foreign OA for JP Patent Appln. No. 2019-563268 dated Nov. 30, 2021.
Foreign NOA for JP Patent Appln. No. 2019-563268 dated Feb. 24, 2023 (with English translation).
Foreign OA for JP Patent Appln. No. 2022 -- 055277 dated Feb. 14, 2023.
Foreign Response for JP Patent Appln. No. 2022 -- 055277 dated May 12, 2023.
Foreign Exam Report for CA Patent Appln. No. 3063538 dated Jun. 30, 2023.
Foreign OA for JP Patent Appln. No. 2022-055277 dated Aug. 1, 2023 (with English translation).

SYSTEM AND METHOD FOR COLLECTING INJECTION INFORMATION

CROSS-REFERENCE TO RELATED APPLICATION(S)

The present application is a continuation of U.S. patent application Ser. No. 15/985,354, filed May 21, 2018 and entitled "SYSTEM AND METHOD FOR COLLECTING INJECTION INFORMATION," which claims priority to U.S. Provisional patent Application Ser. No. 62/508,508, filed on May 19, 2017 entitled "SYSTEM AND METHOD FOR COLLECTING INJECTION INFORMATION". This application includes subject matter similar to the subject matter described in the following co-owned U.S. patent applications: (1) Ser. No. 14/696,342, filed Apr. 24, 2015, entitled "SYSTEM AND METHOD FOR SAFETY SYRINGE"; (2) Ser. No. 14/543,787, filed Nov. 17, 2014, entitled "SYSTEM AND METHOD FOR DRUG DELIVERY WITH A SAFETY SYRINGE"; (3) Ser. No. 14/321,706, filed Jul. 1, 2014, entitled "SAFETY SYRINGE"; and (4) Ser. No. 62/416,102, filed Nov. 1, 2016, entitled "SYSTEM AND METHOD FOR SAFETY SYRINGE"; (5) Ser. No. 62/431,382, filed Dec. 7, 2016, entitled "SYSTEM AND METHOD FOR SAFETY SYRINGE"; (6) Ser. No. 62/480,276, filed Mar. 31, 2017, entitled "SYSTEM AND METHOD FOR SAFETY SYRINGE." The contents of the above-mentioned applications are fully incorporated herein by reference as though set forth in full.

FIELD OF THE INVENTION

The present invention relates generally to injection systems, devices, and processes for facilitating various levels of control over fluid infusion, and more particularly to systems and methods related to safety syringes in healthcare environments. Even more particularly, the present invention relates to injection systems, devices, and processes for managing injection related information.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs.

Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling.

The use of needle injection configurations, on the other hand, carries with it the risk of a sharp needle contacting or stabbing a person or structure that is not desired. For this reason, so called "safety syringes" have been developed. One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety. Other "safety syringes" are described in U.S. patent application Ser. Nos. 14/696,342, 14/543,787, 14/321,706, 62/416,102, 62/431,382, and 62/480,276, the contents of which have been incorporated herein by reference.

Further complicating the syringe marketplace is an increasing demand for pre-filled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface (14). Liquid medicine may reside in the volume, or medicine reservoir, (40) between the distal seal (35) and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body (34) structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the medicine chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross sectional shape may establish a seal against the syringe body), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as the system (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Regardless of the type of injection system, collecting information relating to the delivery of injectables (e.g., medications) can provide many advantages. In embodiments where injectable medications are self-administered by patients, collecting information relating to the delivery of injectables (i.e., "injection information") can facilitate determination of patient compliance. In such embodiments, the injection information may be whether the injection has been delivered. Because patient noncompliance increases the cost of healthcare, determining patient compliance can reduce healthcare costs and improve healthcare results. Even in embodiments where injectable medications are administered by medical professionals, collecting injection information can increase the tracking accuracy for injectable medication delivery, which in turn reduces healthcare costs and improves healthcare results (e.g., by determining whether an injection was properly delivered). Automating the collection of injection information can secure these and many other advantages with minimal or no human intervention.

Automated injection information collection can lead to advancements in various healthcare areas including but not limited to, healthcare informatics, personalized medicine, electronic medical records, and personalize wearable computing devices. The collected injection information can be used to assist patients in management and scheduling of injectable medicine delivery. The collected injection information can also be sent to third party (e.g., healthcare providers, insurers, etc.) to improve management and personalization of medical care.

There is a need for injection systems which address the shortcomings of currently-available configurations. In particular, there is a need for injection system that may automatically collect injection information while utilizing the existing and relatively well-controlled supply chain of conventionally delivered syringes and cartridges. Further, there is a need for injection systems that may communicate with various stakeholders (e.g., patients, healthcare providers, insurers, etc.) based on collected injection information to improve healthcare results and reduce healthcare costs.

SUMMARY

Embodiments are directed to injection systems. In particular, the embodiments are directed to safe injection systems that move the needle into a protected configuration to minimize accidental user injury and contamination with used needles.

In one embodiment, a system for injecting includes a syringe body having proximal and distal ends, a syringe interior, and a syringe flange at the proximal end thereof. The system also includes a stopper member disposed in the syringe interior. The system further includes a plunger member coupled to the stopper member and configured to be manipulated to insert the stopper member distally in the syringe interior relative to the syringe body. Moreover, the system includes a needle coupled to the syringe body at the distal end thereof. In addition, the system includes a sensor flange removably coupled to the syringe body at least partially distal of the syringe flange. The sensor flange includes first sensor and second sensor to measure respective first injection characteristic and second injection characteristic. The sensor flange also includes a processor to analyze the first and second injection characteristics to monitor an injection event.

The preferred embodiment of the sensor flange is to be utilized with syringes which are pre-filled with medicine by the manufacturer. Alternatively, the sensor flange may be used with syringes which are filled by the user prior to giving the injection. In both cases, the sensor flange may come pre-mounted onto the syringe or be mounted to the syringe at the time of the injection. Additionally, the sensor flange electronic components and sensors may be located in or on the plunger rod.

In one or more embodiments, the first sensor is a force sensor and the first injection characteristic is an injection backpressure, and the second sensor is a motion sensor and the second injection characteristic is a plunger member movement. The injection event may be injection into atmosphere. The sensor flange may also include an orientation sensor to measure an orientation, where the processor analyzes the orientation to confirm the injection into atmosphere. The injection event may be obstruction of the needle. The injection event may be a leak from the injection system.

In one or more embodiments, the sensor flange is configured to be manipulated to insert the stopper member distally in the syringe interior relative to the syringe body. The plunger member may include a proximal end pad to be manipulated simultaneously with the sensor flange to insert the stopper member distally in the syringe interior relative to the syringe body.

In one or more embodiments, the sensor flange also includes a mounting sensor to detect when the sensor flange is removably coupled to the syringe body. The mounting sensor may include a mechanical switch.

In one or more embodiments, the first and second sensors are selected from the group consisting of an acoustic sensor, a motion sensor, a proximity sensor, a temperature sensor, a force sensor, an accelerometer sensor, an orientation sensor, and an optical sensor. The motion sensor may measure a position, a velocity, or an acceleration of the plunger member. The motion sensor may be an optical sensor. The optical sensor may be an IR sensor. The plunger member may include an identifier to be read by the optical sensor. The identifier may include data selected from the group consisting of drug name, drug dosage, serial number, and expiration date. The motion sensor may be a laser motion sensor. The acoustic sensor may include an ultrasound transducer.

In one or more embodiments, the temperature sensor may measure a temperature of an injectable substance in the syringe interior. The processor may calculate an approximate time until the injectable substance reaches an injection temperature at least partially based on the measured temperature. The sensor flange may also include an output device to deliver an alarm signal when the measured temperature reaches an injection temperature.

In one or more embodiments, the sensor flange also includes a battery. The sensor flange may also include a memory module. The sensor flange may also include a wireless communication device. The wireless communication device may be a Bluetooth communication device, a WiFi communication device, a WiFi Direct communication device, and/or a cellular communication device.

In one or more embodiments, the sensor flange is configured to receive injection setup data through the wireless communication device. The injection setup data may include data selected from the group consisting of current date and time, first injection date and time, injection frequency, syringe type, viscosity, temperature, warming time, maximum shear force, multiple injection site regimen data, reward program data, and educational/marketing data.

In one or more embodiments, the sensor flange is configured to transmit post-injection data through the wireless communication device to a computing device. The post-injection data includes data selected from the group consisting of injection date and time, injection frequency, plunger force, injection elapsed time, injection error related data, viscosity, temperature, warming time, shear force, residual drug remaining in the syringe, multiple injection site regimen data, reward program data, and educational/marketing data. The injection error may be selected from the group consisting of drug identity error, injection timing error, dosage error, shear force error, de-bubbling error, residual drug remaining in the syringe, and multi-site injection error.

In one or more embodiments, the sensor flange also includes an output device. The output device may be a speaker. The output device may be a light source. The output device may be a display device.

In one or more embodiments, the sensor flange also includes a clock. The sensor flange may also include an output device to deliver an alarm signal. The alarm signal may be delivered at a time for an injection. The alarm signal may be an audible alarm signal. The alarm signal may be a visible alarm signal.

The alarm signal may be delivered until the sensor flange is coupled to the syringe body. The alarm signal may be delivered when the sensor flange detects an injection error. The injection error may be selected from the group consisting of drug identity error, injection timing error, dosage error, shear force error, de-bubbling error, residual drug remaining in the syringe, and multi-site injection error. The alarm signal may be delivered if the sensor flange is not removed from the syringe body in a pre-determined time after injection is complete.

In one or more embodiments, the sensor flange is configured to slide along a longitudinal axis of the syringe body when the sensor flange is removably coupled to the syringe body.

In another embodiment, a method for collecting information related to an injection includes removably coupling a sensor flange to a syringe body of an injection system. The injection system includes the syringe body having proximal and distal ends, a syringe interior, and a syringe flange at the proximal end thereof. The system also includes a stopper member disposed in the syringe interior. The system further includes a plunger member coupled to the stopper member. Moreover, the system includes a needle coupled to the syringe body at the distal end thereof. The method also includes manipulating the plunger member to insert the stopper member distally in the syringe interior relative to the syringe body to perform the injection. The method further includes measuring respective first and second injection characteristics using the sensor flange. Moreover, the method includes analyzing the first and second injection characteristics to monitor an injection event. The sensor flange is removably coupled to the syringe body at least partially distal of the syringe flange.

In one or more embodiments, the sensor flange includes a clock, an output device, a wireless communication device, a memory module, first and second sensors, and a processor. Measuring the first and second injection characteristics using the sensor flange includes the first sensor measuring the first injection characteristic and the second sensor measuring the second injection characteristic. The first sensor may be a force sensor and the first injection characteristic may be an injection backpressure. The second sensor may be a motion sensor and the second injection characteristic may be a plunger member movement. The injection event may be injection into atmosphere, and the method also includes detecting the injection into atmosphere when the injection back pressure is substantially zero while the plunger member movement is non-zero.

In one or more embodiments, the sensor flange also includes an orientation sensor to measure an orientation, and the method also includes the processor analyzing the orientation to confirm the injection into atmosphere. The injection event may be obstruction of the needle, and the method may also include detecting the obstruction of the needle when the injection back pressure increases while the plunger member movement is substantially zero. The injection event may be a leak from the injection system, and the method may also include detecting the leak from the injection system when the injection back pressure decreases while the plunger member movement increases.

In one or more embodiments, the method also includes the clock reaching an injection time, the processor instructing the output device to deliver an alarm signal to indicate the injection time. The alarm signal may be an audible alarm signal. The alarm signal may be a visible alarm signal.

In one or more embodiments, the method also includes the processor instructing the output device to terminate delivery of the alarm signal in response to the sensor flange being removably coupled to the syringe body. The method may also include the processor instructing the output device to terminate delivery of the alarm signal after a first pre-determined time, and to resume delivery of the alarm signal after a second pre-determined time. The method may also include the processor instructing the output device to terminate delivery of the alarm signal and to deliver a message regarding a missed dose after a first pre-determined time.

In one or more embodiments, the method also includes providing power to the wireless communication device, and the wireless communication device attempting to establish a connection with a computing device. The method may also include the wireless communication device establishing a connection with a computing device. The method may also include the sensor flange receiving injection setup data from the computing device through the wireless communication device. The injection setup data may include data selected from the group consisting of current date and time, first injection date and time, injection frequency, syringe type, viscosity, temperature, warming time, maximum shear force, multiple injection site regimen data, reward program data, and educational/marketing data.

In one or more embodiments, the method also includes storing the measured first and second characteristics in the memory module. The method may also include the wireless communication device establishing a connection with a computing device, and the sensor flange sending the measured characteristic to the computing device using the wireless communication device. The method may also include storing post-injection data in the memory module. The post-injection data may include data selected from the group consisting of injection date and time, injection frequency, plunger force, injection elapsed time, injection error related data, viscosity, temperature, warming time, shear force, residual drug remaining in the syringe, multiple injection site regimen data, reward program data, and educational/marketing data. The injection error may be selected from the group consisting of drug identity error, injection timing error, dosage error, shear force error, de-bubbling error, residual drug remaining in the syringe, and multi-site injection error.

In one or more embodiments, the method also includes the wireless communication device establishing a connection with a computing device, and the sensor flange sending the post-injection data to the computing device using the wireless communication device. The sensor flange may also include a mounting sensor, and the method may also include the mounting sensor detecting a coupling status of the sensor flange to the syringe body. The method may also include the sensor flange detects an injection, the clock measuring a pre-determined time after the detected injection, and the processor instructing the output device to deliver an alarm signal when the coupling status indicates that the sensor flange is coupled to the syringe body at the pre-determined time.

In one or more embodiments, the method also includes placing the sensor flange in a low power mode when the coupling status indicates that the sensor flange is not coupled to the syringe body. Placing the sensor flange in the low power mode may include deactivating the output device and the wireless communication device, and intermittently measuring the characteristic to determine the coupling status of the sensor flange to the syringe body.

In one or more embodiments, the method also includes the processor calculating a shear force on an injectable substance in the syringe interior at least partially based on the plunger member movement and the injection backpressure. The method may also include the processor instructing the output device to deliver an alarm signal when the calculated shear force exceeds a pre-determined maximum shear force.

In one or more embodiments, the first sensor is a motion sensor and the first injection characteristic is a speed of the plunger member. The method may also include the processor instructing the output device to deliver a speed alert when the speed of the plunger member is outside of a pre-determined range. The speed alert may indicate that the speed of the plunger member is below or above the pre-determined range.

In one or more embodiments, the injection event is completion of an injection, and the method also includes the processor instructing the output device to deliver a multi-site dosing message. The first injection characteristic may include a sound indicating completion of the injection.

In one or more embodiments, the first and second sensors are selected from the group consisting of an acoustic sensor, a motion sensor, a proximity sensor, a temperature sensor, a force sensor, an accelerometer sensor, an orientation sensor, and an optical sensor. The method may also include the processor generating a force profile. The method may also include the processor determining that the injection is completed when the force profile includes a sudden force increase. The method may also include the processor determining that the injection was successfully given when a measured distance traveled by the plunger rod equals a pre-determined value.

In one or more embodiments, the method also includes the processor calculating an approximate time until the injectable substance reaches an injection temperature at least partially based on a measured temperature. The method may also include the processor instructing the output device to deliver an alarm signal when the measured temperature reaches an injection temperature. The method may also include the processor determining that the injection was successfully given when a measured acceleration of the plunger member drops to substantially zero.

In one or more embodiments, the method also includes the processor instructing the output device to deliver an alarm signal when the sensor flange detects an injection error. The injection error may be selected from the group consisting of drug identity error, injection timing error, dosage error, shear force error, de-bubbling error, residual drug remaining in the syringe, and multi-site injection error.

In one or more embodiments, the method also includes removing the sensor flange from the syringe after completing the injection. The method may also include sliding the sensor flange along a longitudinal axis of the syringe body when the sensor flange is removably coupled to the syringe body until the sensor flange contacts a syringe flange on the syringe body.

In still another embodiment, a system for injecting includes a syringe body having proximal and distal ends, and a syringe interior. The system also includes a stopper member disposed in the syringe interior. The system further includes a smart plunger member coupled to the stopper member and configured to be manipulated to insert the stopper member distally in the syringe interior relative to the syringe body. Moreover, the system includes a needle coupled to the syringe body at the distal end thereof. In addition, the system includes an RFID tag configured to be activated during injection.

The preferred embodiment of the smart plunger member is to be utilized with syringes which are pre-filled with medicine by the manufacturer. Alternatively, the smart plunger member may be used with syringes which are filled by the user giving prior to giving the injection. In both cases, the smart plunger member may come pre-mounted onto the syringe or be mounted to the syringe at the time of the injection.

In one or more embodiments, the RFID tag includes an RFID processor, and a shunt to divert power from the RFID processor to reversibly inactivate the RFID tag. The smart plunger member may include a movable proximal end pad having a cutting member configured to cut the shunt when pressure is applied to the plunger proximal end pad to thereby activate the RFID tag.

In one or more embodiments, the RFID tag includes an RFID processor, and an open circuit to reversibly inactivate the RFID tag. The smart plunger member may include a movable proximal end pad having a conducting member configured to close the open circuit when pressure is applied to the plunger proximal end pad to thereby activate the RFID tag.

In one or more embodiments, the smart plunger member including a proximal end pad, and the RFID tag including a spiral antenna disposed in the proximal end pad. The RFID tag may include an elongate antenna disposed in the plunger member. The RFID tag may include a pair of elongate antennae disposed in the plunger member.

In one or more embodiments, the RFID tag is selected from the group consisting of low frequency, high frequency, and ultrahigh frequency. The RFID tag may include a battery.

In yet another embodiment, a method for collecting information related to an injection includes providing an injection system. The system includes a syringe body having proximal and distal ends, and a syringe interior. The system also includes a stopper member disposed in the syringe interior. The system further includes a smart plunger member coupled to the stopper member, and having a movable proximal end pad. Moreover, the system includes a needle coupled to the syringe body at the distal end thereof. In addition, the system includes an RFID tag. The method also includes manipulating the proximal end pad of the plunger member to insert the stopper member distally in the syringe interior relative to the syringe body to perform the injection. Manipulating the proximal end pad of the smart plunger member to insert the stopper member may move the proximal end pad distally relative to the plunger member, thereby activating the RFID tag.

In one or more embodiments, the RFID tag includes an RFID processor, and a shunt to divert power from the RFID processor to reversibly inactivate the RFID tag. The movable proximal end pad may include a cutting member configured. Moving the proximal end pad distally may cut the shunt with the cutting member thereby activating the RFID tag.

In one or more embodiments, the RFID tag includes an RFID processor, and an open circuit to reversibly inactivate the RFID tag. The movable proximal end pad may include a conducting member. Moving the proximal end pad distally may close the open circuit thereby activating the RFID tag.

In one or more embodiments, the RFID tag includes a spiral antenna disposed in the proximal end pad. The RFID tag may include an elongate antenna disposed in the plunger member. The RFID tag may include a pair of elongate antennae disposed in the plunger member.

In one or more embodiments, the RFID tag is selected from the group consisting of low frequency, high frequency, and ultrahigh frequency. The RFID tag may include a battery.

In one or more embodiments, the method also includes the RFID tag establishing a connection with an RFID reader. The method may also include the RFID tag sending injection data to the RFID reader. The injection data may include data selected from the group consisting of drug name, drug dosage, serial number, and expiration date. The method may also include the RFID tag receiving data from the RFID reader. The method may also include the RFID tag inactivating itself in response to receiving the data from the RFID reader.

In one or more embodiments, the sensor is a mechanical sensor and the injection characteristic is a position, a velocity, or an acceleration of the plunger member. The mechanical sensor may include a roller in contact with an outer surface of the plunger member, and a reader. The method may also include the reader measuring a rotation of the roller. The reader may be an optical sensor or a mechanical sensor. The mechanical sensor may include a contact switch. The plunger member may include a feature. The injection characteristic may be a position of the plunger member. The method further may include the feature actuating the contact switch.

In one or more embodiments, the sensor may is an optical sensor. The injection system may also include light source and a light guiding optical element. The injection characteristic may be a position of the stopper member. The method may also include the light guiding optical element directing light from the light source and reflected light to the optical sensor. The sensor flange may be removably coupled to the syringe body at least partially distal of the syringe flange.

In one or more embodiments, the sensor is a first sensor and the injection characteristic is a first injection characteristic. The sensor flange may also include a second sensor. The method may also include the second sensor measuring a second injection characteristic.

In one or more embodiments, the method also includes manipulating the sensor flange to insert the stopper member distally in the syringe interior relative to the syringe body. The plunger member may include a proximal end pad. The method may also include manipulating the proximal end pad simultaneously with the sensor flange to insert the stopper member distally in the syringe interior relative to the syringe body.

In one or more embodiments, the sensor flange also includes a mounting sensor. The method may also include the mounting sensor detecting when the sensor flange may be removably coupled to the syringe body. The method may further include the sensor flange delivering an alarm once the injection of the dose of the liquid medicine has been completed to prevent the sensor flange from being disposed of prematurely. Moreover, the method may include the sensor flange silencing the alarm once the mounting sensor indicates the finger flange has been removed from the syringe body. The mounting sensor may include a mechanical switch. The sensor flange may also include one or more of the following a battery, a speaker, an indicator light, a clock, a calendar, a non-volatile computer memory, a haptic feedback device, and a display device.

In one or more embodiments, the method also includes the sensor flange comparing a measured force time product to a reference force time product to determine the occurrence of the injection event. The method may also include the sensor flange recording a time and a date of the occurrence of the injection event. The reference force time product may be pre-determined based on a viscosity of the liquid medicine to be injected and a size of the needle.

In one or more embodiments, the sensor flange also includes a display, the method further including the display communicating information to a user administering the injection. The method may also include the display warning the user when the injection may be being performed too quickly or too slowly. The sensor flange may also a speaker, the method further including the speaker generating an audible sound for communication with a user administering the injection. The method may also include the speaker warning the user when the injection may be being performed too quickly or too slowly. The sensor flange may also include a calendar, a clock, and one or more output devices to deliver an audible alarm, a visual alarm, and/or a haptic alarm. The method may also include the sensor flange indicating when it may be time for the injection.

In one or more embodiments, the method also includes the sensor flange communicating with a computer network communication protocol that the injection event has occurred. The method may also include the sensor flange communicating intermittently/asynchronously or constantly.

In one or more embodiments, the sensor flange also includes a calendar and a clock, where the sensor flange stores a date and a time of the occurrence of the injection event in a non-volatile memory as injection event data. The injection event data may also include an Fxt product, an injection performed indicator, a temperature, a speed, a pressure, and an injection in air/injection in patient indicator. The method may also include transmitting the stored injection event data once network communication may be established between the sensor flange and a computer network. The method may also include the sensor flange transmitting injection event data to one or more of a smartphone, a computer, a database, a cloud computing network, a health care professional, a home injection patient, an electronic medical record, a smartphone application, a doctor, a nurse, a caregiver, a medical insurer, a clinical trial, a clinical trial administrator, a pharmaceutical distribution company, and a pharmaceutical manufacturer. The sensor flange may also include an output device. The method may also include the output device generating an alarm when turbulent flow may be detected in the injection system.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein.

Figure 1A:
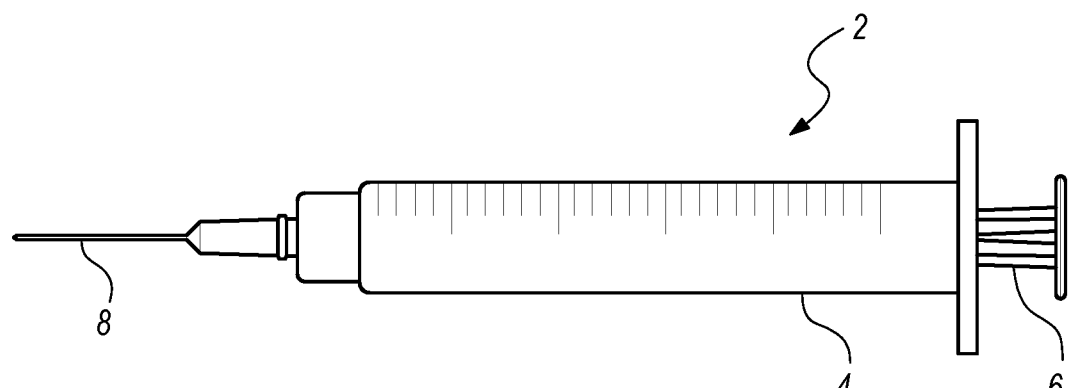
FIGS. 1A-5C illustrate various aspects of conventional injection syringe configurations.
Figure 1B:
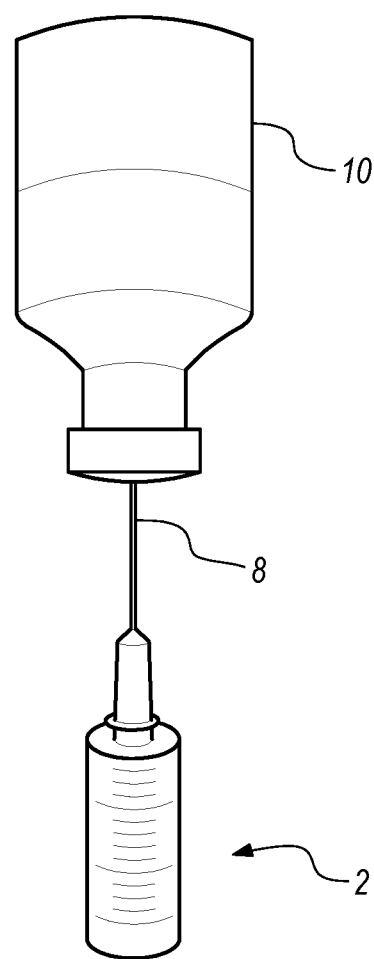
Figure 2A:
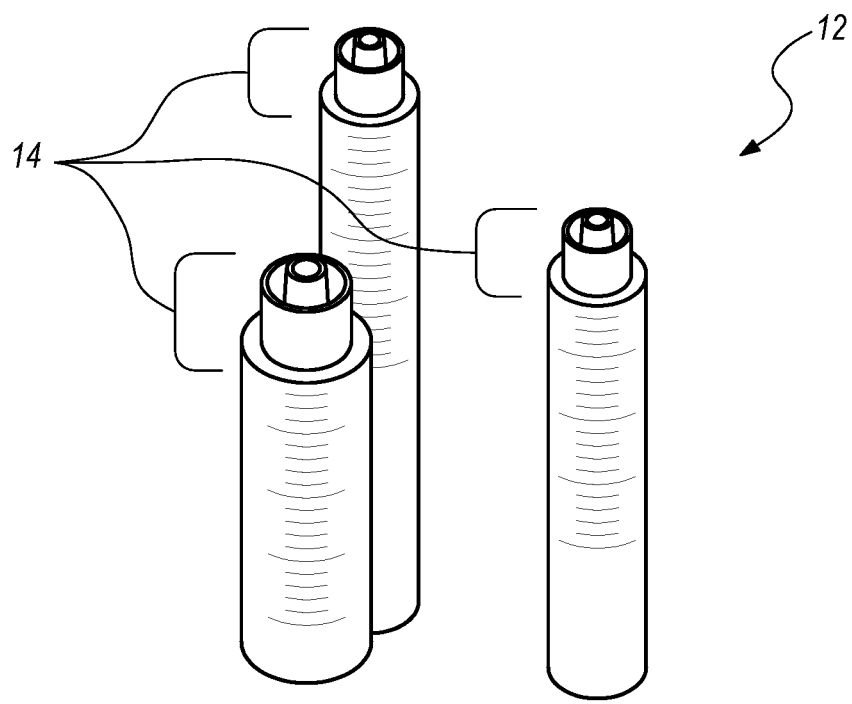
Figure 2B:
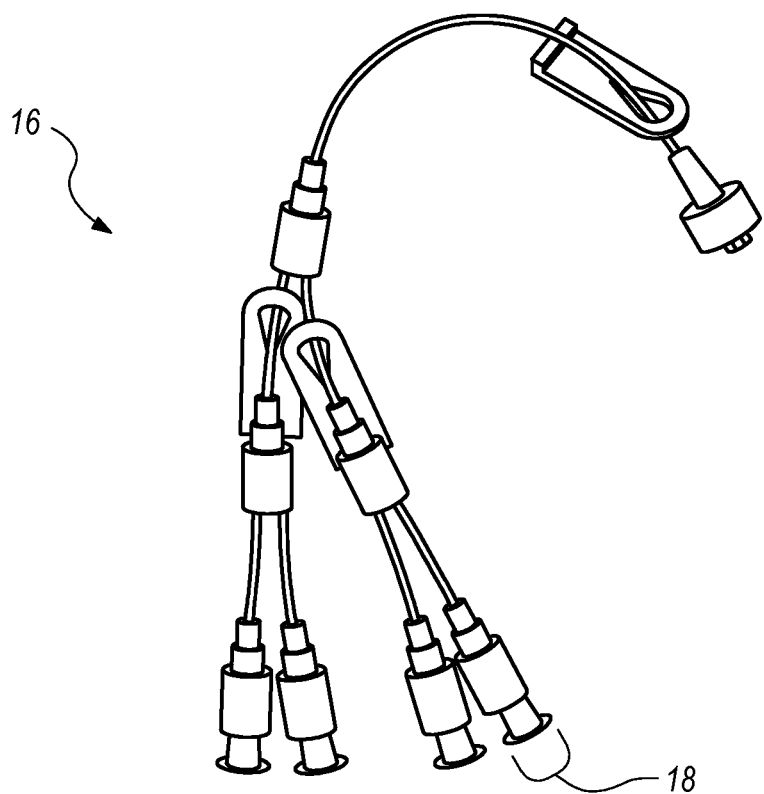
Figure 3:
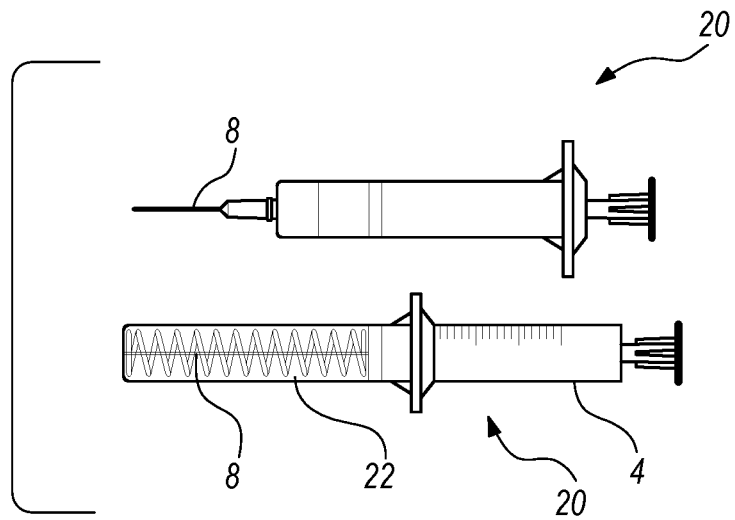
Figure 4A:
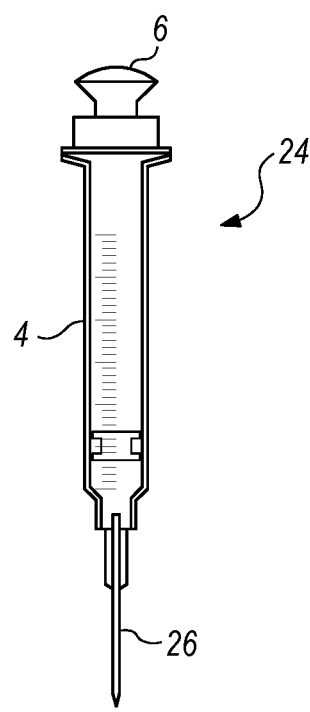
Figure 4B:
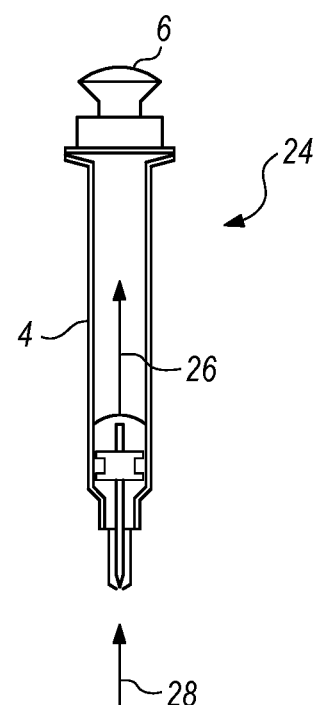
Figure 5A:
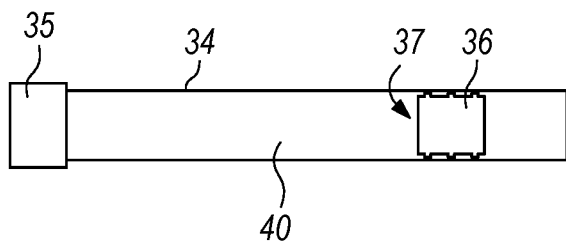
Figure 5B:
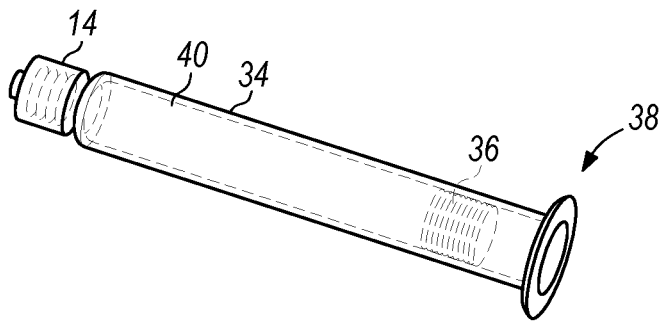
Figure 5C:
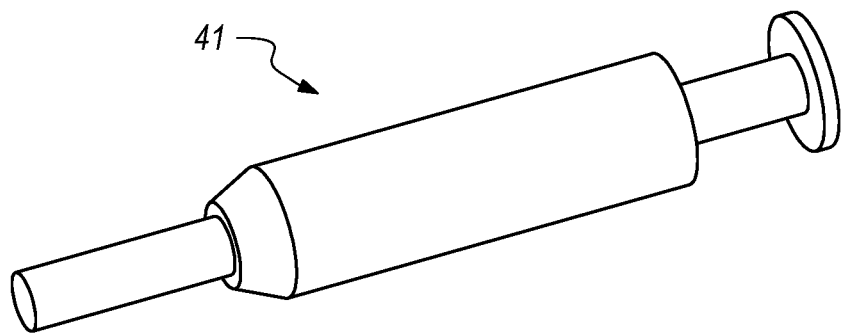

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Smart Sensor Flange

Figure 6:
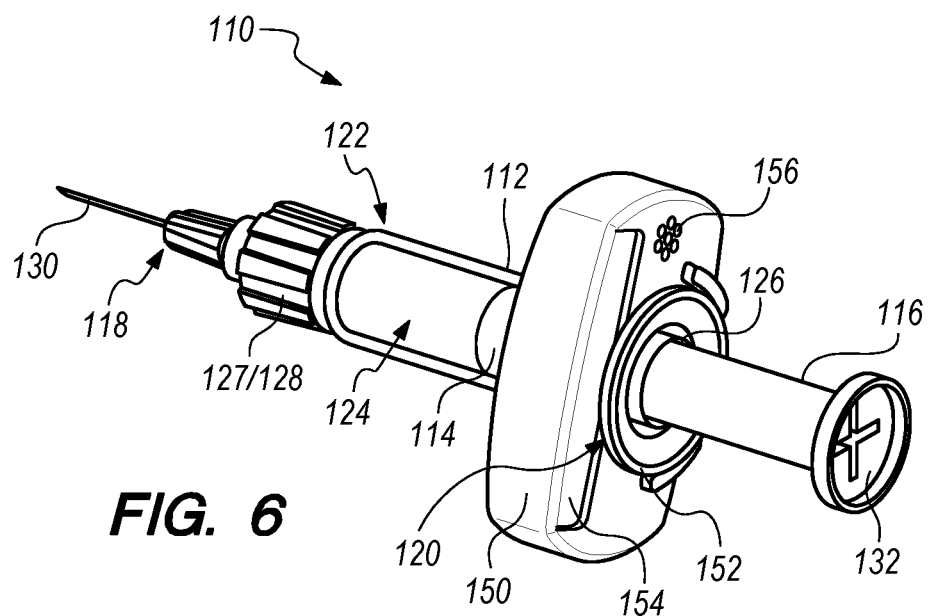
FIGS. 6 and 7 illustrate a sensor flange removably coupled to an injection system according to one embodiment.
Figure 7:
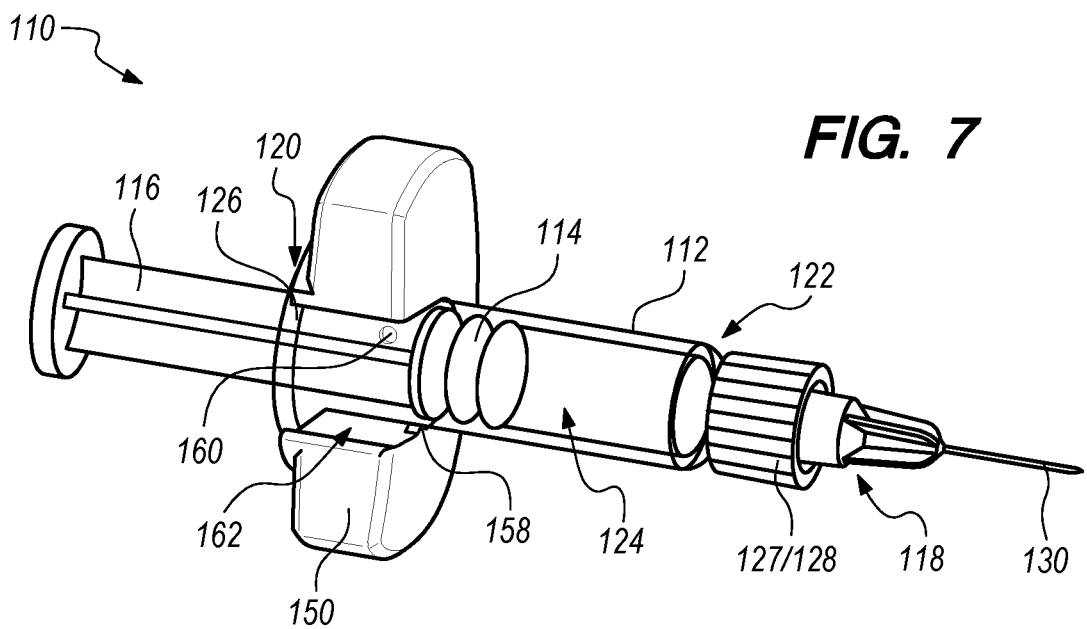

Referring to FIGS. 6 and 7, an injection system (110) includes a syringe body (112), a stopper member (114), a plunger member (116), the needle assembly (118), and a sensor flange (150) removably attached to the syringe body (112). The syringe body (112) includes an open proximal end (120) and an open distal end (122). The syringe body (112) also includes a syringe interior (124), a syringe flange (126) at the proximal end (120) thereof, and a syringe coupling member (128) at the distal end (122) thereof. In the embodiment depicted in FIGS. 6 and 7, the syringe coupling member (128) is a female Luer connector. The stopper member (114) is disposed in the syringe interior (124), and coupled to the plunger member (116), such that the plunger member (116) may be manipulated to insert the stopper member (114) distally into the syringe interior (124) to expel an injectable substance (e.g., fluid) from the syringe interior (124) through the needle assembly (118). The needle assembly (118) includes a needle coupling member (128) at a proximal end thereof and a needle (130) at a distal end thereof. In the embodiment depicted in FIGS. 6 and 7, the coupling member (128) is a female Luer connector configured to form a fluid tight connection/seal with the male Luer connector (127) at the distal end (122) of the syringe body (112). The plunger member (116) includes a proximal end pad (132) to facilitate manual manipulation of the plunger member (116) using a digit (e.g., a thumb) of a user's hand while one or more other digits of the user's hand provide an opposing force (e.g., against a distal side of the syringe flange (126) or a body disposed thereon).

The sensor flange (150) is depicted in FIGS. 6 and 7 as being removably coupled to the syringe body (112). The sensor flange (150) depicted in FIGS. 6 and 7 is designed to clip onto the syringe body (112) while being able to slide freely along a longitudinal axis of the syringe body (112) until the flange force sensor (152) on the sensor flange (150) contacts the syringe flange (126). This mounting/force sensor design has two advantages. The force measure by the force sensor (152) is substantially similar to the force applied by the user's thumb. Also, it is easy to clip on the sensor flange (150) and activate the mounting sensor (158; described below) because the target (i.e., the syringe body (112)) is relatively large. A user can snap the large opening/notch (162) in the sensor flange (150) anywhere on the length of the syringe body (112).

As shown in FIG. 6, the sensor flange (150) includes a flange force sensor (152) to detect a force applied to the sensor flange (150) in a proximal direction. In one embodiment, the flange force sensor (152) may be a partially mechanical device that measures a force applied to compress the sensor flange (150) against the syringe flange (126). In some embodiments, the force measured by the flange force sensor (152) is equal to the force applied to the plunger member (116) in a distal direction to move the stopper member (114) distally inside of the syringe interior (124). In some embodiments, the force measured by the force flange sensor (152) may be recorded to generate a force profile that can be analyzed to determine the occurrence and timing of certain injection events. For instance, if the measured force in a force profile suddenly increases, a processor (not shown) in the sensor flange (150) may determine that the stopper member (114) has reached the distal end (122) of the syringe body (112) and the injection has been completed. While the flange force sensor (152) is described as a partially mechanical device, various other sensors (e.g., resistance based, etc.) can also function as flange force sensors. Also, the time between the start of a sustained push until the end of the injection (e.g., measured by a clock) can be combined with the force applied information to determine the dose delivered; the backpressure applied by the patient's tissue; the viscosity of the drug; and other key injection parameters.

The sensor flange (150) also includes a pair of output devices to communicate with (e.g., deliver various messages, signals, and/or alarms to) a user. The sensor flange (150) includes a display (154) to communicate visually with the user. The display (154) may communicate with a binary (i.e., on/off) signal, a color signal, a written textual signal/message, icons, etc. In one embodiment, the display function is performed by an array of small lights. For instance, the time to the next injection may be represented by the number of lights illuminated in the array. Similarly, a compliance score may be represented by the number of lights illuminated in the array. The sensor flange (150) includes a speaker (156) to communicate aurally with the user. The speaker (156) may communicate with a binary (i.e., beep) sound, a tonal sound, a spoken textual signal/message (e.g., using a pre-recorded and/or computer generated voice), etc. While the output devices (154, 156) are described as a display and/or a speaker, various other output devices (e.g., haptic, etc.) can also be used with sensor flange is according to other embodiments.

Various features of the sensor flange (150) can increase user compliance through various motivation mechanisms. For instance, the syringe flange (126) is typically quite small and difficult to grasp/manipulate. The much larger sensor flange (150) provides a much more comfortable surface for manipulation (e.g., by providing a reaction force to a thumb force). The output devices (154, 156) on the sensor flange (150) may provide a user with a helpful reminder that an injection is due. The sensor flange (150) may store and display compliance data that can earn the user rewards in a compliance program. The sensor flange (150) may generate compliance scores that may motivate users to achieve higher compliance scores for "bragging rights" with family, friends, and caregivers.

As shown in FIG. 7, the sensor flange (150) includes a mounting sensor (158) to detect when the sensor flange (150) is removably coupled to the syringe body (112). In one embodiment, the mounting sensor (158) may be a partially mechanical device (e.g., a switch) that has two states. The mounting sensor (158) has an "uncoupled" state where the mounting sensor (158) is not depressed and extends from the surface of the sensor flange (150) due to a bias (e.g., driven by a spring). The mounting sensor (158) also has a "coupled" state where the mounting sensor (158) is depressed by interaction with the outer surface of the syringe body (112). The depressed mounting sensor (158) sends a message to a processor (not shown) in the sensor flange (150) to communicate that the sensor flange (150) is removably coupled to the syringe body (112). While the mounting sensor (158) is described as a partially mechanical device, various other sensors (e.g., optical, magnetic, electrical, etc.) can also function as mounting sensors.

The sensor flange (150) also includes a motion sensor (160) to measure a motion relating to injection using the injection system (110). In one embodiment, the measured motion is a movement of the plunger member (116) relative to the syringe body (112). For instance, the motion sensor (160) may be an optical sensor configured to trigger when a pre-determined optical marker (not shown) on the plunger member (116) passes by (i.e., is read by) the optical motion sensor (160). Such an optical motion sensor (160) may read the pre-determined optical marker using a computer vision system like a barcode reader. By using such a motion sensor (160) and disposing the pre-determined optical marker on the plunger member (116) such that the pre-determined optical marker passes by the motion sensor (160) at the end of the injection, the motion sensor (160) can be used to detect the end of an injection. A similar configuration can be used with a magnetic motion sensor (160) and a magnetic marker (not shown) on the plunger member (116). The sensor flange (150) may also include a clock to enable the measurement of a change in position over time (velocity) and/or a change in velocity over time (acceleration) of the plunger member (116) relative to the sensor flange (150).

In other embodiments, the motion sensor (160) may continuously measure a motion of the plunger member (116), such as motion along a longitudinal axis of the injection system (110). The motion sensor (160) may be an optical sensor that takes a series of still photographs/images of the plunger member (116) in motion. The series of still images are transmitted to and image processor (not shown) in the sensor flange (150). The image processor analyzes the series of still images to detect patterns therein and calculates a pixel shift from one image to the next in the series. In particular pixels can be identified at edges or other distinct points on the images. This pixel shift can be used to calculate the distance moved by the pixel (and therefore the plunger member (116)) from one image to the next in the series. The pixel shift together with a pre-determined time between image frames can be used to calculate a velocity of the plunger member (116) relative to the sensor flange (150). The optical motion sensor (160) may include optics configured to detect small visual features in the plunger member (116) such as scratches, defects, texture, etc. In some embodiments, the distance moved by the plunger member (116) is summed, and when the summed distance reaches approximately a target distance (i.e., the distance sufficient for the stopper member (114) to reach the distal end (122) of the syringe body (112)), the sensor flange (150) determines that a full dose has been delivered.

Figure 8:
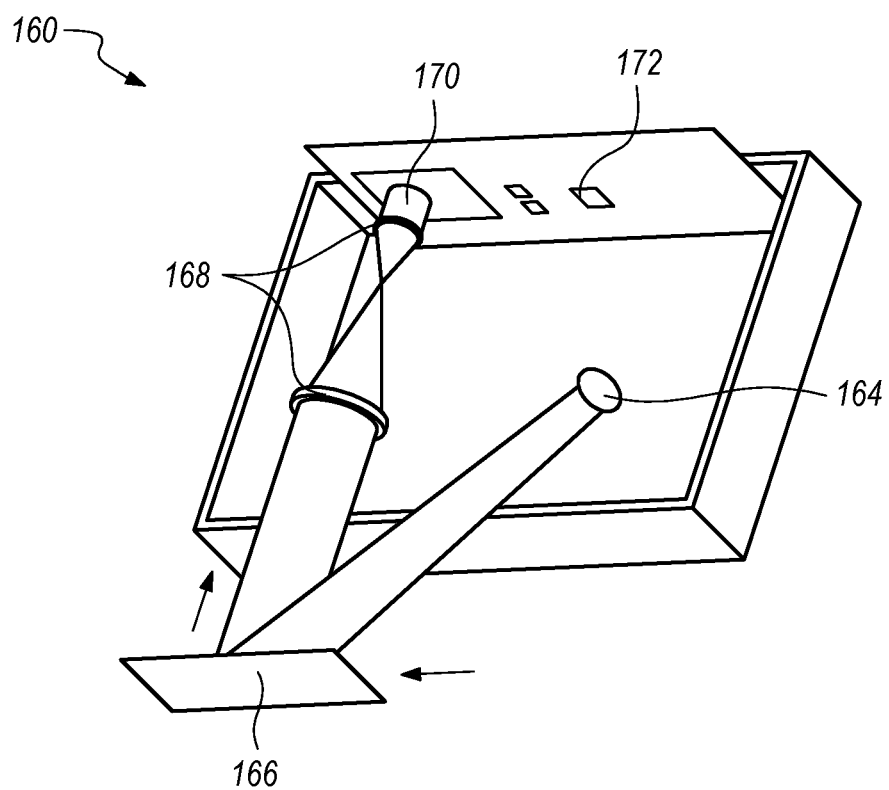
FIG. 8 illustrates an optical motion sensor for use in a sensor flange according to one embodiment.

Such an optical motion sensor (160) is depicted in FIG. 8. The optical motion sensor (160) includes an LED light source (164) to direct light to a measured surface (166), a plurality of lenses (168) to focus the reflected light from the measured surface (166), a 2-D camera (170), and an image processor (172). The sensor flange (150) may also include a clock to enable the measurement of a change in position over time (velocity) and/or a change in velocity over time (acceleration) of the plunger member (116) relative to the sensor flange (150).

Figure 9:
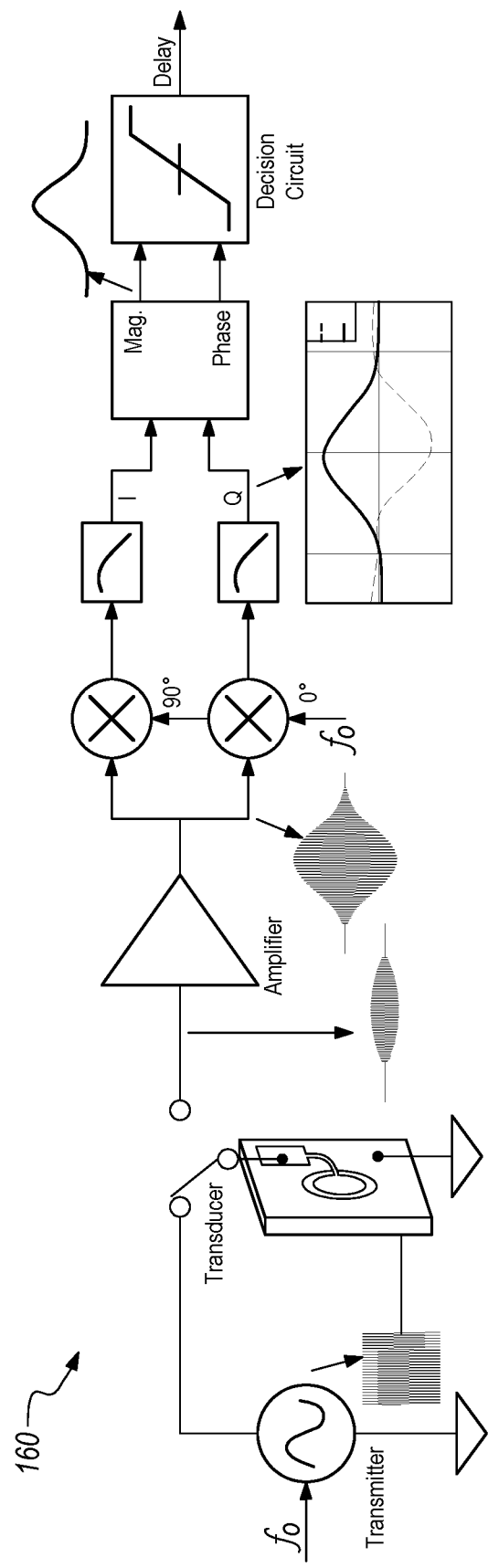
FIG. 9 illustrates an acoustic rangefinder for use in a sensor flange according to one embodiment.

In other embodiments, the motion sensor (160) may be a rangefinder (e.g. acoustic, infrared, laser, etc.) that measures the distance between the sensor flange (150) and a user's thumb. One advantage of using a rangefinder motion sensor (160) over other optical motion sensors is elimination of the need for visually distinct portions of the surface of the syringe body (112). Further, writing and other user-generated markings on the syringe body (112) will not interfere with a rangefinder motion sensor (160). FIG. 9 depicts an exemplary acoustic rangefinder including a narrowband ultrasound transducer. The rangefinder motion sensor (160) depicted in FIG. 9 includes a narrowband ultrasound transducer, a transmitter, an amplifier, and a decision circuit. In some embodiments, an acoustic rangefinder can also emit a sound that may be detected by an acoustic sensor (described below). A sonic rangefinder can also produce audible output, thereby eliminating the need for a speaker. The sensor flange (150) may also include a clock to enable the measurement of a change in position over time (velocity) and/or a change in velocity over time (acceleration) of the plunger member (116) relative to the sensor flange (150).

In other embodiments, the motion sensor (160) may be an acoustic sensor that measures a sound related to movement of the plunger member (116). In one embodiment, completion of injection (i.e., movement of the plunger member (116) to the distal end (122) of the syringe body (112)) results in the generation of a distinct sound. For instance, in some of the safety needles described in U.S. patent application Ser. Nos. 14/696,342, 14/543,787, 14/321,706, 62/416,102, 62/431,382, and 62/480,276, the contents of which have been incorporated herein by reference, completion of injection causes retraction of the needle (130) at least partially into the plunger member (116). This needle retraction is associated with the release of a spring-loaded latch (not shown), which is accompanied by a distinct sound. The acoustic motion sensor (160) can be triggered by this distinct sound (e.g., one or more particular frequencies and amplitudes) to indicate that injection has been completed. In other embodiments, the plunger member (116) or other components of the injection system (110) (e.g., an acoustic rangefinder thereof) can be configured to emit various sounds (e.g., specific frequencies, trips, clicks, "dog whistles," etc.) that can be detected by the acoustic motion sensor (160).

As shown in FIG. 7, the sensor flange (150) includes an opening (162) configured to allow the sensor flange (150) to be snapped onto the proximal end (120) of the syringe body (112) against the syringe flange (126). The sensor flange (150) may be held on to the syringe body (112) by an interference fit.

Although not shown in FIGS. 6 and 7, the sensor flange (150) can include a power source to drive the various sensors (152, 158, 160) and output devices (154, 156). The power source may be a battery or a power generator operatively coupled to the injection system (110), such as to the plunger member (116) to generate power with relative movement of various components of the injection system (110). Alternatively, the power source may utilize a photoelectric solar cell to charge a rechargeable battery or a capacitor for storage of electrical power for use by the sensor flange.

Although not shown in FIGS. 6 and 7, the sensor flange (150) can also include a communication link to allow the sensor flange (150) to exchange data with a computing device. In some embodiments, the computing device may be a user's smart phone which hosts an application configured to work with the sensor flange (150). The communication link can include a Bluetooth link, a WiFi link, a WiFi Direct link, a near field communication link, a cellular network link, etc. The communication link can facilitate exchange of data including injection setup data and post-injection data. Injection setup data includes, but is not limited to, current date and time, first injection date and time, injection frequency, syringe type, viscosity, temperature, warming time, maximum shear force, multiple injection site regimen data, reward program data, and educational/marketing data. Post-injection data includes, but is not limited to, injection date and time, any of the measured injection parameters described above, and injection error related data. Injection errors include, but are not limited to, drug identity error, injection timing error, dosage error, shear force error, de-bubbling error, amount of drug remaining in the syringe after the injection has been performed, and multi-site injection error. The post-injection information can be used to track patient compliance, drive reward programs, inform insurance programs, etc. Sufficient memory can be provided to store several days or weeks of post-injection data. Storing the post-injection data in memory insures that no post-injection data is lost even if the user uploads to other computing devices rarely or not at all. This will facilitate reliable maintenance of post-injection data (e.g., for compliance), even under adverse circumstances.

Although not shown in FIGS. 6 and 7, the sensor flange (150) can further include a memory module to store data. The stored data includes, but is not limited to, the injection setup data and post-injection data described above. Storing the injection setup data allows for a sensor flange (150) to be "programmed" (e.g., wirelessly) a long time before then injection is given using the injection system (100). Storing the post-injection data allows a sensor flange (150) to download/send (e.g., wirelessly) the injection data to a healthcare provider in a batch operation at a convenient time. For instance, post-injection data can be batch downloaded when a patient picks up medication at a pharmacy. The post-injection data can be used to monitor patient compliance to improve patient care. The post-injection data can also be used to calculate compliance course, facilitate compliance reward programs, modify insurance premiums, etc.

Moreover, although not shown in FIGS. 6 and 7, the sensor flange (150) can include a temperature sensor to manage injection systems that are refrigerated as required by temperature-sensitive injectable substances. Temperature sensors include physical thermocouples, infrared thermometers, etc. Such temperature sensors can be configured to measure the temperature of the syringe body (112) to thereby determine a temperature of the injectable substance contained therein. Injection systems (110) having temperature sensors can be configured to alert the user (e.g., using an output device) when the temperature of the syringe body (112) and the injectable substance contained therein reach an appropriate range for injection. Such systems can also store measured temperatures at injection times. Further, such systems can use the measured temperature to calculate an approximate time until the syringe body (112) and the injectable substance contained therein reach an appropriate range for injection. Additionally, the temperature measurements of the drug may be used to calculate the viscosity of the drug for use in performing injection pressure or flow rate calculations.

Alternatively, the user can be instructed to clip on the sensor flange (150) and wait a certain pre-determined period of time to allow a refrigerated medication to warm up before injection. Then an output device (e.g., a speaker (156)) can signal when this approximate warm up time has expired. This method of signaling expiration of a warm-up time does not require a temperature sensor. Using injection force and injection time, the viscosity of the drug could be verified, and the warm up time adjusted for the next injection.

Although not shown in FIGS. 6 and 7, the sensor flange (150) can further include a processor to perform various calculations and control various sensor flange components. The processor may include a clock and can be programmed to instruct an output device to deliver an alarm signal to a user when it is time for an injection. The output device may be instructed to deliver the alarm signal for a pre-determined amount of time (e.g., one hour), then to be silent for a predetermined amount of time (e.g., one hour), and to repeat the cycle of alarm signal in silence until the sensor flange (150) is mounted on a syringe body (112) for injection. The processor can also be programmed to instruct an output device to provide advice to the patient when an injection error is detected. For instance, if a user is late for an injection, the processor can instruct an output device to offer advice to the user regarding the late injection based on the identity of the injectable substance, which may have been received as part of the injection setup data.

Although not shown in FIGS. 6 and 7, the sensor flange (150) may also include an orientation sensor to detect when the syringe body (112) is pointed "upward."

Figure 10A:
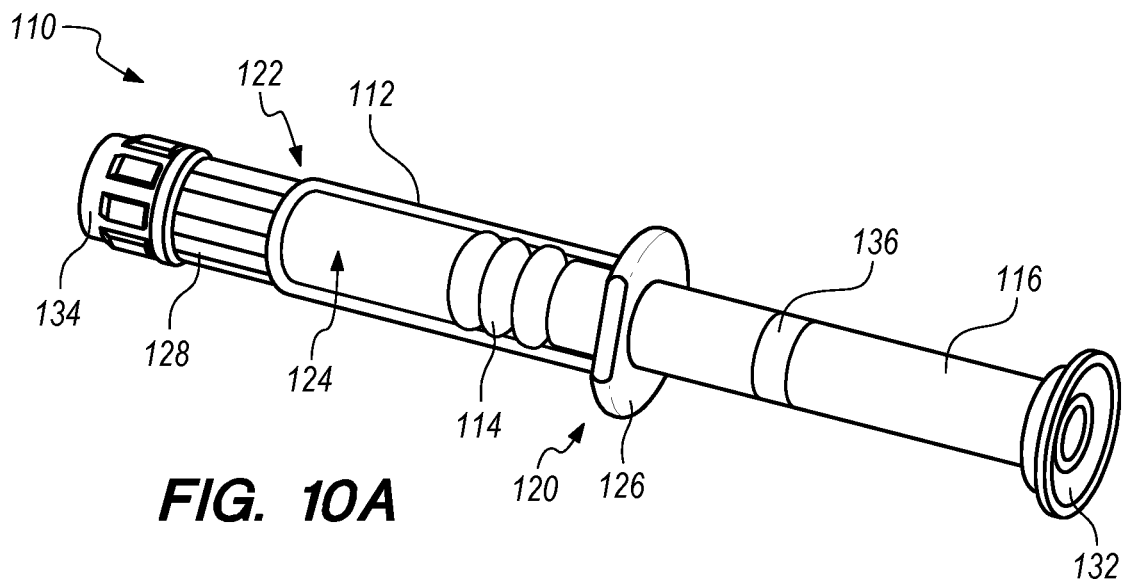
FIG. 10A illustrates an injection system to which a sensor flange can be removably coupled according to one embodiment.

FIGS. 10A-10F depict an injection system (110) according to another embodiment being used to inject an injectable substance and collect injection information. As shown in FIG. 10A, the injection system (110) includes a syringe body (112) having proximal and distal ends (120, 122), a syringe interior (124), a syringe flange (126) at the proximal end (120) thereof, and a syringe coupling member (i.e., Luer connector) the distal end (122) thereof. The injection system (110) also includes a stopper member (114) disposed in the syringe interior (124) and coupled to a plunger member (116). Medicine may be pre-filled inside the syringe interior (124). The plunger member (116) includes a proximal end pad (132) to facilitate application of distally directed force to move the stopper member (114) distally relative to the syringe body (112). The plunger member (116) also includes a marker (136) to be read by a sensor flange (see FIG. 10D).

The marker (136) may include information relating to the injection system (110) including, but not limited to, syringe type, injectable substance identity, and injectable substance characteristics such as viscosity, transparency, color, injection temperature, friction force between the syringe and the stopper member, allowable shear on medicine during injection, preferred injection speed, or others. The marker (136) may be lines, a barcode, text, a 2D barcode, or other patterns that may be read by the electronic devices in the sensor flange to record medicine information and/or movement of the plunger member. The marker (136) may also be located on the syringe body (112), the syringe flange (126), or other locations on the injection system such that the sensor flange (150 FIG. 10B) is able to read the marker during or after installation. Alternatively, the information relating to the injection may be pre-programmed into the sensor flange at the time of manufacture, or downloaded to the flange at a later time. The injection system (110) further includes a Luer cap (134) to fluidly seal the female Luer connector (128) before a needle assembly is removably coupled thereto (see FIG. 10C).

Figure 10B:
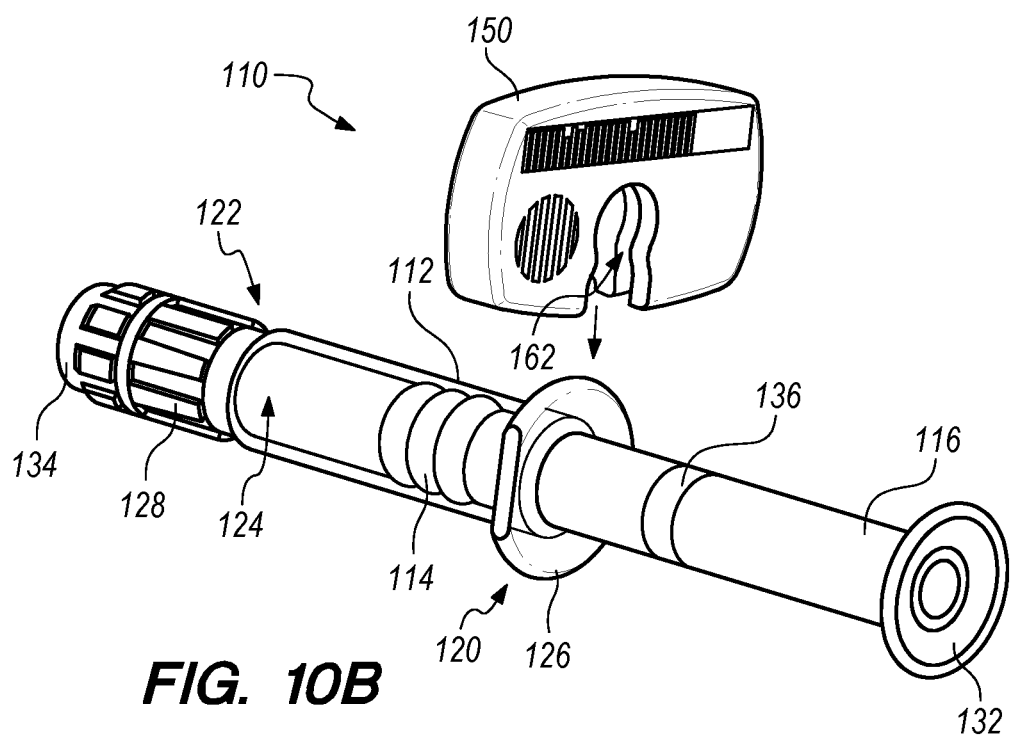
FIGS. 10B-10E illustrate a sensor flange removably coupled to an injection system according to one embodiment.

FIG. 10B depicts the next step in the preparation/injection process in which a sensor flange (150) is removably coupled to the syringe body (112). The sensor flange (150) includes an opening (162) configured to allow the sensor flange (150) to be snapped onto the proximal end (120) of the syringe body (112) against the syringe flange (126). Unlike the sensor flange (150) depicted in FIGS. 6 and 7, which is snapped onto the syringe body (112) so that proximal surface of the sensor flange (150) abuts a distal surface of the syringe flange (126), the opening (162) in the sensor flange (150) depicted in FIG. 10B is configured such that the syringe flange (126) is disposed within the sensor flange (150) when the sensor flange (150) is mounted on the syringe body (112). The sensor flange (150) may be held on to the syringe body (112) by an interference fit.

Figure 10C:
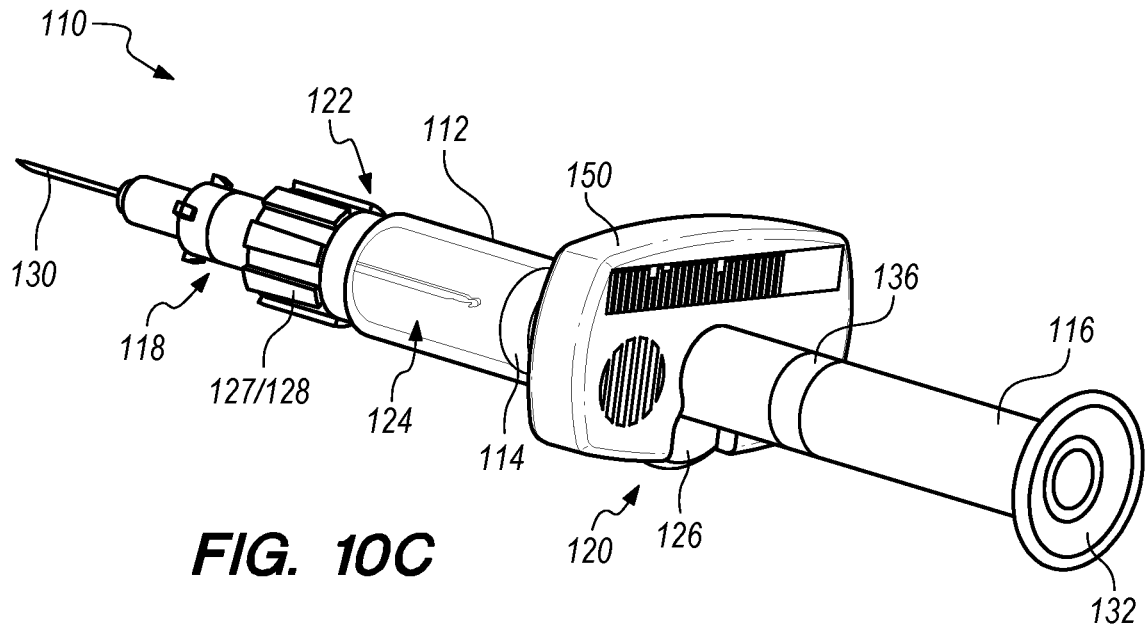

FIG. 10C depicts the sensor flange (150) removably coupled to the syringe body (112). In this configuration, the injection system (110) is ready for injection while collecting injection related information. FIG. 10C also depicts a predetermined optical marker (136) on the plunger member (116). The pre-determined optical marker (136) is configured to be read by an optical sensor in the sensor flange (150) when the pre-determined optical marker (136) passes through the sensor flange (150). The optical sensor may read the pre-determined optical marker (136) using a computer vision system like a barcode reader. By disposing the pre-determined optical marker (136) on the plunger member (116) such that the pre-determined optical marker enters and is read by the sensor flange (150) at the end of the injection, the sensor flange (150) can be used to detect the end of an injection. While a singular optical marker (136) is shown in FIG. 10C, the sensor flange (150) system may be configured to utilize multiple optical markers to increase the fidelity or resolution of the motion sensor.

Figure 10D:
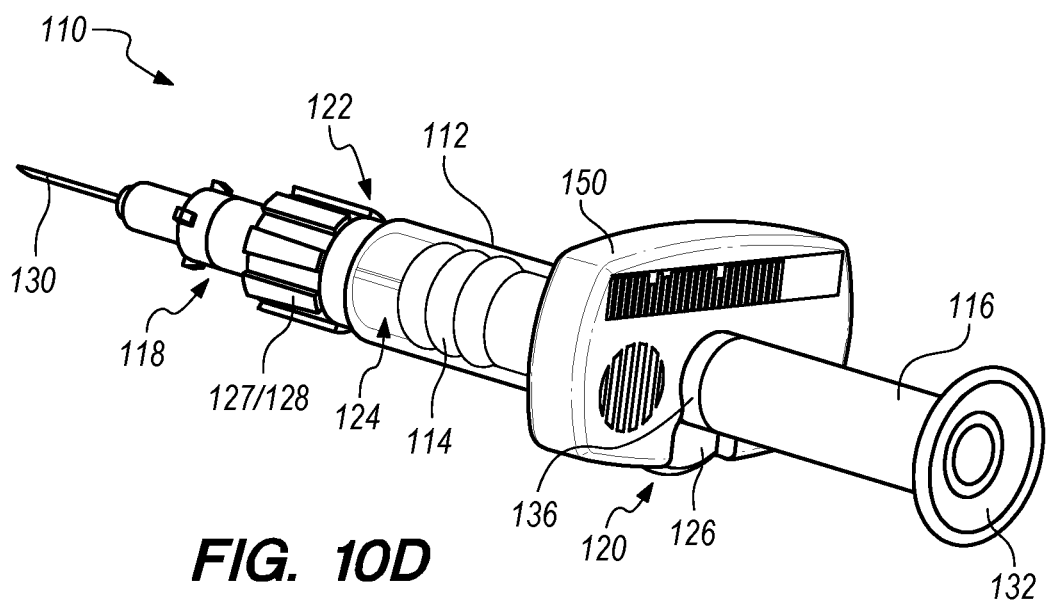

FIG. 10D depicts the injection system (110) after a distally directed force has been applied to the proximal end pad (132) of the plunger member (116). In one embodiment, the distally directed force can be applied to the proximal end pad (132) with a thumb of a user's hand while one or more other digits of the user's hand are anchored against a distal surface of the sensor flange (150). The other digits of the user's hand may also apply proximally directed force to the distal surface of the sensor flange (150) to move the plunger member (116) and the stopper member (114) attached thereto distally in the syringe interior (124). Moving the stopper member (114) distally into the syringe interior (124)

increases the pressure in the syringe interior (124) thereby forcing any injectable substance in the syringe interior (124) out through the needle (130) to inject the injectable substance into tissue pierced by the needle (130). FIG. 10D also depicts the pre-determined optical marker (136) on the plunger member (116) in a position before passing into and being read by the sensor flange (150), which corresponds to a stopper member (114) member position near (by not at) the end of injection.

Figure 10E:
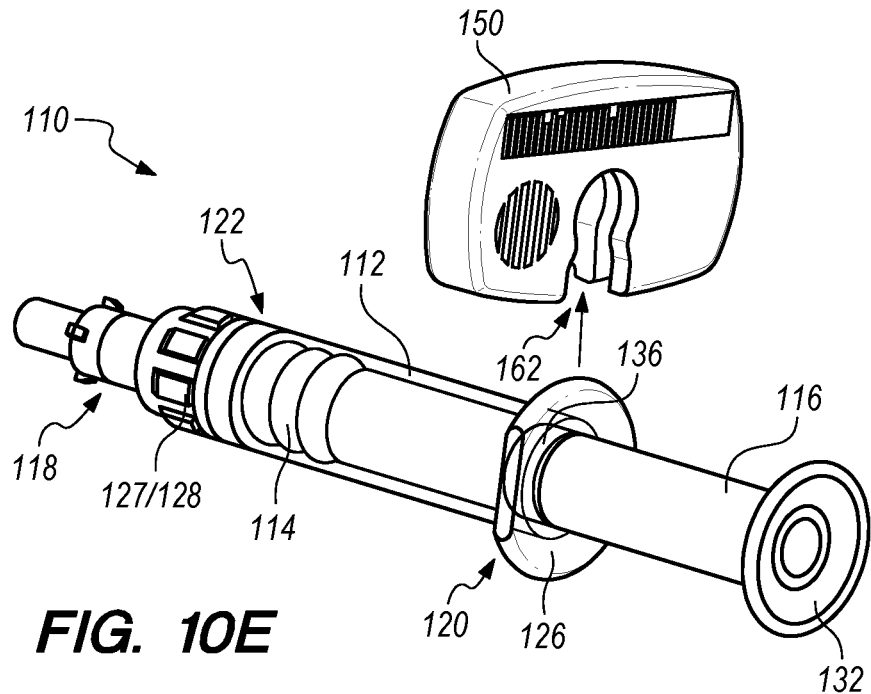

FIG. 10E depicts the injection system (110) after the pre-determined optical marker (136) has entered into and been read by the sensor flange (150). The pre-determined optical marker (136) can also encode injection setup information to be read by the optical sensor in the sensor flange (150). Injection setup data includes, but is not limited to, first injection date and time, injection frequency, syringe type, temperature, viscosity, warming time, maximum shear force, multiple injection site regimen data, reward program data, and educational/marketing data. FIG. 10E also depicts the stopper member (114) at the distal end (122) of the syringe body (112) at the completion of injection. The pre-determined optical marker (136) is disposed on the plunger member (116) such that when the stopper member (114) at the distal end (122) of the syringe body (112), the pre-determined optical marker (136) is positioned in the sensor flange (150) for reading by an optical sensor therein. Accordingly, the sensor flange (150) reading the pre-determined optical marker (136) corresponds to the injection event of injection completion.

After injection completion, the needle (130) may or may not be retracted into the syringe interior (124) and/or plunger member (116), as described in U.S. patent application Ser. Nos. 14/696,342, 14/543,787, 14/321,706, 62/416,102, 62/431,382, and 62/480,276, the contents of which have been incorporated herein by reference. Also after injection completion, the sensor flange (150) may be removed from the syringe body (112) and reused with another syringe body (112) for another injection. The used syringe body (112), stopper member (114), plunger member (116), and needle assembly (118) may be safely disposed after removal of the sensor flange (150). Reusability of the sensor flange (150) reduces healthcare costs by reusing a relatively more costly (e.g., compared to the syringe body (112)) part of the injection system (110).

Figure 10F:
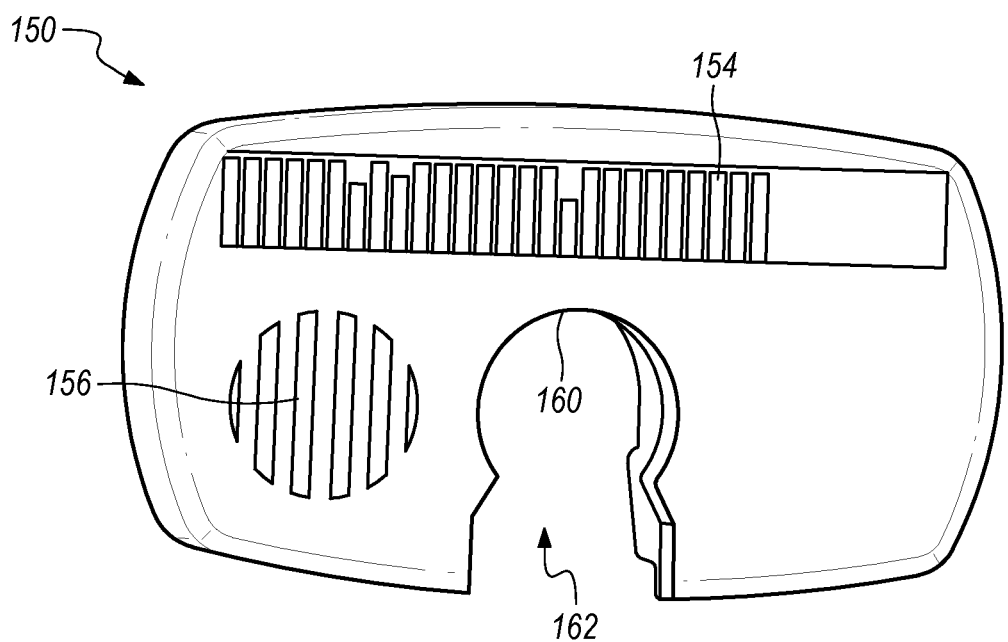
FIG. 10F illustrates a sensor flange according to one embodiment.

FIG. 10F depicts a sensor flange (150) for use in the injection system (110) depicted in FIGS. 10A-10E. The sensor flange (150) includes a pair of output devices (154, 156), an opening (162), and an optical sensor (160) disposed adjacent to the opening (162). The output devices (154, 156) communicate with (e.g., deliver various messages, signals, and/or alarms to) a user. The sensor flange (150) includes a display (154) to communicate visually with the user. The display (154) may communicate with a binary (i.e., on/off) signal, a color signal, icons, a written textual signal/message, etc. In one embodiment, the display function is performed by an array of small lights. For instance, the time to the next injection may be represented by the number of lights illuminated in the array. Similarly, a compliance score may be represented by the number of lights illuminated in the array. The sensor flange (150) also includes a speaker (156) to communicate aurally with the user. The speaker (156) may communicate with a binary (i.e., beep) sound, a tonal sound, a spoken textual signal/message (e.g., using a pre-recorded and/or computer generated voice), etc. While the output devices (154, 156) are described as a display and/or a speaker, various other output devices (e.g., haptic, etc.) can also be used with sensor flange is according to other embodiments.

Having described exemplary sensor flanges, methods for collecting injection information using sensor flanges according to various embodiments will not be described.

Figure 11A:
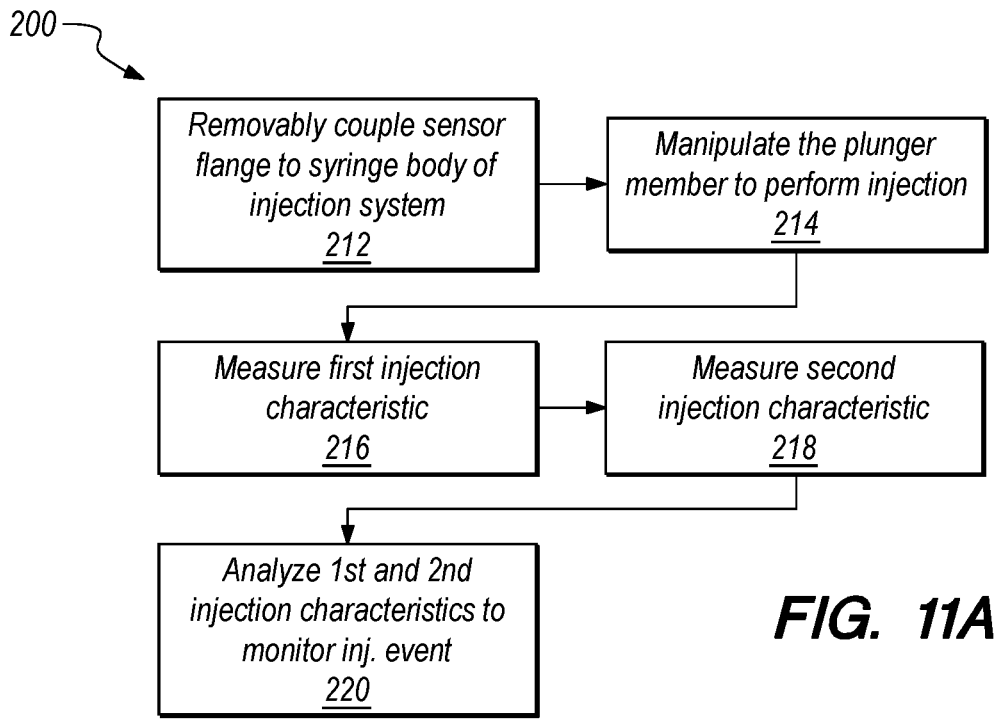
FIGS. 11A-17 and 44 illustrate methods of collecting injection information according to various embodiments.

FIG. 11A depicts a method (200) of collecting injection information according to one embodiment. At step (212), a sensor flange, such as the sensor flanges (150) described above, is removably coupled to the syringe body of injection system. The injection system may be similar or identical to the injection systems (110) described above. The sensor flange may be secured to the syringe body using an interference fit.

At step (214), the plunger member of the injection system is manipulated to perform the injection. For instance, force may be applied to a proximal end pad of the plunger member using a digit (e.g., a thumb) of a user's hand while one or more other digits of the user's hand provide an opposing force (e.g., against a distal side of the syringe flange or a sensor flange disposed thereon).

At step (216), the sensor flange measures a first injection characteristic using a first sensor. Similarly, at step (218), the sensor flange measures a second injection characteristic using a second sensor. The first and second sensors may be any known type of sensor including, but not limited to, acoustic sensors, motion sensors, proximity sensors, temperature sensors, force sensors, accelerometer sensors, orientation sensors, and optical sensors. The first and second sensors may be the same type of sensor, or they may be different types of sensors. The types of sensors may be selected to measure the types of injection characteristics required by the method (200).

At step (220), the sensor flange (i.e., a processor therein) analyzes the first and second injection characteristics to monitor (e.g., detect, measure, determined, etc.) an injection event (e.g., completion of injection, plunger force, sheer force, injection error, etc.) The type of injection event monitored during the method (200) determines the types of injection characteristics measured in the types of sensors in the sensor flange.

Figure 11B:
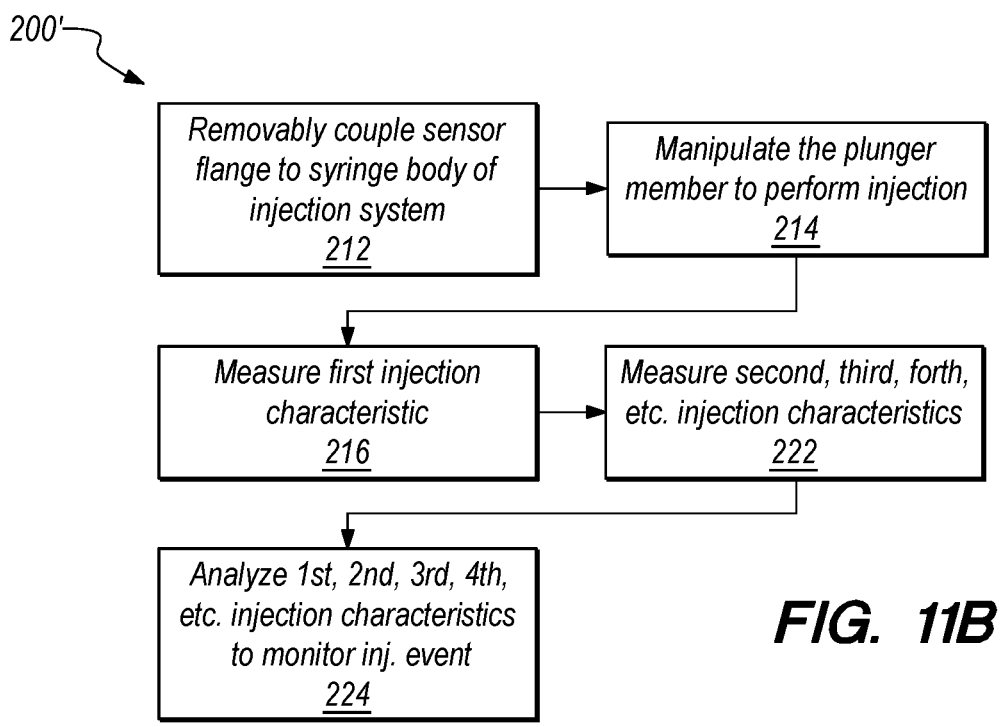

FIG. 11B depicts a method (200') of collecting injection information according to another embodiment. The method (200') depicted in FIG. 11B is similar to the one depicted in FIG. 11A. However, instead of measuring and analyzing only first and second injection characteristics (as in the method (200) in FIG. 11A), the method (200') depicted in FIG. 11B measures and analyzes more than two injection characteristics.

At step (212), a sensor flange, such as the sensor flanges (150) described above, is removably coupled to the syringe body of injection system. The injection system may be similar or identical to the injection systems (110) described above. The sensor flange may be secured to the syringe body using an interference fit.

At step (214), the plunger member of the injection system is manipulated to perform the injection. For instance, force may be applied to a proximal end pad of the plunger member using a digit (e.g., a thumb) of a user's hand while one or more other digits of the user's hand provide an opposing force (e.g., against a distal side of the syringe flange or a sensor flange disposed thereon).

At step (216), the sensor flange measures a first injection characteristic using a first sensor.

At step (222), the sensor flange measures second, third, fourth, etc. injection characteristic using second, third, fourth, etc. sensors. The first, second, third, fourth, etc.

sensors may be any known type of sensor including, but not limited to, acoustic sensors, motion sensors, proximity sensors, temperature sensors, force sensors, accelerometer sensors, orientation sensors, and optical sensors. The first, second, third, fourth, etc. sensors may be the same type of sensor, or they may be different types of sensors. The types of sensors may be selected to measure the types of injection characteristics required by the method (200').

At step (224), the sensor flange (i.e., a processor therein) analyzes the first, second, third, fourth, etc. injection characteristics to monitor (e.g., detect, measure, determined, etc.) an injection event (e.g., completion of injection, plunger force, sheer force, injection error, etc.) The type of injection event monitored during the method (200') determines the types of injection characteristics measured in the types of sensors in the sensor flange.

Figure 12:
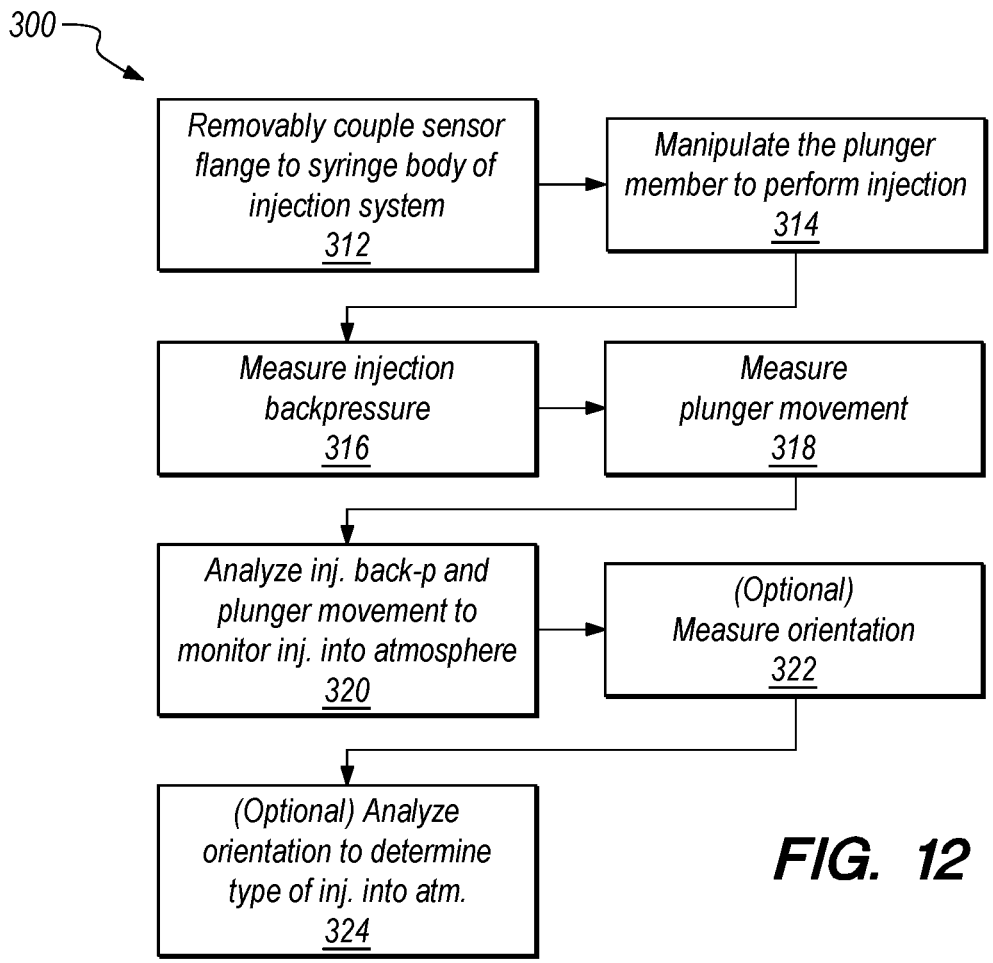

FIG. 12 depicts a method (300) of collecting injection information according to another embodiment. At step (312), a sensor flange, such as the sensor flanges (150) described above, is removably coupled to the syringe body of injection system. The injection system may be similar or identical to the injection systems (110) described above. The sensor flange may be secured to the syringe body using an interference fit.

At step (314), the plunger member of the injection system is manipulated to perform the injection. For instance, force may be applied to a proximal end pad of the plunger member using a digit (e.g., a thumb) of a user's hand while one or more other digits of the user's hand provide an opposing force (e.g., against a distal side of the syringe flange or a sensor flange disposed thereon).

At step (316), the sensor flange measures an injection back pressure using a force sensor, as described above. For instance, the force sensor on the sensor flange may measure the proximally directed force on a surface (distal, proximal, interior, etc.) of the sensor flange, as the plunger member is moved into the syringe interior to perform the injection. The force on the sensor flange is approximately equal to the force applied to the plunger member at the stopper member attached thereto to perform the injection. In some embodiments, the force on the sensor flange is continuously measured in a force profile is generated and stored in a memory of the sensor flange.

At step (318), the sensor flange measures a plunger movement using a motion sensor, as described above. For example, the motion sensor may be an optical sensor, an IR sensor, an acoustic sensor, an ultrasound rangefinder, etc. The amount of motion (i.e., distance moved) detected the motion sensor can be combined with elapsed time from a clock in the sensor flange to derive a speed and an acceleration of the motion. In some embodiments the sensor flange continuously measures distance, speed, and/or acceleration of the plunger and stores the measured parameters in a memory of the sensor flange.

At step (320), the sensor flange (i.e., a processor therein) analyzes the injection back pressure and a plunger movement to monitor (i.e., detect) an injection into atmosphere event. For instance, the processor in the sensor flange can be programmed to detect an injection into atmosphere event if the injection backpressure remains substantially low while the plunger member moves distally. The sensor flange may utilize fluid flow equations (for example; fluid flow through an orifice, Bernoulli's equations, Hagen-Poiseuille equation, or other methodologies) to compute an expected fluid pressure differential between the injection backpressure in the syringe medicine chamber and the pressure at the tip of the needle. The sensor flange may utilize certain parameters of the injection system (e.g., needle dimension, syringe body dimension, stopper member dimension, and injectable substance (e.g., medicine) properties) to perform this calculation. Parameters of the injection system include, but are not limited to, internal diameter of the needle, length of the needle, tip geometry of the needle, diameter of the syringe body, force on the sensor flange or proximal end pad of the plunger member, rate of motion of the plunger member, dynamic and static frictional forces between the stopper member and the syringe body, temperature and/or viscosity of the injectable substance (e.g., medicine), density of the injectable substance (e.g., medicine), and/or other metrics to perform the calculations. The injection backpressure may be calculated by measuring the force applied to the proximal end pad/sensor flange, subtracting frictional forces from the stopper member sliding in the syringe interior, and dividing the result by the cross sectional area of the syringe interior. The sensor flange may determine an injection into atmosphere if the calculated pressure drop indicates a pressure at the tip of the needle of approximately 1 atmosphere. The sensor flange may determine an injection into the patient if the calculated pressure at the tip of the needle is greater than 1 atmosphere. An injection into atmosphere event may or may not be an injection error depending on its duration and the orientation of the injection system during the injection into atmosphere event. For instance, air bubbles in a syringe interior may be evacuated by positioning the syringe body with the needle pointing generally upward and briefly injecting into the atmosphere to force the air bubbles that have moved to the distal end/top of the syringe interior out through the needle. On the other hand, if the injection into atmosphere event lasts substantially through the entire injection (i.e. until the stopper member has reached the distal end of the syringe interior), that indicates an error where injection occurred before the needle was properly position in the target tissue. In either case, the injection into atmosphere event, its timing, and its duration can be stored in a memory of the sensor flange.

At optional step (322), the sensor flange measures an orientation of the syringe flange and therefore of the syringe body coupled thereto. At optional step (324), the processor and the syringe flange analyzes the orientation to determine the type of injection into atmosphere event. If the orientation of the syringe body is generally upward and the duration of the injection into atmosphere event is relatively short, the processor will identify the injection into atmosphere event as de-bubbling. If the orientation of the syringe body is not generally upward and the injection into atmosphere event last substantially through the entire injection, the processor will identify the injection into atmosphere event as an error. In either case the orientation of the syringe body can be stored in a memory of the sensor flange. The sensor flange may also deliver an alarm signal (e.g., visible or audible) when an injection into atmosphere error event is detected to alert the user.

Figure 13:
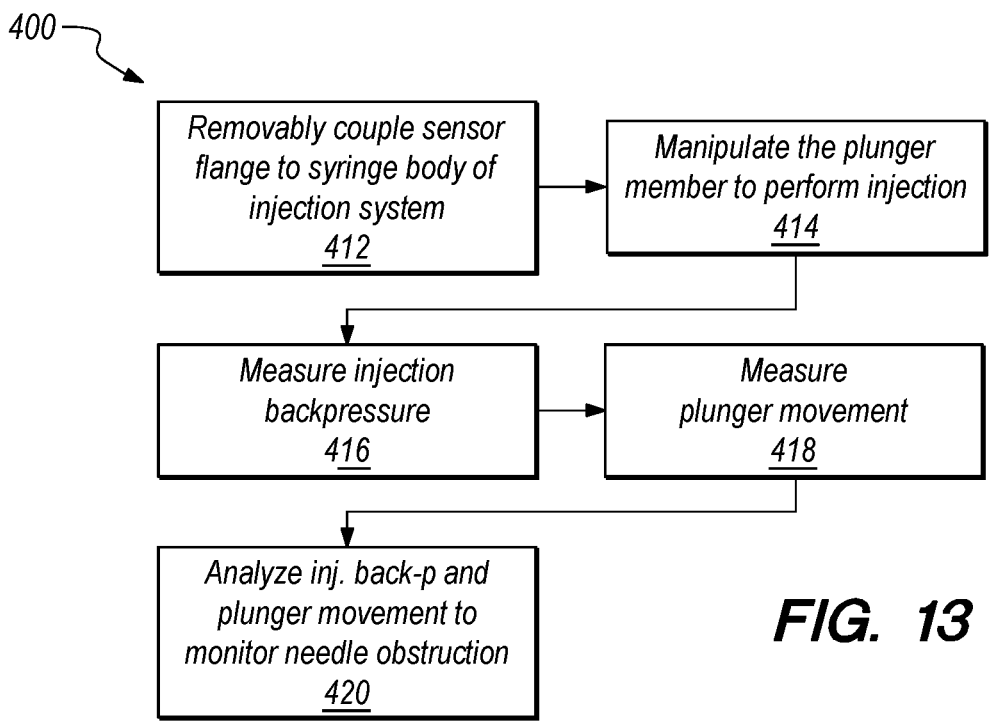

FIG. 13 depicts a method (400) of collecting injection information according to still another embodiment. At step (412), a sensor flange, such as the sensor flanges (150) described above, is removably coupled to the syringe body of injection system. The injection system may be similar or identical to the injection systems (110) described above. The sensor flange may be secured to the syringe body using an interference fit.

At step (414), the plunger member of the injection system is manipulated to perform the injection. For instance, force may be applied to a proximal end pad of the plunger member using a digit (e.g., a thumb) of a user's hand while one or more other digits of the user's hand provide an opposing force (e.g., against a distal side of the syringe flange or a sensor flange disposed thereon).

At step (416), the sensor flange measures an injection back pressure using a force sensor, as described above. For instance, the force sensor on the sensor flange may measure the proximally directed force on a surface (distal, proximal, interior, etc.) of the sensor flange, as the plunger member is moved into the syringe interior to perform the injection. The force on the sensor flange is approximately equal to the force applied to the plunger member at the stopper member attached thereto to perform the injection. In some embodiments, the force on the sensor flange is continuously measured in a force profile is generated and stored in a memory of the sensor flange.

At step (418), the sensor flange measures a plunger movement using a motion sensor, as described above. For example, the motion sensor may be an optical sensor, an IR sensor, an acoustic sensor, an ultrasound rangefinder, etc. The amount of motion (i.e., distance moved) detected the motion sensor can be combined with elapsed time from a clock in the sensor flange to derive a speed and an acceleration of the motion. In some embodiments the sensor flange continuously measures distance, speed, and/or acceleration of the plunger and stores the measured parameters in a memory of the sensor flange.

At step (420), the sensor flange (i.e., a processor therein) analyzes the injection back pressure and a plunger movement to monitor (i.e., detect) a needle obstruction event. For instance, the processor in the sensor flange can be programmed to detect a needle obstruction event if the injection backpressure increases while the plunger member motion is substantially stopped. A needle obstruction event may or may not be an injection error depending on the location of the plunger member during the needle obstruction event. For instance, at the end of an injection when the plunger member and the stopper member are at a distal end of the syringe interior, the force measured at the sensor flange (i.e., the injection backpressure) may increase with continued force applied by the user while the plunger member motion drops to essentially zero. Such a needle obstruction event is a normal part of the end of injection. On the other hand, if the needle obstruction event occurs before the plunger member has reached a full insertion depth, the needle obstruction event may be an injection error. In case, the needle obstruction event, its timing, and a position of the plunger member can be stored in a memory of the sensor flange. The sensor flange may also deliver an alarm signal (e.g., visible or audible) when a needle obstruction error event is detected to alert the user.

Figure 14A:
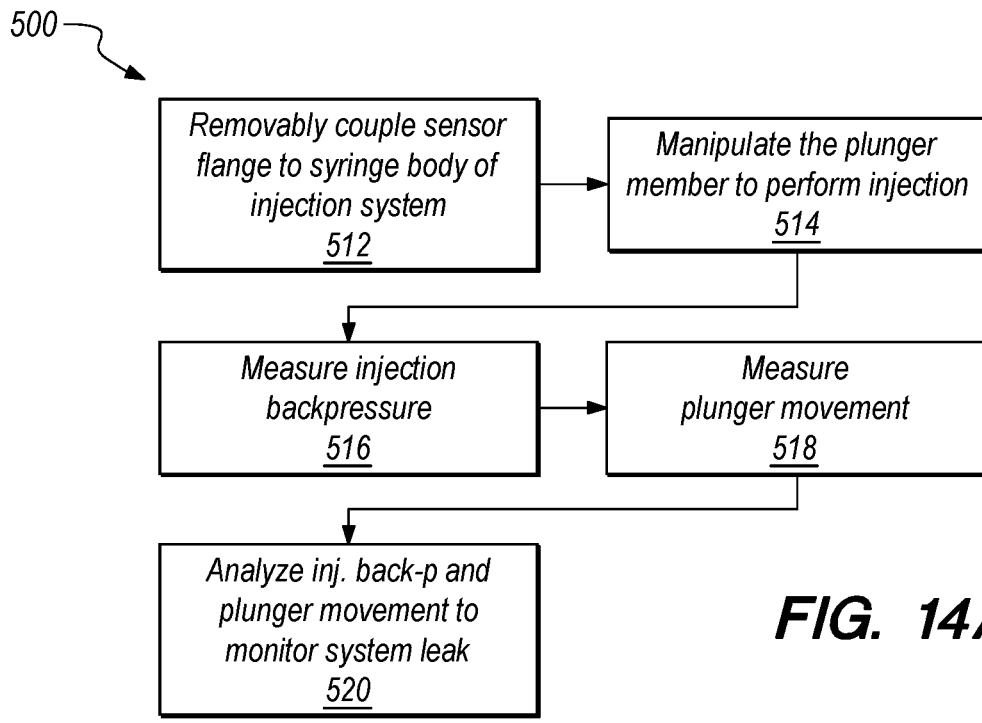

FIG. 14A depicts a method (500) of collecting injection information according to yet another embodiment. At step (512), a sensor flange, such as the sensor flanges (150) described above, is removably coupled to the syringe body of injection system. The injection system may be similar or identical to the injection systems (110) described above. The sensor flange may be secured to the syringe body using an interference fit.

At step (514), the plunger member of the injection system is manipulated to perform the injection. For instance, force may be applied to a proximal end pad of the plunger member using a digit (e.g., a thumb) of a user's hand while one or more other digits of the user's hand provide an opposing force (e.g., against a distal side of the syringe flange or a sensor flange disposed thereon).

At step (516), the sensor flange measures an injection back pressure using a force sensor, as described above. For instance, the force sensor on the sensor flange may measure the proximally directed force on a surface (distal, proximal, interior, etc.) of the sensor flange, as the plunger member is moved into the syringe interior to perform the injection. The force on the sensor flange is approximately equal to the force applied to the plunger member at the stopper member attached thereto to perform the injection. In some embodiments, the force on the sensor flange is continuously measured in a force profile is generated and stored in a memory of the sensor flange.

At step (518), the sensor flange measures a plunger movement using a motion sensor, as described above. For example, the motion sensor may be an optical sensor, an IR sensor, an acoustic sensor, an ultrasound rangefinder, etc. The amount of motion (i.e., distance moved) detected the motion sensor can be combined with elapsed time from a clock in the sensor flange to derive a speed and an acceleration of the motion. In some embodiments the sensor flange continuously measures distance, speed, and/or acceleration of the plunger and stores the measured parameters in a memory of the sensor flange.

At step (520), the sensor flange (i.e., a processor therein) analyzes the injection back pressure and a plunger movement to monitor (i.e., detect) a system leak event. For instance, the processor in the sensor flange can be programmed to detect a system leak event if the injection backpressure drops from a non-zero value to essentially zero while the plunger member moves distally. The system leak event, its timing, and its duration can be stored in a memory of the sensor flange. The sensor flange may also deliver an alarm signal (e.g., visible or audible) when a system leak event is detected to alert the user.

Figure 14B:
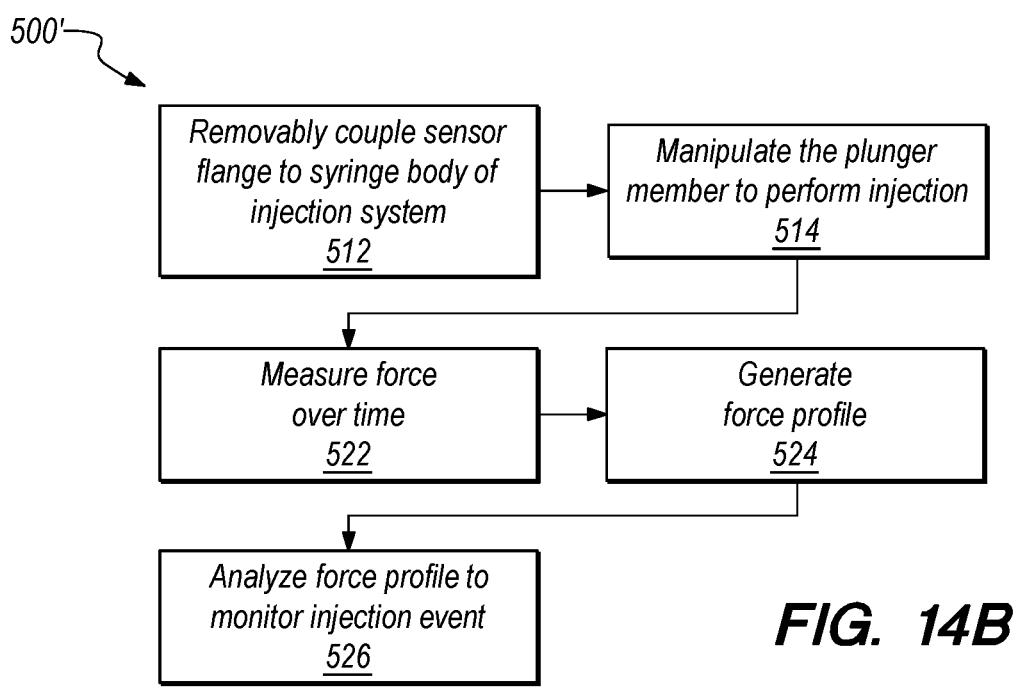

FIG. 14B depicts a method (500') of collecting injection information according to another embodiment. At step (512), a sensor flange, such as the sensor flanges (150) described above, is removably coupled to the syringe body of injection system. The injection system may be similar or identical to the injection systems (110) described above. The sensor flange may be secured to the syringe body using an interference fit.

At step (514), the plunger member of the injection system is manipulated to perform the injection. For instance, force may be applied to a proximal end pad of the plunger member using a digit (e.g., a thumb) of a user's hand while one or more other digits of the user's hand provide an opposing force (e.g., against a distal side of the syringe flange or a sensor flange disposed thereon).

At step (522), the sensor flange measures a force/injection back pressure using a force sensor, as described above. For instance, the force sensor on the sensor flange may measure the proximally directed force on a surface (distal, proximal, interior, etc.) of the sensor flange, as the plunger member is moved into the syringe interior to perform the injection. The force on the sensor flange is approximately equal to the force applied to the plunger member at the stopper member attached thereto to perform the injection. The difference in the method (500') depicted in FIG. 14B is that the force/injection back pressure is measured (e.g., continuously) over time. The difference in the method (500') depicted in FIG. 14B is that the force/injection back pressure is measured (e.g., continuously) over time.

At step (524), the sensor flange generates a force profile from the measured force/injection back pressure over time.

At step (526), the sensor flange (i.e., a processor therein) analyzes the force profile to monitor (i.e., detect) an injection event. For instance, the force profiles for various injection systems have characteristic "signature" shapes that reflect the physics of the injection systems. A typical injection event will begin with a high force "bump" as the stopper member friction is overcome. Then, the force will drop to a lower level as the stopper member glides and the injectable substance is forced out of the syringe interior. Finally, when the stopper member hits the bottom of the syringe body, there will be another lesser force "bump." The glide time is a function of the glide force. If the user is giving the injection quickly, the glide force will be higher and the injection time will be shorter. These relationships fall within known limits for each injectable substance and injection system combination. Errors can thus be detected. For example, injections in air will have a clearly different force profile signature than injections in tissue.

Figure 15:
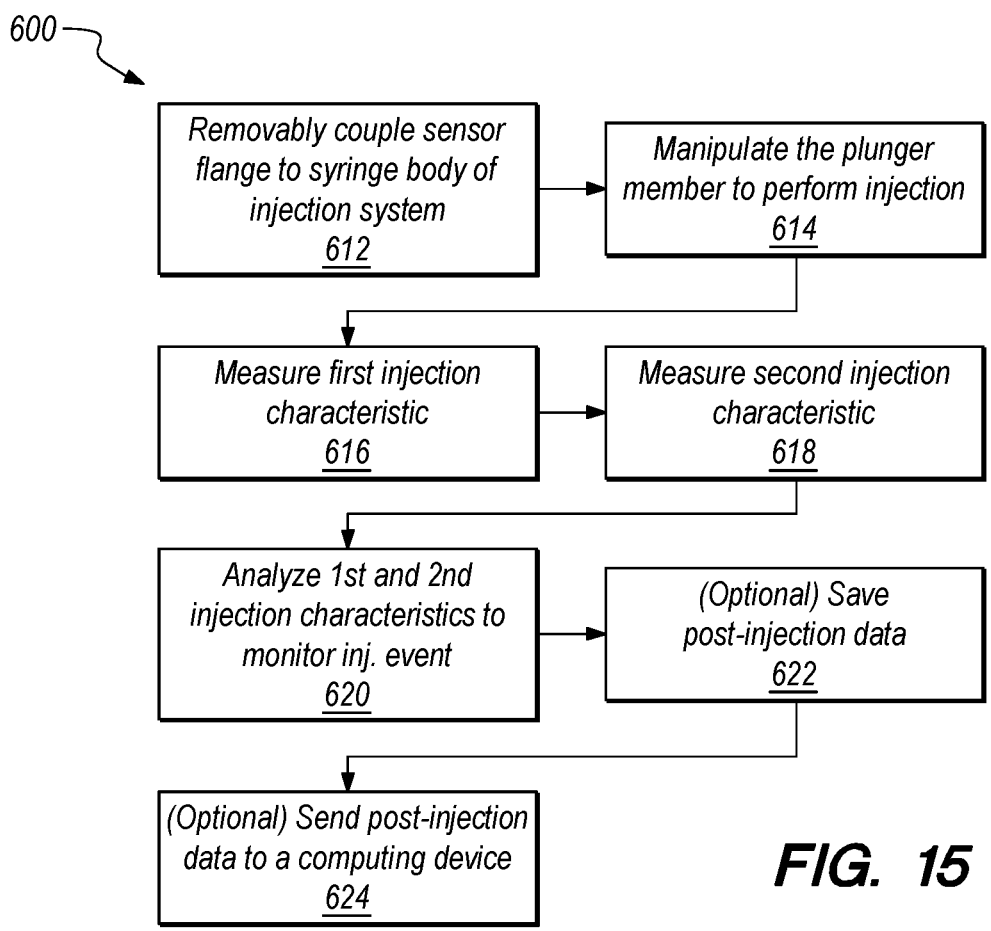

FIG. 15 depicts a method (600) of collecting injection information according to an embodiment similar to the one depicted in FIG. 11A. At step (612), a sensor flange, such as the sensor flanges (150) described above, is removably coupled to the syringe body of injection system. The injection system may be similar or identical to the injection systems (110) described above. The sensor flange may be secured to the syringe body using an interference fit.

At step (614), the plunger member of the injection system is manipulated to perform the injection. For instance, force may be applied to a proximal end pad of the plunger member using a digit (e.g., a thumb) of a user's hand while one or more other digits of the user's hand provide an opposing force (e.g., against a distal side of the syringe flange or a sensor flange disposed thereon).

At step (616), the sensor flange measures a first injection characteristic using a first sensor. Similarly, at step (618), the sensor flange measures a second injection characteristic using a second sensor. The first and second sensors may be any known type of sensor including, but not limited to, acoustic sensors, motion sensors, proximity sensors, temperature sensors, force sensors, accelerometer sensors, orientation sensors, sensor flange attachment ("mounting") sensors, and optical sensors. The first and second sensors may be the same type of sensor, or they may be different types of sensors. The types of sensors may be selected to measure the types of injection characteristics required by the method (600).

At step (620), the sensor flange (i.e., a processor therein) analyzes the first and second injection characteristics to monitor (e.g., detect, measure, determined, etc.) an injection event (e.g., completion of injection, plunger force, sheer force, injection error, etc.) The type of injection event monitored during the method (600) determines the types of injection characteristics measured in the types of sensors in the sensor flange.

At optional step (622), the sensor flange stores post-injection data in a memory of the sensor flange. Post-injection data includes, but is not limited to, the measured first and second injection characteristics, data relating to the monitored injection event, injection date and time, injection frequency, plunger force, injection elapsed time, injection error related data, viscosity, temperature, warming time, shear force, residual drug remaining in the syringe, multiple injection site regimen data, reward program data, and educational/marketing data. Injection errors include, but are not limited to, drug identity error, injection timing error, dosage error, shear force error, de-bubbling error, residual drug remaining in the syringe, and multi-site injection error.

At optional step (624), the sensor flange sends the post-injection data to a computing device. Sensor flange can communicatively couple to the computing device using various communication devices, which may be wired and/or wireless. Wireless communication devices include, but are not limited to, Bluetooth, WiFi, WiFi Direct, cellular, and near field communications. After the sensor flange establishes a communication link with a computing device, the sensor flange may download the post-injection data to the computing device. In one embodiment, the sensor flange stores measured, collected, calculated, and generated post-injection data in a memory then downloads the post-injection data in a batch to a computing device (e.g., a user's smartphone or a computing device at a pharmacy).

Figure 16:
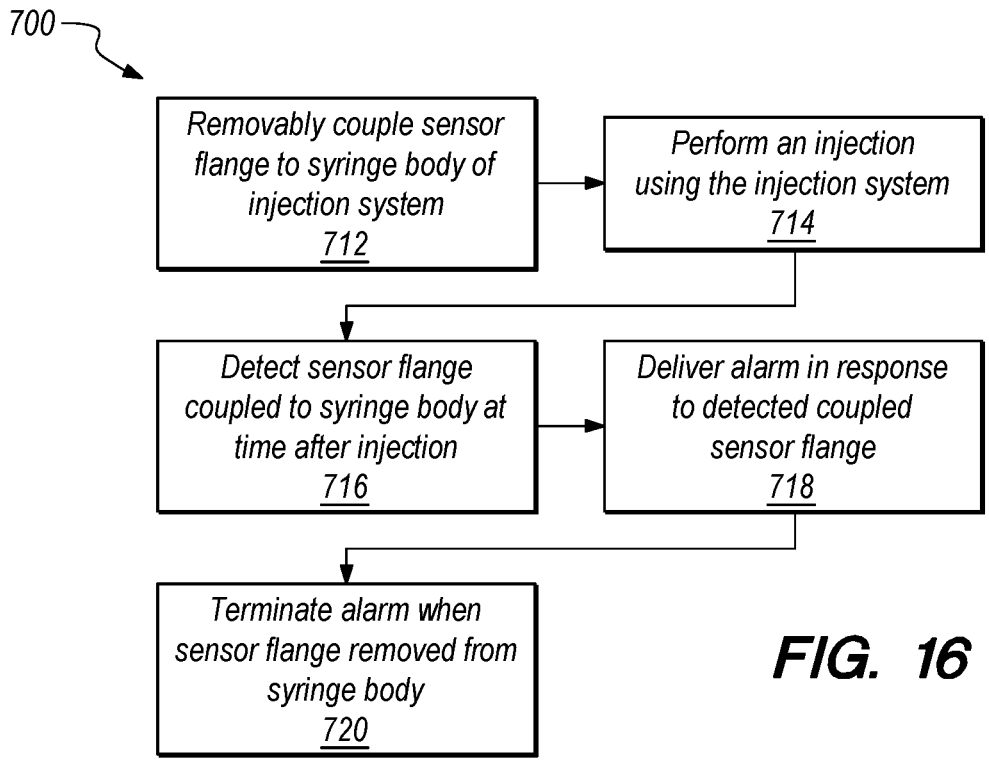

FIG. 16 depicts a method (700) of collecting injection information according to another embodiment. At step (712), a sensor flange, such as the sensor flanges (150) described above, is removably coupled to the syringe body of injection system. The injection system may be similar or identical to the injection systems (110) described above. The sensor flange may be secured to the syringe body using an interference fit.

At step (714), an injection is performed using the injection system. For instance, the plunger member of the injection system may be manipulated to perform the injection. For instance, force may be applied to a proximal end pad of the plunger member using a digit (e.g., a thumb) of a user's hand while one or more other digits of the user's hand provide an opposing force (e.g., against a distal side of the syringe flange or a sensor flange disposed thereon).

At step (716), the sensor flange detects that the sensor flange remains coupled to the syringe body at a pre-determined time after the injection is performed. In some embodiments the pre-determined time is one, two, or three minutes. Sensor flange can detect that it is coupled to the syringe body using a mounting sensor, which may include a mechanical switch that is depressed when the sensor flange is coupled to the syringe body. The sensor flange remaining coupled to the syringe body after an injection is completed is consistent with the situation in which a user has forgotten to remove the sensor flange from the syringe body. This, in turn, can lead to the sensor flange being disposed along with the used syringe body. Unintentional disposal of the syringe flange can result in loss of post-injection data and valuable equipment.

At step (718), the sensor flange delivers an alarm signal in response to the detected couple sensor flange. The alarm may be an audible alarm and/or a visible alarm. In another embodiment, the sensor flange may communicate with a mobile computing device (e.g., a mobile phone) to sound an alarm, or alert messages on the computing device. In another embodiment, the sensor flange may cooperate with a sharps disposal container that will not open for disposal of a used syringe body in the proximity of the sensor flange, thereby forcing the user to remove the sensor flange before disposing of the used syringe body.

At step (720), the sensor flange terminates delivery of the alarm signal in response to detecting that the sensor flange has been removed from the syringe body. For instance, the removing the sensor flange from the syringe body (34) may allow a mechanical switch to move into its spring-biased "out" position to indicate to the sensor flange that it is no longer coupled to the syringe body. The alarm signal, its cause, and its timing can be saved to a memory of the sensor flange.

Figure 17:
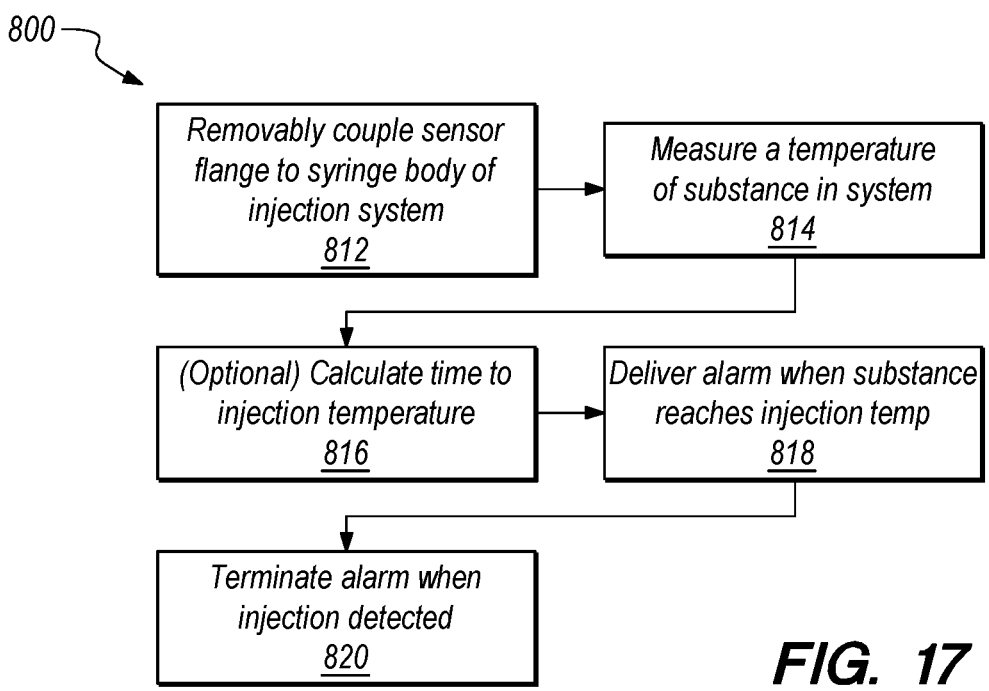

FIG. 17 depicts a method (800) of collecting injection information according to yet another embodiment. At step (812), a sensor flange, such as the sensor flanges (180) described above, is removably coupled to the syringe body of injection system. The injection system may be similar or identical to the injection systems (110) described above. The sensor flange may be secured to the syringe body using an interference fit.

At step (814), the sensor flange measures a temperature of an injectable substance in the syringe interior of the injection system. The sensor flange may include a temperature sensor including, but not limited to, an infrared thermometer and a thermocouple. While the temperature sensor may not directly measure the temperature of the injectable substance, the sensor flange (i.e. a processor therein) may extrapolate the temperature of the injectable substance from a measured temperature (e.g., of the exterior of the syringe body).

At step (816), a processor in the sensor flange calculates a time until the injectable substance reaches a proper temperature for injection. The processor may use the measured or extrapolated current temperature of the injectable substance, a measured room temperature, and information about the proper temperature for injection to calculate the time until injection.

At step (818), the sensor flange delivers an alarm signal in response to the injectable substance in the syringe interior reaching the proper temperature for injection. The alarm signal may be an audible alarm and/or a visible alarm. The sensor flange may detect when the injectable substance reaches the proper temperature for injection using the temperature sensor. Alternatively, the sensor flange may deliver alarm signal after the time until injection calculated in step (816) has expired.

At step (820), the sensor flange terminates delivery of the alarm signal in response to detecting that an injection has been completed. The sensor flange may detect that injection has been completed using any of the methods described herein.

In some embodiments, the sensor flange may receive injection setup data from a computing device through a communication connection before injection. The communication connection may be wired and/or wireless as described above. The injection setup data includes, but is not limited to, current date and time, first injection date and time, injection frequency, syringe type, viscosity, temperature, warming time, maximum shear force, multiple injection site regimen data, reward program data, and educational/marketing data. The injection setup data can be used to prepare the injection system for injection and collection of post-injection data.

In some embodiments, the sensor flange may have a clock and the processor in the sensor flange may be programmed to instruct an output device in the sensor flange to deliver an alarm signal when the clock reaches a pre-determined injection time (which may be received as injection setup data). The alarm signal may be an audible alarm and/or a visible alarm. The audible alarm may be a simple repeating tone (e.g., beeping), a tone the changes pitch, a computer-generated voice, a previously recorded voice, etc. The visible alarm may be binary (on and off lights), a light that changes color, textural, icons, etc. The processor in the sensor flange may be programmed to terminate delivery of the alarm signal when the sensor flange is coupled to the syringe body. The processor in the syringe flange may also be programmed to terminate delivery of the alarm signal after a pre-determined time and resume delivery after another pre-determined time. After still another pre-determined time, the processor in the syringe flange may be programmed to deliver a missed dose message.

In some embodiments, the sensor flange may have a power source to provide power to its various components. The power source may be a battery. In other embodiments the power source is self-generating using the injection motion provided by the user. After a pre-determined time with the sensor flange in an uncoupled state, the processor may be programmed to place the sensor flange in a low-power mode. In one embodiment the low-power mode includes deactivating power to the output device and the wireless communication device, and intermittently powering a mounting sensor to detect whether the sensor flange has been mounted to a syringe body.

In some embodiments, the processor in the sensor flange is programmed to calculate the shear force on injectable substance in the syringe interior. For instance, the shear force may be calculated from injection back pressure and a plunger member movement. In such embodiments, if the calculated shear force exceeds a maximum shear force (which may have been downloaded as injection setup data), processor in the syringe flange may instruct an output device to deliver an alarm signal (for instance instructing the user to reduce the speed of the plunger member).

In some embodiments, the processor in the sensor flange is programmed to instruct an output device to deliver alarm signals (i.e., speed and alerts) when the speed of the plunger member is outside of the pre-determined range (which may have been downloaded as injection setup data). In such embodiments, the alarm signals may include a speed up and a slowdown message depending on the plunger member speed error detected by the motion sensor as described above.

In some embodiments, the processor in the sensor flange is programmed to deliver multi-site dosing messages when an injection completion is detected as described above. Multi-site dosing messages include instructions to move to the next site, and instructions that the multi-site dosing regimen is completed. Instructions can also be given for single-site dosing.

In some embodiments, the sensor flange may be used with multi part medicines using a dual chamber mixing and injection system such as those described in U.S. patent application Ser. Nos. 62/431,382 and 15/801,259. The contents of U.S. patent application Ser. No. 62/431,382 have been incorporated herein by reference. The contents of U.S. patent application Ser. No. 15/801,259 are fully incorporated herein by reference as though set forth in full. The sensor flange may be used to direct the user as to proper injection technique by monitoring plunger rod position, velocity, or acceleration and sounding an alarm if the mixing and/or injection is occurring too fast or too slow.

In some embodiments, the sensor flange includes an acoustic sensor that is configured to detect a sound associated with completion of an injection. In such embodiments, the processor in the sensor flange is programmed to record injection completion when the acoustic sensor detects the sound.

While the clock in the sensor flange (150) has been described as enabling the measurement of a change in position over time (velocity) and/or a change in velocity over time (acceleration) of the plunger rod (116) relative to the sensor flange (150), in other embodiments, the clock can also enable measurement of changes in other injection characteristics over time. For instance, a clock can enable the measurement/calculation of changes in force/pressure, temp, etc. over time.

Figure 30:
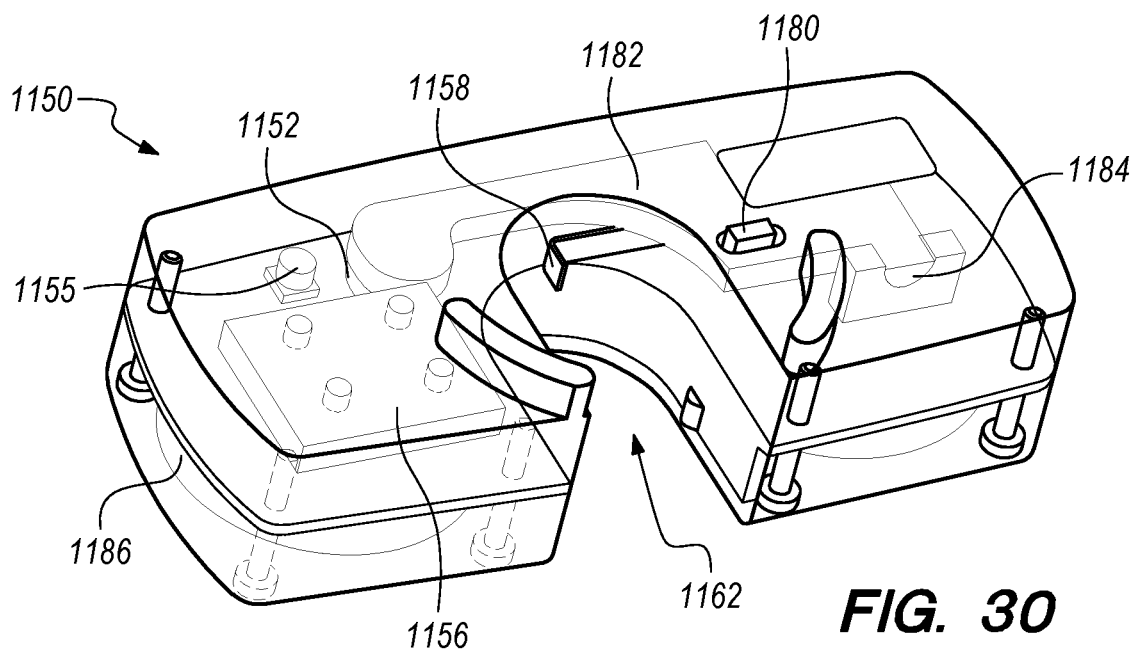
FIG. 30 illustrates a sensor flange according to another embodiment.

FIG. 30 depicts a sensor flange (1150) according to another embodiment. The sensor flange (1150) is similar to the sensor flange (150) depicted in FIGS. 6, 7, 10B-10F. The sensor flange (1150) includes a flange force sensor (1152), a pair of output devices (1155, 1156), an opening (1162), and a mounting sensor (1158) disposed adjacent to the opening (1162).

The sensor flange (1150) is designed to mount on to a syringe body (112, see FIGS. 6-7 and their description above) in a similar manner and the sensor flange (150) in FIGS. 6-7. The sensor flange (1150) is designed to clip onto a syringe body (112) while being able to slide freely along a longitudinal axis of the syringe body (112) until a load point (1180) on the flange force sensor (1152) on the sensor flange (1150) contacts the syringe flange (126, see FIGS. 6-7). When load point (1180) contacts the syringe flange (126), the force applied to the proximal end pad (132) is transmitted to the load point (1180) by movement of the syringe flange (126) against the sensor flange (1150), which is held stationary by the user's fingers. The load point (1180) is mechanically coupled to the force sensor (1152) by a lever (1182), which pivots about a pivot point (1184). Because the load point (1180) is approximately ⅓ of the distance between the pivot point (1184) and far end of the lever (1182) that overlies the force sensor (1152), transmitting the force through the load point (1180) and the lever (1182) to the force sensor (1152) reduces the force applied to the force sensor (1152) (e.g., by approximately ⅓). This configuration allows use of off-the-shelf force sensors (1152), which may not have the appropriate sensitivity for this sensor flange (1150), by attenuating the force delivered to the force sensor (1152). While the sensor flange (1150) depicted in FIG. 30 includes a lever (1182) to attenuate the force delivered to the force sensor (1152), other sensor flanges (not shown) may include force sensors directly under the load point.

In some embodiments, the force sensor (1152) measures a force/pressure applied to a proximal end pad (132, see FIGS. 6-7) and mechanically transmitted to the force sensor (1152) as a resistance/impedance, which can be processed, stored, and/or transmitted as a numerical data point. The sensor flange (1150) includes a processor (not shown) that may calculate the flow over time in the injection system (110, see FIGS. 6-7) using, in some embodiments, the Hagen-Poiseuille equation and a measured force: $\Delta P = 8 \mu L Q / \pi R^4$, where $\Delta P$ is the pressure difference between the two ends of the tube, p is the dynamic viscosity of the liquid being injected through the tube, L is the tube length (e.g., the length of the needle), R is the tube radius (e.g., the radius of the needle), and Q is the flow rate of the liquid through the tube. Because $\Delta P$=force ("F") over syringe cross sectional area ("A") and Q=dose ("D") over time ("t"), the formula can be expressed as $\Delta P = AD8 \mu L / \pi R^4 t$. Because A, D, p, L, and R are constant for a given dose with a given injection system, $AD8 \mu L / \pi R^4$ can be represented by a contant k. Accordingly, for two users injecting the same dose using the same injection system at different speeds, $F_1 = k/t_1$ and $F_2 = k/t_2$. In other words, F×t is constant (i.e., =k) for injecting the same dose using the same injection system. Therefore, $F_1 \times t_1 = F_2 \times t_2$, and doubling the force will halve the injection time.

Figure 31:
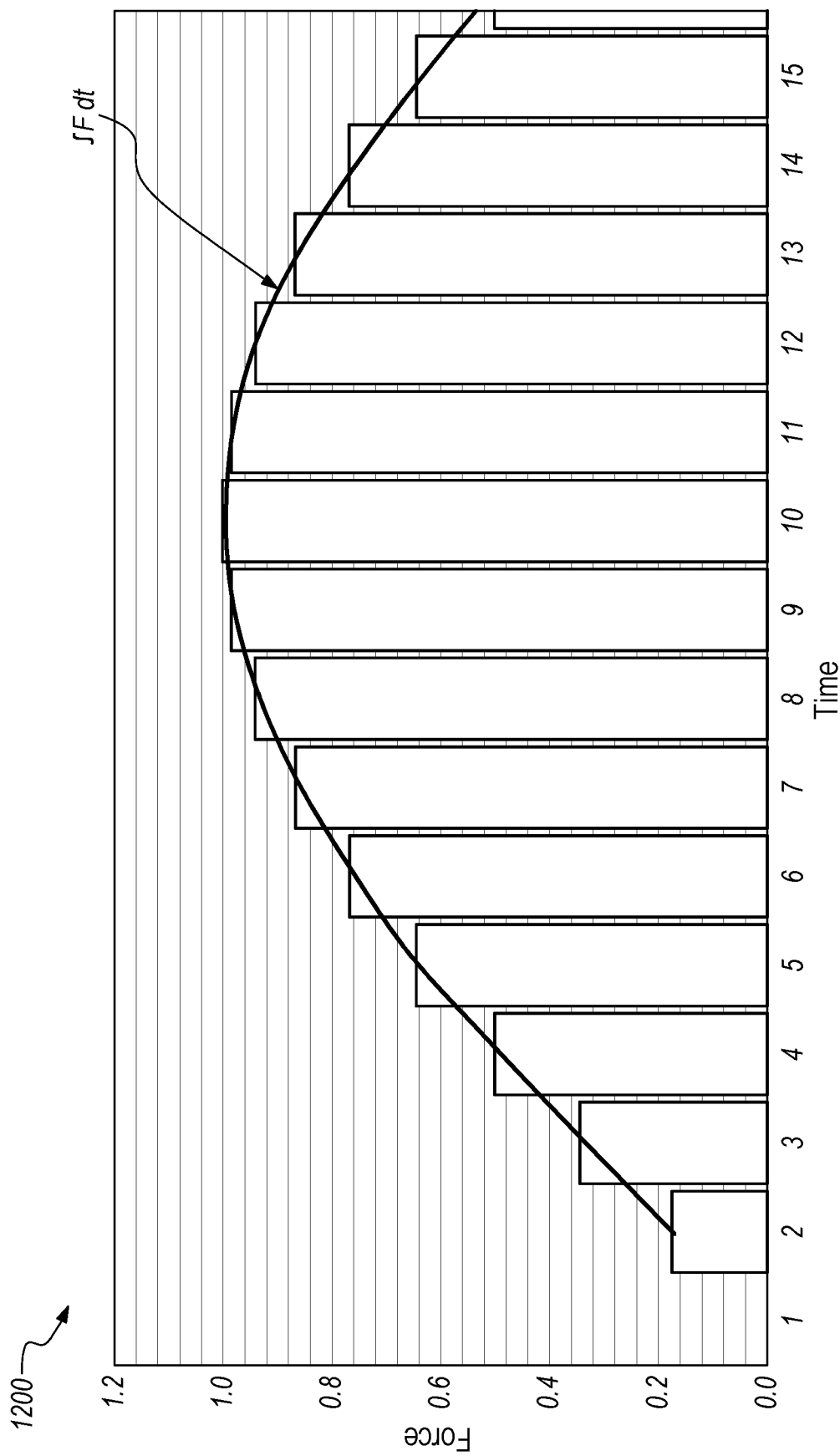
FIG. 31 is a graph illustrating force vs. time for an injection according to one embodiment.

Because a human user may not be able to apply a constant force to the injection system (110), the processor in the sensor flange (1150) may be configured to calculate F×t over a short injection interval during which the force is approximately constant. FIG. 31 depicts such a series of measurements in a graph 1200. By integrating the F dt, the injection force can be approximated and F×t can be calculated using a known cumulative sampling time.

Figure 32:
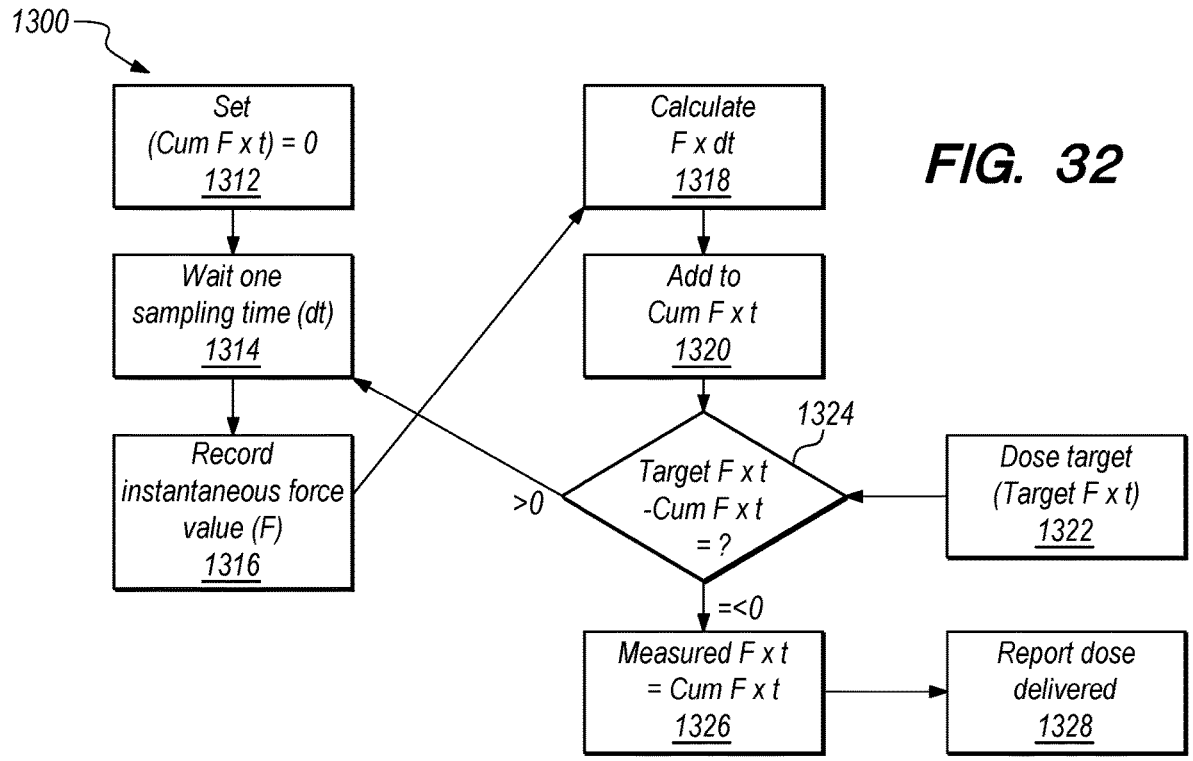
FIG. 32 illustrates a method for determining completion of injection of a given dose using an injection system according to one embodiment.

FIG. 32 depicts a method (1300) for determining completion of injection of a given dose using a given injection system according to one embodiment. At step (1312), the processor in the sensor flange (1150) and/or the processor in an external computer (e.g., smart phone) communicatively coupled to the sensor flange (1150) sets a cumulative F×t to 0. At step (1314), the processor waits for one known sampling time (dt). At step (1316), the force sensor (1152) in the sensor flange (1150) measures/records the instantaneous force (F). At step (1318), the processor calculates F×dt, and at step (1320), the processor adds the calculated F×dt to the cumulative F×t. At step (1322), which may not necessarily occur after step (1320), but occurs before decision point (1324), described below, the processor either determines or is provided with a dose target (i.e., target F×t). The target F×t is determined using the known A, D, p, L, and R of the injection system (110). The target F×t may also be affected by the friction between the stopper member (114) and the syringe body (112). At decision point (1324), the processor calculates the difference between the target F×t and the cumulative F×t. If the difference is less than zero (i.e., the cumulative F×t has yet to reach the target F×t), the method (1300) returns to step (1314) Ward waits another sampling time (dt). If the difference is equal to or greater than zero (i.e., the cumulative F×t has reached or surpassed the target F×t), the method (1300) proceeds to step (1326) where the processor sets a measured F×t is equal to the cumulative F×t. At step (1328), the processor reports that the dose has been delivered. The dose delivery can be reported to a health care professional, a home injection patient, an electronic medical record, a smartphone application, a doctor, a nurse, a caregiver, a medical insurer, a clinical trial, a clinical trial administrator, a pharmaceutical distribution company, a pharmaceutical manufacturer, etc.

The method (1300) described above determines completion of a dose delivery using, among other system characteristics, the needle gauge (A and R) and length (L). The needle gauge and length can be inputted into processor by the user or caregiver (e.g., via a smart phone). Alternatively, the processor can experimentally determine k=F×t during a first use of the injection system (110). A table of common needle sizes, which can be stored in processor, can facilitate this determination. In other embodiments, the calibration to be manually triggered by a user to capture the needle gauge and length, drug viscosity, dose, and/or other force sensor properties.

Figure 33:
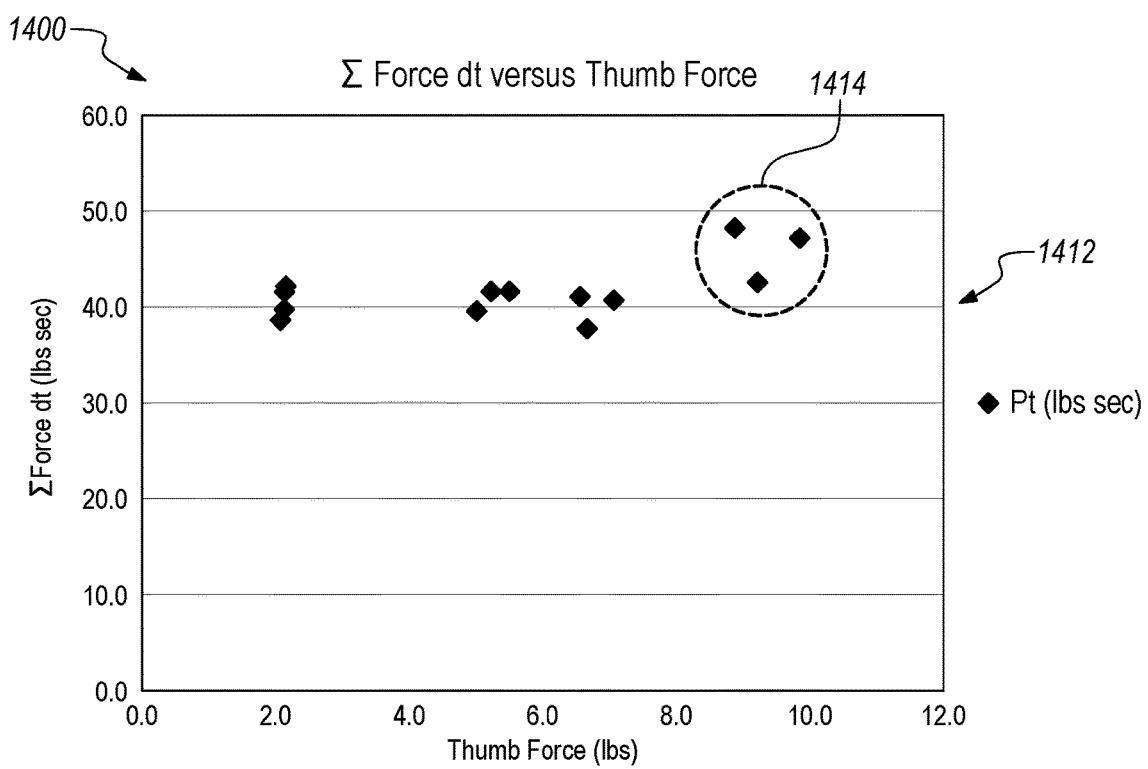
FIG. 33 is a graph illustrating forcext vs. thumb force for injections according to various embodiments.

The method (1300) described above determines completion of a dose delivery using the Hagen-Poiseuille equation, which is more accurate with nonturbulent flow needle. Accordingly, the sensor flange (1150) may be configured to detect/calculate injection characteristics indicative of turbulent flow. FIG. 33 is a graph (1400) of the sum of F dt versus the force applied to the system (i.e., "Thumb Force") for the injection of 1 cc (e.g., mL) of liquid through a 27 gauge needle that is half an inch long. The graph (1400) shows that for Thumb Forces less than about 9 lbs., 40 lb-sec (1412) is required to complete a 1 cc injection. However, for Thumb Forces greater than about 9 lbs. (1414), more than 40 lb-sec (1412) is required to complete a 1 cc injection. Accordingly, processor may utilize a calculated instantaneous F×t (e.g., as shown in method (1300)) to determine when the Thumb Force is so high that flow has become turbulent. In response, the sensor flange (1150) may indicate, using either visual or audio indicators, that the user should reduce the Thumb Force to maintain nonturbulent flow and accuracy of the dose completion method (1300).

The output devices (1155, 1156) communicate with (e.g., deliver various messages, signals, and/or alarms to) a user. The sensor flange (1150) includes a display (1155) to communicate visually with the user. The display (1155) may communicate with a binary (i.e., on/off) signal, a color signal, etc. In other embodiments, the display function is performed by text an image capable display. The sensor flange (1150) also includes a speaker (1156) to communicate aurally with the user. The speaker (1156) may communicate with a binary (i.e., beep) sound, a tonal sound, a spoken textual signal/message (e.g., using a pre-recorded and/or computer generated voice), etc. While the output devices (1155, 1156) are described as a display and/or a speaker, various other output devices (e.g., haptic, etc.) can also be used with sensor flange is according to other embodiments. The sensor flange (1150) also has a battery (1186) (e.g., an inductively rechargeable battery) to power the various electrical components thereof.

The mounting sensor (1158) may be a partially mechanical device (e.g., a switch) that has two states. The mounting sensor (1158) has an "uncoupled" state where the mounting sensor (1158) is not depressed and extends from the surface of the sensor flange (1150) due to a bias (e.g., driven by a spring). The mounting sensor (1158) also has a "coupled" state where the mounting sensor (1158) is depressed by interaction with the outer surface of the syringe body (112) disposed in the opening (1162). The depressed mounting sensor (1158) sends a message to a processor (not shown) in the sensor flange (1150) to communicate that the sensor flange (1150) is removably coupled to the syringe body (112).

While the sensor flange (1150) depicted in FIG. 30 requires information regarding the injection system (110), other injection systems can determine completion of dose delivery with less information regarding the systems. For instance, the optical motion sensor (160) describe above with reference to FIGS. 6-7 may include optics configured to detect and quantify movement of the plunger member (116). In some embodiments, the distance moved by the plunger member (116) is summed, and when the summed distance reaches approximately a target distance (i.e., the distance sufficient for the stopper member (114) to reach the distal end (122) of the syringe body (112)), the sensor flange (150) determines that a full dose has been delivered. In this embodiment, the only information regarding the injection system (110) required for dose delivery determination is the distance from the stopper member (114) to the distal end (122) of the syringe body (112).

Figure 34:
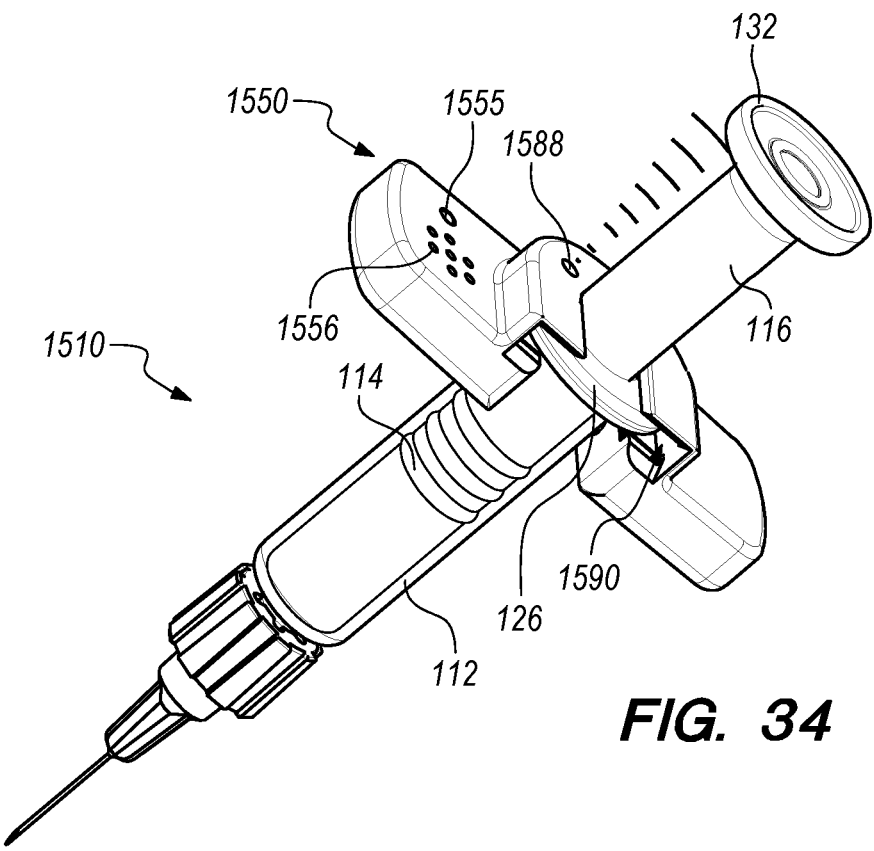
FIG. 34 illustrates a sensor flange according to still another embodiment.

FIG. 34 depicts an injection system (1510) according to another embodiment that also determines dose delivery completion using a distance traveled by the stopper member (114) and the plunger member (116) coupled thereto. The injection system (1510) includes a sensor flange (1550) having a sonic echo sensor (1588) like the one (160) depicted in FIG. 9. The sonic echo sensor (1588) is configured to measure the distance between the sonic echo sensor (1588) and the proximal end pad (132) coupled to the plunger member (116). When the distance between the sonic echo sensor (1588) and the proximal end pad (132) reaches approximately a target distance (i.e., the distance sufficient for the stopper member (114) to reach the distal end (122) of the syringe body (112)), the sensor flange (1550) determines that a full dose has been delivered. In this embodiment, the only information regarding the injection system (110) required for dose delivery determination is the distance from the stopper member (114) to the distal end (122) of the syringe body (112). Alternatively, the sonic echo sensor (1588) can be aimed into the syringe body (112) to determine the distance to the stopper member (116). Alternatively, the function of the sonic echo sensor (1588) may be performed by a laser range finder, a digital camera with auto focus capability, or other methods of determining the position of the plunger member (114) and/or stopper member (116) over time.

The sensor flange (1550) also includes a slot (1590) configured to securely accept the syringe flange (126) of the syringe body (112) to fix the sonic echo sensor (1588) relative to the syringe body (112). The sensor flange (1550) also includes a display (1555) and a speaker (1556), which function as output devices as described above.

Figure 35:
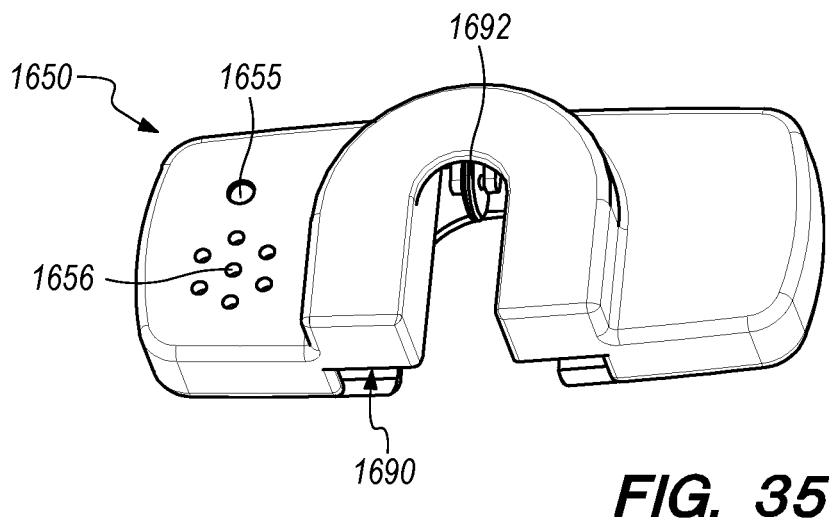
FIGS. 35 and 36 illustrate a sensor flange (FIG. 35) removably coupled to an injection system (FIG. 36) according to yet another embodiment.
Figure 36:
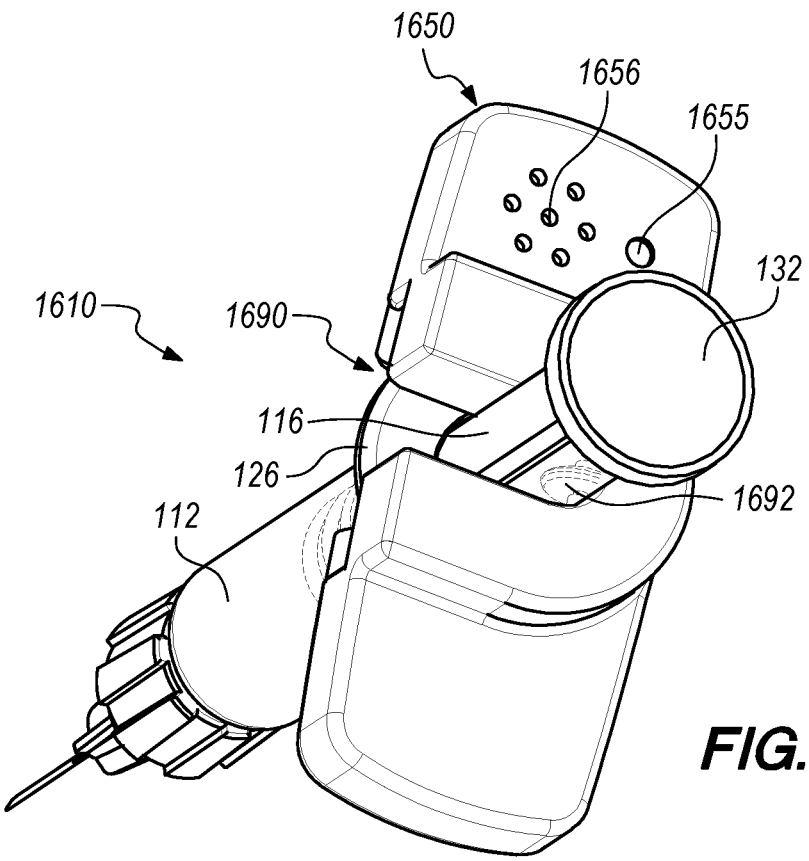
Figure 37:
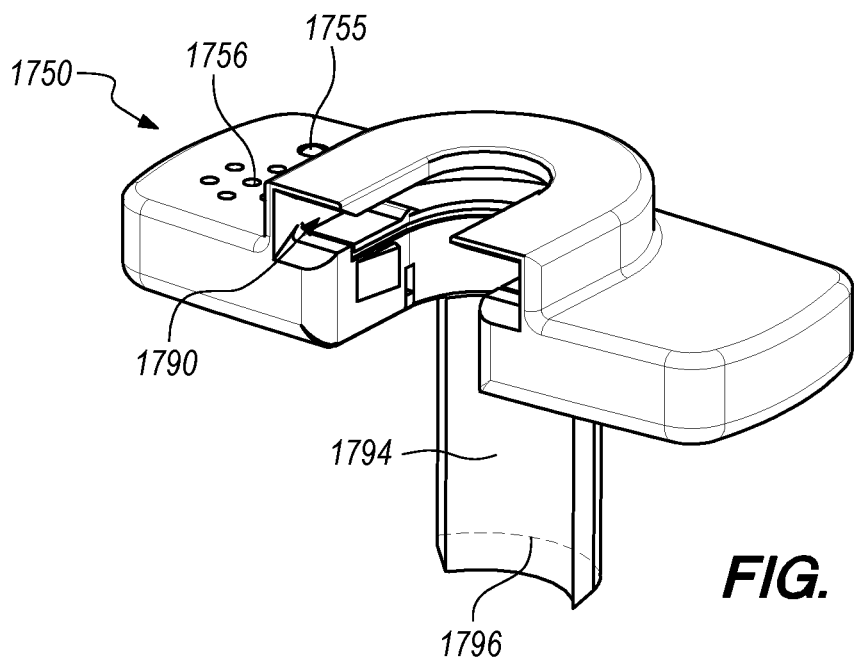
FIGS. 37-40 illustrate a sensor flange (FIGS. 37 and 38) removably coupled to an injection system (FIGS. 39 and 40) according to another embodiment.

FIGS. 35 and 36 depict an injection system (1610) according to still another embodiment that also determines dose delivery completion using a distance traveled by the stopper member (114) and the plunger member (116) coupled thereto. The injection system (1610) includes a sensor flange (1650) having a roller sensor (1692) configured to measure a distance traveled by the plunger member (116). The sensor flange (1650) also includes a slot (1690), (1655), and a speaker (1656), which are similar to the corresponding components depicted in FIG. 34 and described above.

The roller sensor (1692) contacts the plunger member (116) when the sensor flange (1650) is mounted on the syringe body (112) with the syringe flange (126) in the slot (1690). As such, movement of the plunger member (116) causes rotation of a wheel in the roller sensor (1692). An optical reader or a mechanical sensor in the roller sensor (1692) measures rotation of the wheel therein, and a processor in or coupled to the sensor flange (1650) determines distance moved by the plunger member (116) from the measured rotation of the wheel. While the roller sensor (1692) depicted in FIG. 36 is configured for use with a plunger member (116) having an "X" cross-section, other roller sensors may be configured for use with plunger members having other cross-sections.

FIGS. 37-40 depict an injection system (1710) according to yet another embodiment that also determines dose delivery completion using a distance traveled by the stopper member (114) and the plunger member (116) coupled thereto. The injection system (1710) includes a sensor flange (1750) having a light sensor (1798) and a light guiding optical element ("light pipe") (1794) configured to determine when a stopper member (114) intersects a light beam emitted by the light sensor (1798) and traveling through the light pipe (1794). The sensor flange (1750) also includes a slot (1790), (1755), and a speaker (1756), which are similar to the corresponding components depicted in FIG. 34 and described above.

Figure 39:
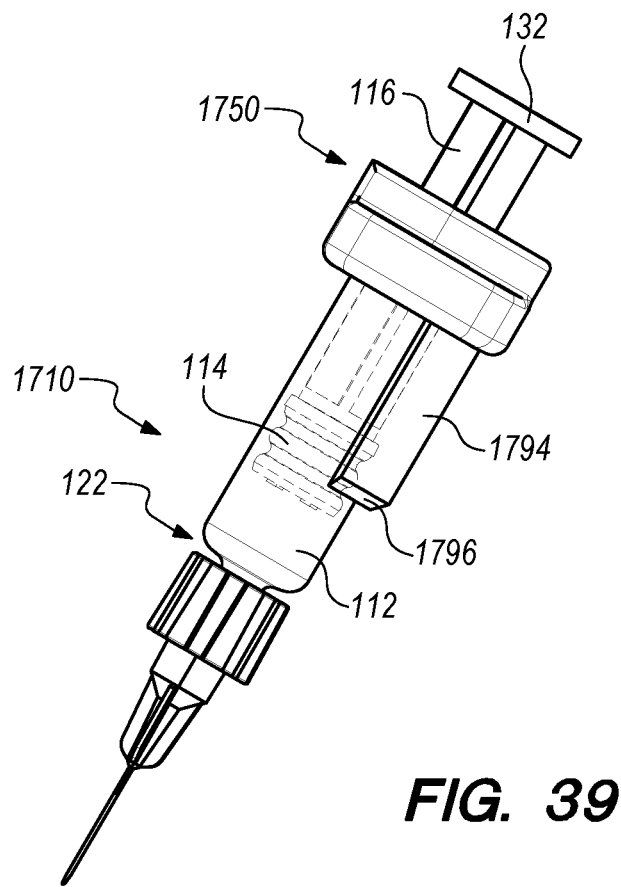
Figure 40:
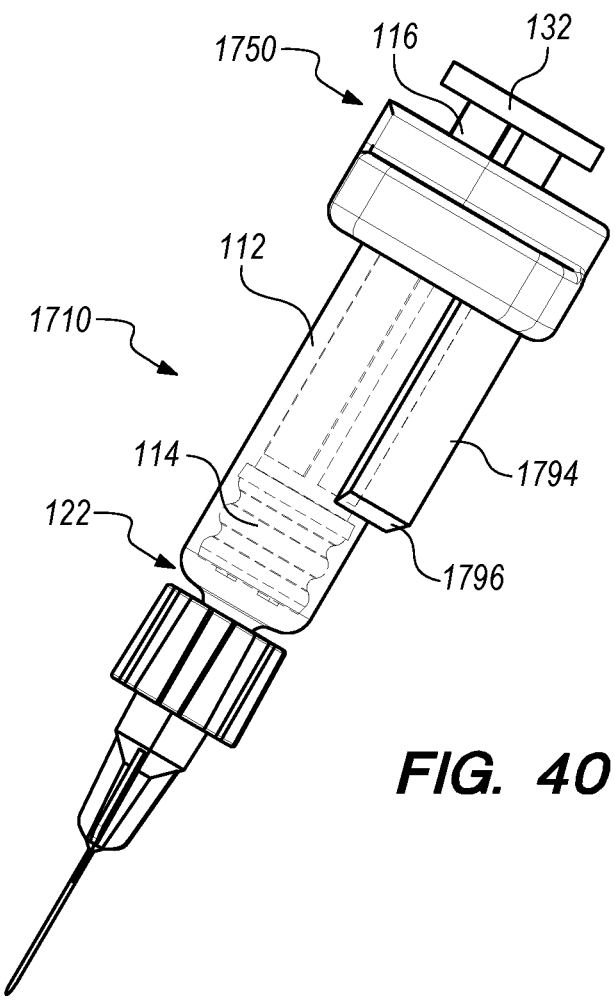

The light sensor (1798) includes a light emitter and a light receiver, and is optically coupled to the light pipe (1794). The light pipe (1794) includes a beveled reflective surface (1796) configured to guide light in a direction orthogonal to the longitudinal axis of the syringe body (112). The light sensor (1798) and the light pipe (1794) are configured such that light from the light emitter in the light sensor (1798) is directed into the syringe body (112) and the emitted light reflected by the syringe body (112) and the liquid contained therein is detected by the light receiver in the light sensor (1798). As shown in FIG. 39, in the pre-injection configuration, a stopper member (114) is disposed in the light path defined by the beveled reflective surface (1796). The dark stopper member (114) reduces the reflected light reaching the light receiver in the light sensor (1798). In contrast, in the post-injection configuration depicted in FIG. 40 (i.e., wherein the stopper member (114) has reached the distal end (122) of the syringe body (112)) the stopper member (114) has moved beyond the light path defined by the beveled reflective surface (1796). As such, the amount of reflected light reaching the light receiver in the light sensor (1798) is increased in the post-injection configuration. The processor in or coupled to the sensor flange (1750) can determine that the injection is complete based on this change in the intensity of reflected light.

Figure 41:
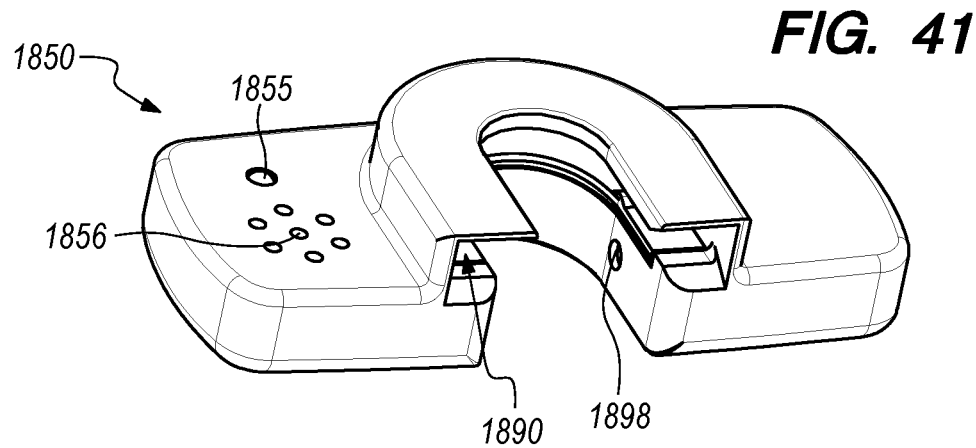
FIGS. 41-43 illustrate a sensor flange (FIG. 41) removably coupled to an injection system (FIGS. 42 and 43) according to still another embodiment.
Figure 42:
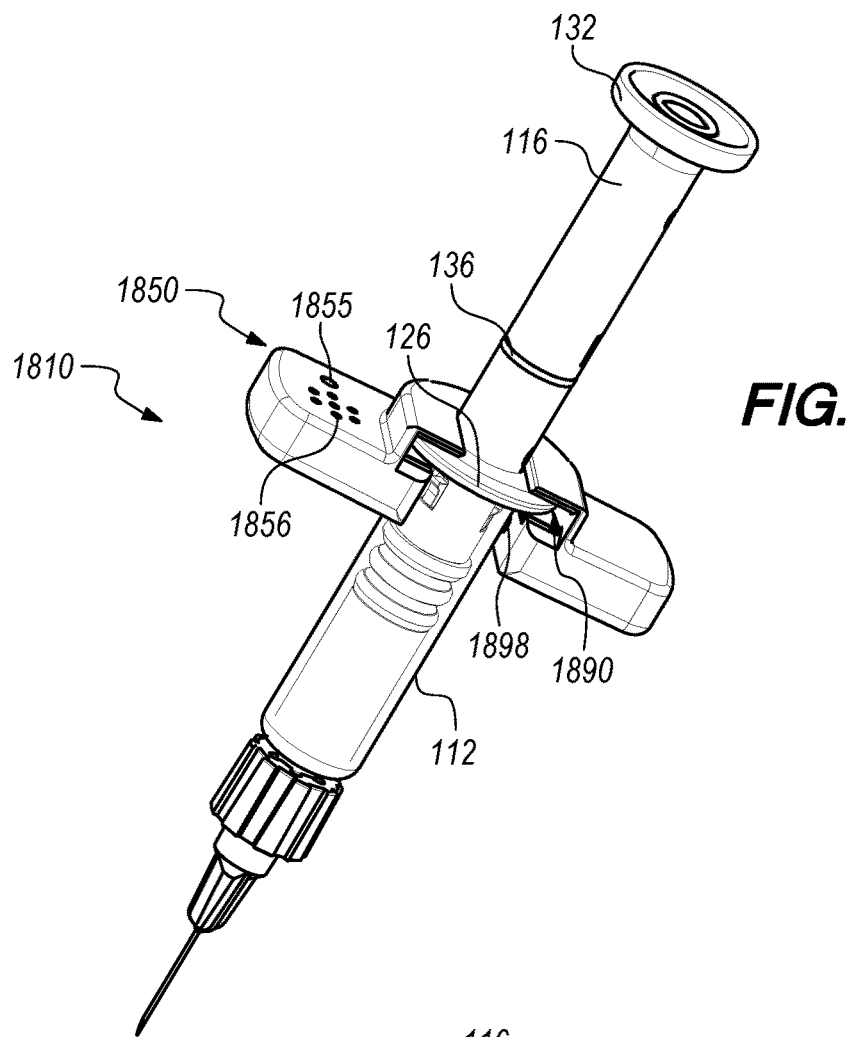
Figure 43:
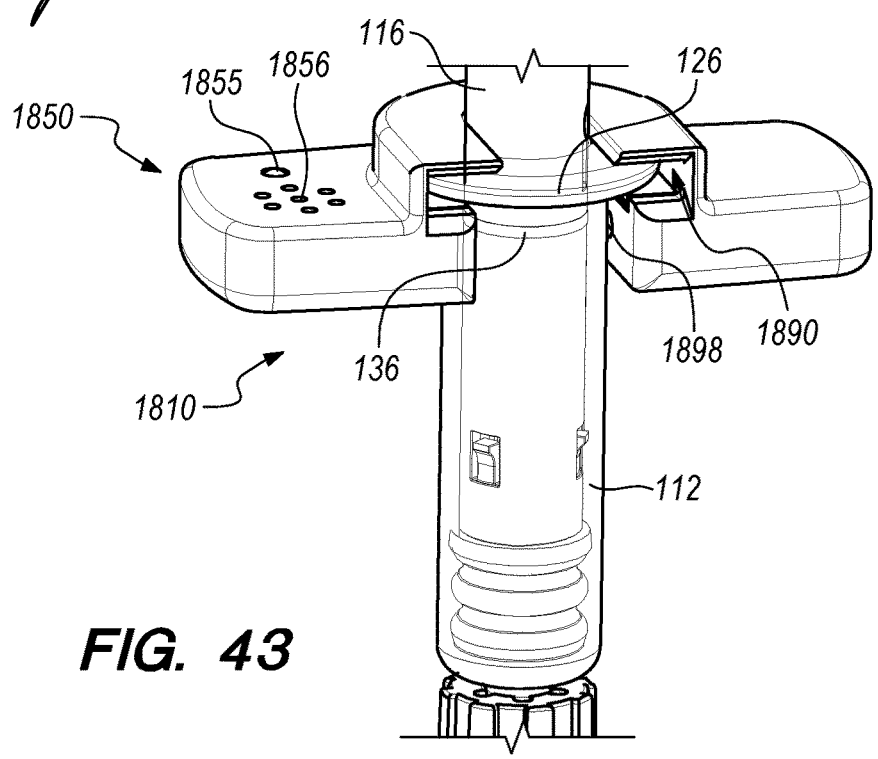

FIGS. 41-43 depict an injection system (1810) according to still another embodiment that also determines dose delivery completion using a distance traveled by the stopper member (114) and the plunger member (116) coupled thereto. The injection system (1810) includes a sensor flange (1850) having a light sensor (1898) similar to the sensors (160, 1798) depicted in FIGS. 8 and 38, and configured to read/detect a marker (136). The sensor flange (1850) also includes a slot (1890), (1855), and a speaker (1856), which are similar to the corresponding components depicted in FIG. 34 and described above.

Figure 38:
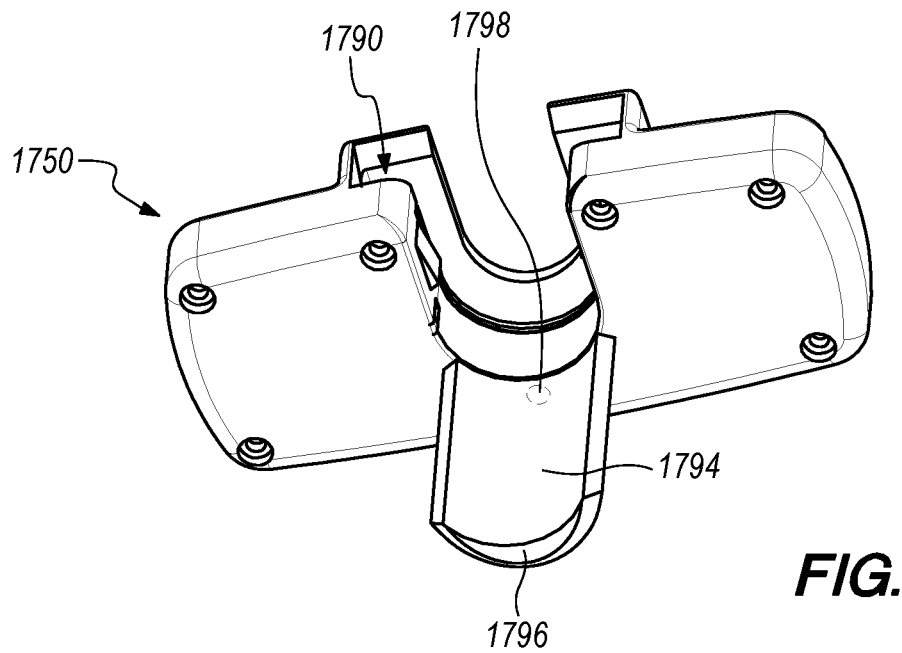

Like the light sensor (1798) depicted in FIG. 38, the light sensor (1898) includes a light emitter and a light receiver. As shown in FIG. 42, in the pre-injection configuration, the marker (136) on the plunger member (116) is positioned away from the light sensor (1898). In contrast, in the post-injection configurations shown in FIG. 43, the marker (136) is positioned in the light path of the light sensor (1898) allowing the light sensor (1898) to read the marker (136). Reading the marker (136) can include detecting a difference in reflected light (e.g., see FIGS. 37-40 described above) and/or optical character recognition. The marker (136) can be printed or molded on the plunger member (116), and may include injection information such as an identification of the injection system (1810) to allow tracking of medication delivery.

While the injection system (1810) depicted in FIGS. 41-43 includes a sensor flange (1850) with an optical sensor (1898), in other embodiments (not shown) the sensor can be a contact switch configured to be actuated by a rib or groove molded into a plunger member in order to send/detect dose delivery completion.

Figure 44:
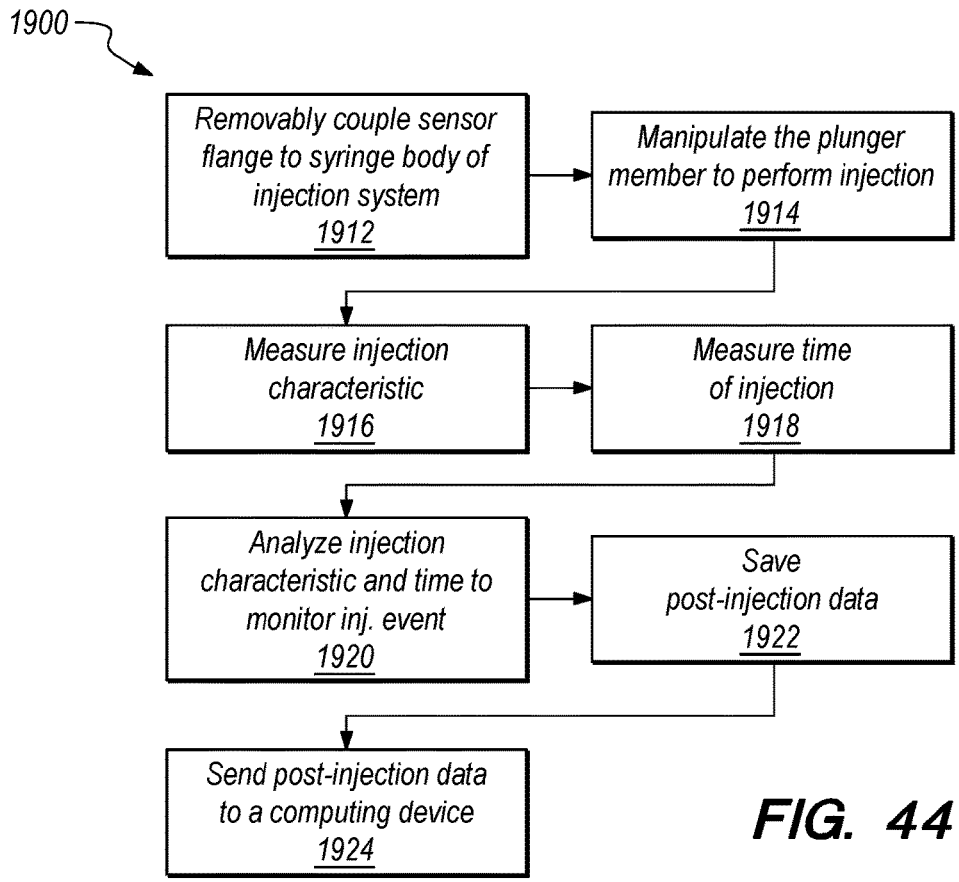

FIG. 44 depicts a method (1900) of collecting injection information according to still another embodiment. At step (1912), a sensor flange, such as the sensor flanges (150, 1150, 1650, 1750, 1850) described above, is removably coupled to the syringe body of an injection system. The injection system may be similar or identical to the injection systems (110, 1110, 1610, 1710, 1810) described above. The sensor flange may be secured to the syringe body using an interference fit.

At step (1914), the plunger member of the injection system is manipulated to perform the injection. For instance, force may be applied to a proximal end pad of the plunger member using a digit (e.g., a thumb) of a user's hand while one or more other digits of the user's hand provide an opposing force (e.g., against a distal side of the syringe flange or a sensor flange disposed thereon).

At step (1916), the sensor flange measures an injection characteristic using a sensor. The sensor may be any known type of sensor including, but not limited to, acoustic sensors, motion sensors, proximity sensors, temperature sensors, force sensors (including attenuated for sensors), accelerometer sensors, orientation sensors, optical sensors, roller sensors, sonic echo sensors, and light sensors. The type of sensor may be selected to measure the type of injection characteristic required by the method (1900).

At step (1918), the sensor flange measures a time of injection ("injection time"). The sensor flange may include an internal clock to measure the time of injection. The time of injection may include the temporal duration of the injection and/or the time at which the injection was begun and/or completed.

At step (1920), the sensor flange (i.e., a processor therein or coupled thereto) analyzes the injection characteristic and the injection time to monitor (e.g., detect, measure, determined, etc.) an injection event (e.g., completion of injection, plunger force, sheer force, injection error, etc.) The type of injection event monitored during the method (1900) determines the type of injection characteristic measured in the types of sensor in the sensor flange.

At step (1922), the sensor flange stores post-injection data in a memory of the sensor flange. Post-injection data includes, but is not limited to, the measured injection characteristic and injection time, data relating to the monitored injection event, F×t value (cumulative and instantaneous), injection date and time, injection frequency, plunger force, injection elapsed time, injection error related data, viscosity, temperature, warming time, shear force, residual drug remaining in the syringe, multiple injection site regimen data, reward program data, and educational/marketing data. Injection errors include, but are not limited to, drug identity error, injection timing error, dosage error, shear force error, de-bubbling error, residual drug remaining in the syringe, and multi-site injection error.

At step (1924), the sensor flange sends the post-injection data to a computing device. Sensor flange can communicatively couple to the computing device using various communication devices, which may be wired and/or wireless. Wireless communication devices include, but are not limited to, Bluetooth, WiFi, WiFi Direct, cellular, and near field communications. After the sensor flange establishes a communication link with a computing device, the sensor flange may download the post-injection data to the computing device. In one embodiment, the sensor flange stores measured, collected, calculated, and generated post-injection data in a memory then downloads the post-injection data in a batch/asynchronous manner to a computing device. The computing device receiving the post-injection data from the sensor flange can include but is not limited to a smartphone, a computer, a database, a cloud computing network. The computing device can be associated with a health care professional, a home injection patient, an electronic medical record, a smartphone application, a doctor, a nurse, a caregiver, a medical insurer, a clinical trial, a clinical trial administrator, a pharmaceutical distribution company, a pharmaceutical manufacturer, etc.

Smart Proximal End Pad/Thumbpad

Figure 45:
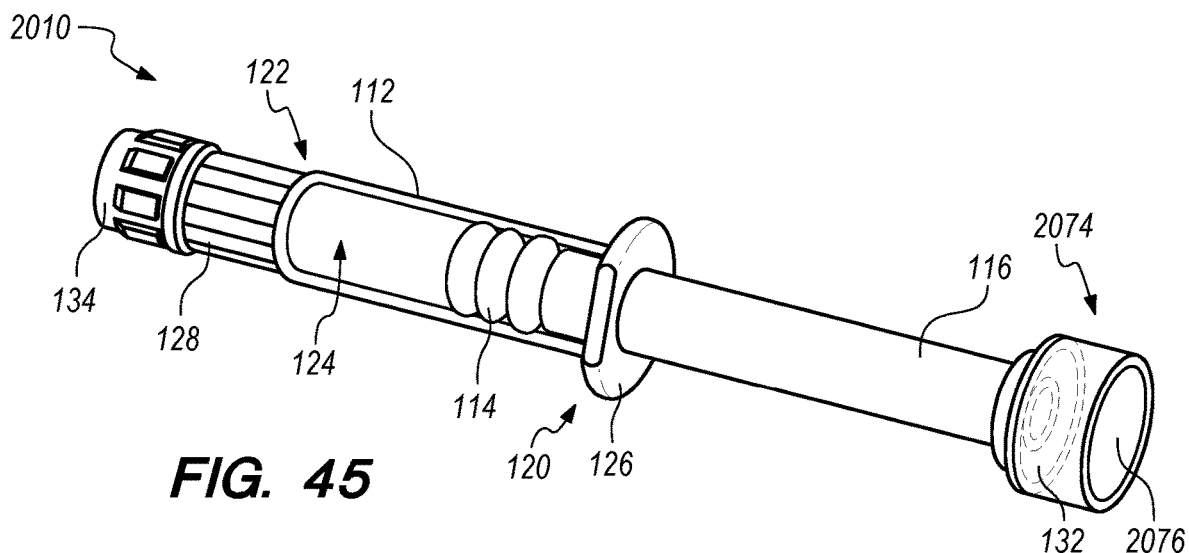
FIG. 45 illustrates a sensor proximal end pad removably coupled to an injection system according to one embodiment.

FIG. 45 depicts an injection system (2010) including a sensor proximal end pad ("thumbpad") (2074) to detect an injection characteristic and monitor an injection event, such as those described above. The injection system (2010) also includes a syringe body (112), a stopper member (114), and a plunger member (116). The syringe body (112) includes an open proximal end (120) and an open distal end (122). The syringe body (112) also includes a syringe interior (124), a syringe flange (126) at the proximal end (120) thereof, and a coupling member (128) at the distal end (122) thereof (e.g., for removably attaching a needle assembly or a second coupling member connected to an IV bag). The stopper member (114) is disposed in the syringe interior (124), and coupled to the plunger member (116), such that the plunger member (116) may be manipulated to insert the stopper member (114) distally into the syringe interior (124) to expel an injectable substance (e.g., a liquid medicine) from the syringe interior (124) through the coupling member (128). In the embodiment depicted in FIG. 45, the coupling member (128) is a female Luer connector capped with a Luer cap (134) but configured to form a fluid tight connection/seal with a male Luer connector (not shown). The plunger member (116) includes a proximal end pad (132) to facilitate manual manipulation of the plunger member (116) using a digit (e.g., a thumb) of a user's hand while one or more other digits of the user's hand provide an opposing force (e.g., against a distal side of the syringe flange (126) or a body disposed thereon).

The sensor thumbpad (2074) is removably coupled to the proximal end pad (132) of the plunger member (116). The sensor thumbpad (2074) includes a force sensor (2076) configured to measure an injection force applied to the sensor thumbpad (2074) during an injection using the injection system (2010). The sensor thumbpad (2074) may also include a processor and/or a communication device (neither shown) for monitoring an injection event (e.g., complete injection of a dose) as described above. The sensor thumbpad (2074) may also include other features described above for the sensor flange, including but not limited to, a display, a speaker, a mounting sensor, etc. The sensor thumbpad (2074) may include alternative and/or additional sensors such acoustic sensors, motion sensors, proximity sensors, temperature sensors, attenuated force sensors, accelerometer sensors, orientation sensors, optical sensors, sonic echo sensors, and light sensors.

Smart Plunger Rod

Figure 18A:
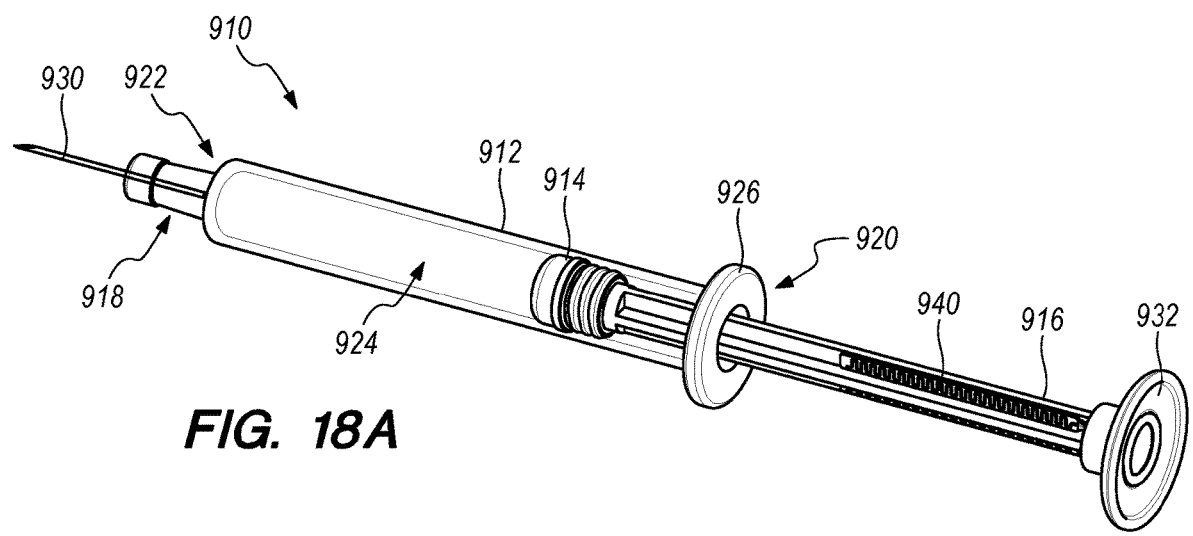
FIGS. 18A and 18B illustrate an injection system having an RFID tag according to one embodiment.
Figure 18B:
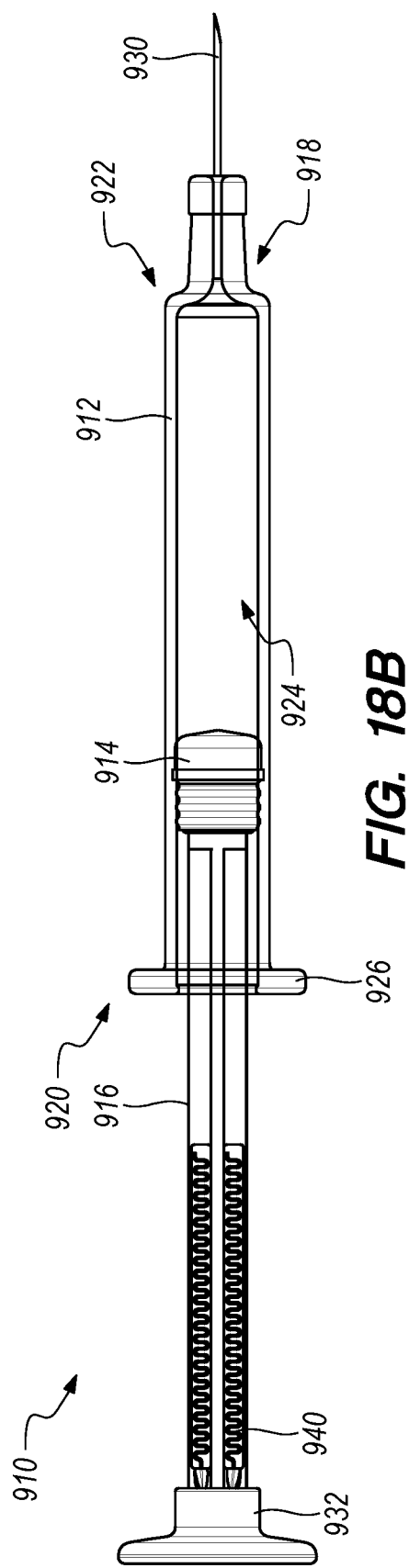

FIGS. 18A and 18B depict it injection system (910) having a one-way mode of communication with a computing device. The injection system (910) includes a syringe body (912), a stopper member (914), a plunger member (916), and a needle assembly (918). The syringe body (912) includes an open proximal end (920) and an open distal end (922). The syringe body (912) also includes a syringe interior (924), and a syringe flange (926) at the proximal end (920) thereof. The stopper member (914) is disposed in the syringe interior (924), and coupled to the plunger member (916), such that the plunger member (916) may be manipulated to insert the stopper member (914) distally into the syringe interior (924) to expel an injectable substance (e.g., fluid) from the syringe interior (924) through the needle assembly (918). The needle assembly (918) is a staked configuration at the distal end (922) of the syringe body (912). Alternatively, a user attachable Luer needle may be used. The needle assembly (918) includes a needle (930) at a distal end thereof. The plunger member (916) includes a proximal end pad (932) to facilitate manual manipulation of the plunger member (916) using a digit (e.g., a thumb) of a user's hand while one or more other digits of the user's hand provide an opposing force (e.g., against a distal side of the syringe flange (926) or a body disposed thereon).

The plunger member (916) also includes an RFID chip (938) (see FIGS. 21 and 22) and a pair of antennae (940). Before injection, the RFID chip (938) is inactivated, but during injection the RFID chip (938) is activated to send post-injection information to an RFID receiver (see FIGS. 27-28B). This post-injection information can include, but is not limited to, information identifying the injection system (910) and indicating that injection using the injection system (910) has been completed. Alternatively, the RFID chip (938) may communicate bi-directionally with the computing device. During an injection, the computing device may scan for the presence of an activated RFID chip to identify an injection completed event. The RFID chip (938) may then be instructed by the computing device to inactivate/self-destruct, thereby preventing the RFIP chip (938) from being inadvertently read a second time by a computing device.

Figure 19:
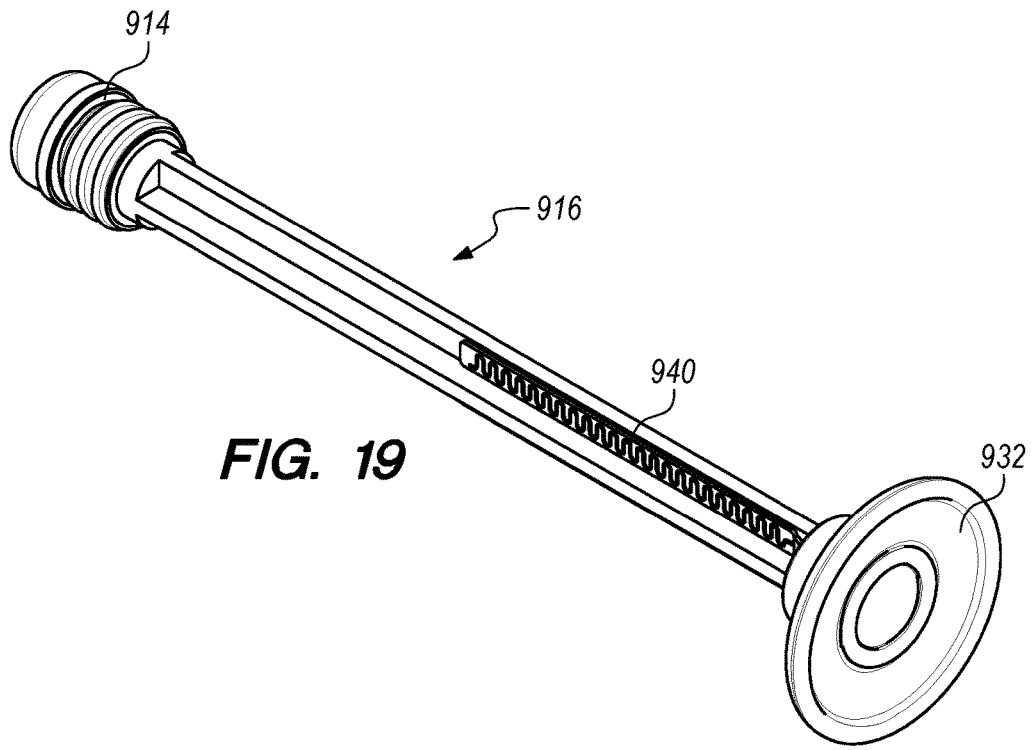
FIGS. 19 and 20 illustrate a plunger rod for an injection system having an RFID tag according to one embodiment.
Figure 20:
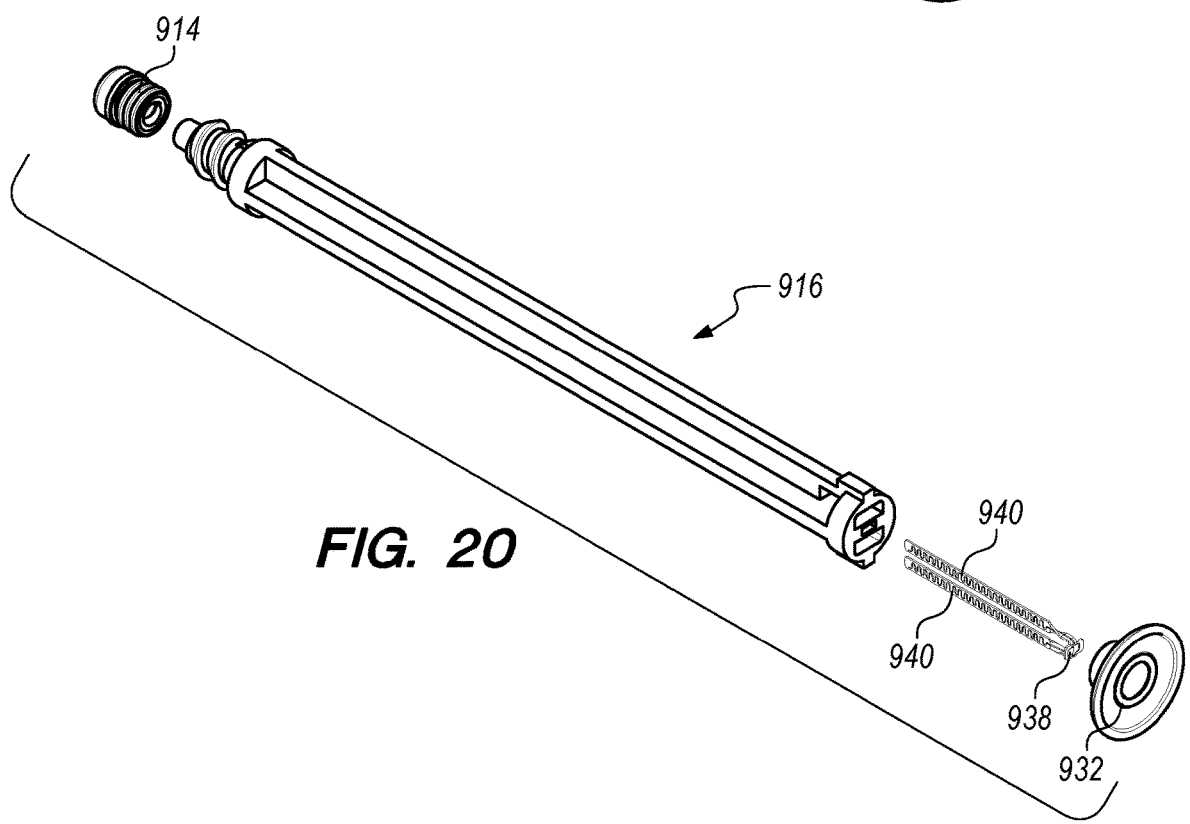

FIGS. 19 and 20 depicts the plunger member (916) of the injection system (910) depicted in FIGS. 18A and 18B. FIG. 19 shows that the antennae (940) are disposed inside of the plunger member (916). FIG. 20 shows that the antennae (940) are physically and operatively coupled to an RFID chip (938), which is disposed in the proximal end of the plunger member (916) and covered by the proximal and pad (932).

Figure 21:
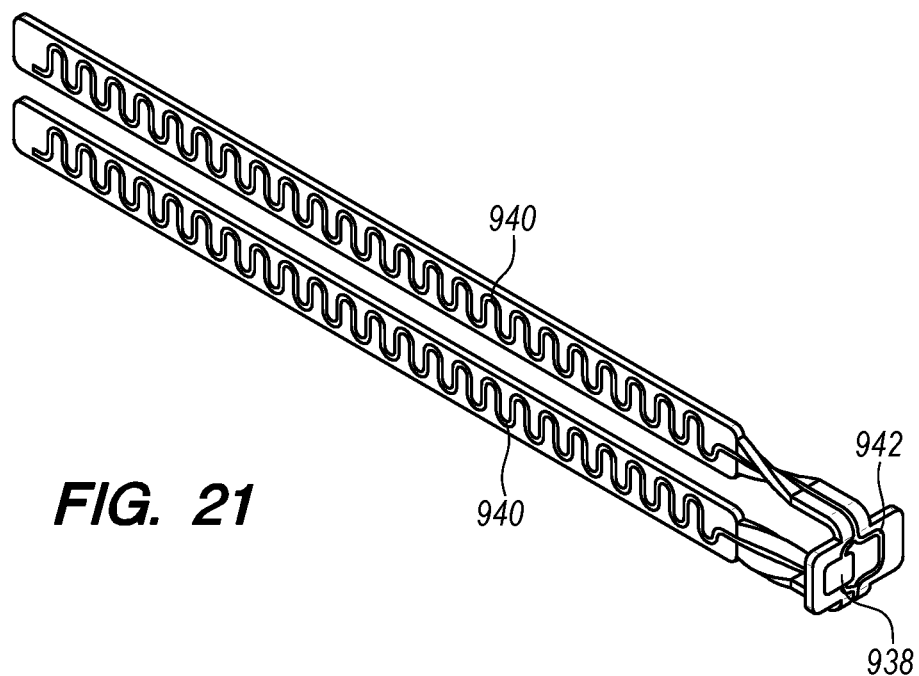
FIGS. 21 and 24 illustrate an RFID tag and two antennae for use with an injection system according to one embodiment in respective inactivated and activated states.

FIG. 21 depicts an RFID chip (938) and antennae (940) combination according to one embodiment that is usable with the injection systems depicted in FIGS. 18A to 20. The antennae (940) are electrically and operatively coupled to the RFID chip (938). The RFID chip (938) includes a shunt (942) to divert power from the RFID chip (938) because of electricity's tendency to flow through the path of least resistance. Diverting power from the RFID chip (938) inactivates the chip.

Figure 22:
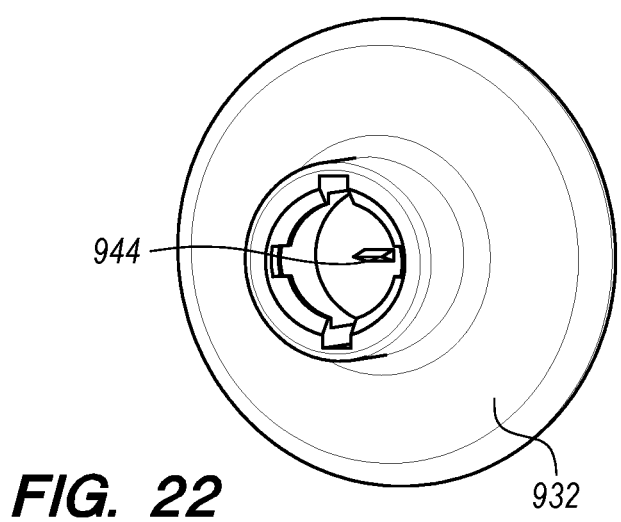
FIG. 22 illustrate a proximal end cap of a plunger rod for an injection system having an RFID tag according to one embodiment.

FIG. 22 depicts the inside of the proximal end cap (932) of the plunger member (916) for use with the RFID chip (938) and antennae (940) combination depicted in FIG. 21. The proximal end cap (932) includes a cutting member (944) configured to sever the shunt (942) when a force is applied to the proximal end (932) to move the plunger member (916) in a distal direction. Severing the shunt (942) activates the RFID chip (938) by directing power to the chip. An activated RFID chip (938) can send data to an RFID receiver as described above.

Figure 23A:
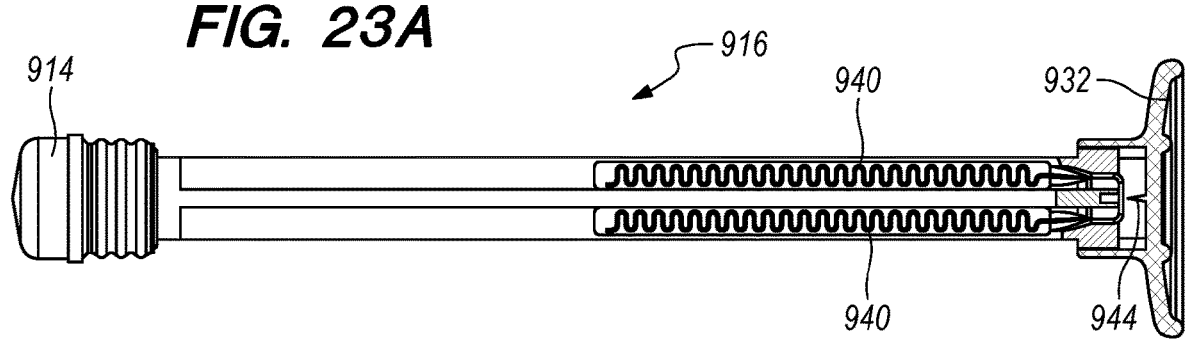
FIGS. 23A and 23B a plunger rod for an injection system having an RFID tag according to one embodiment in respective inactivated and activated states.
Figure 23B:
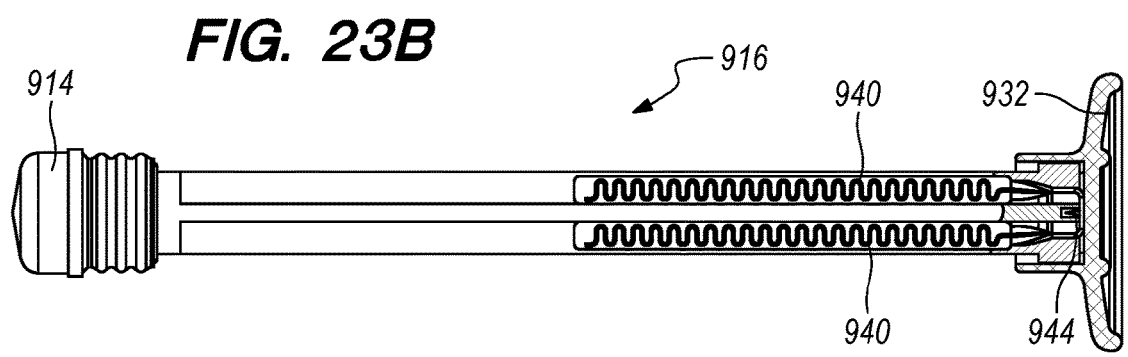
Figure 24:
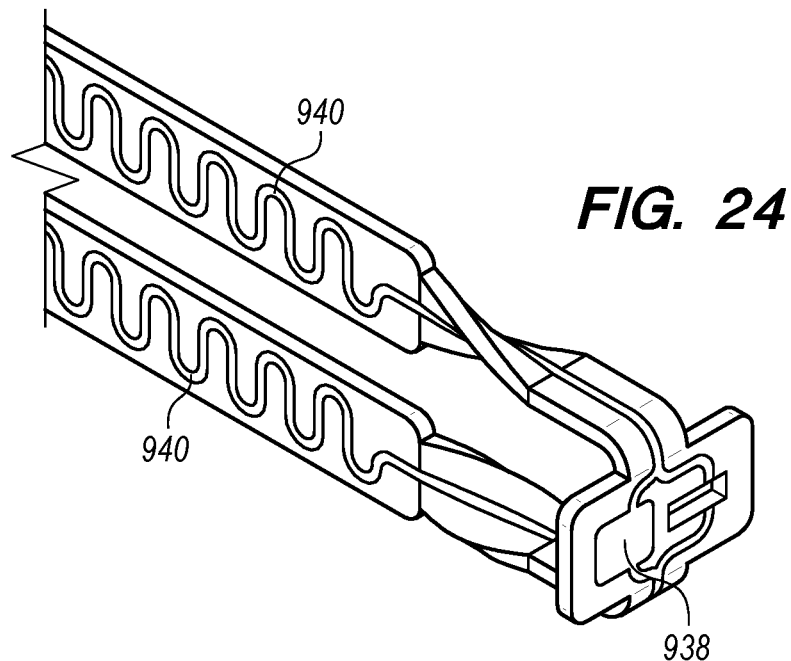

FIGS. 23A and 23B shows that the proximal end cap (932) of the plunger member (916) depicted in FIG. 22 is movable along a longitudinal axis of the plunger member (916). FIG. 23A depicts the pre-injection position of the proximal end cap (932) in which the cutting member (944) does not contact the shunt (942) in the RFID chip (938). FIG. 23B depicts the post-injection position of the proximal end cap (932) in which the cutting member (944) has severed the shunt (942), thereby activating the RFID chip (938). FIG. 24 depicts the activated RFID chip (938) with the shunt (942) severed.

Figure 25:
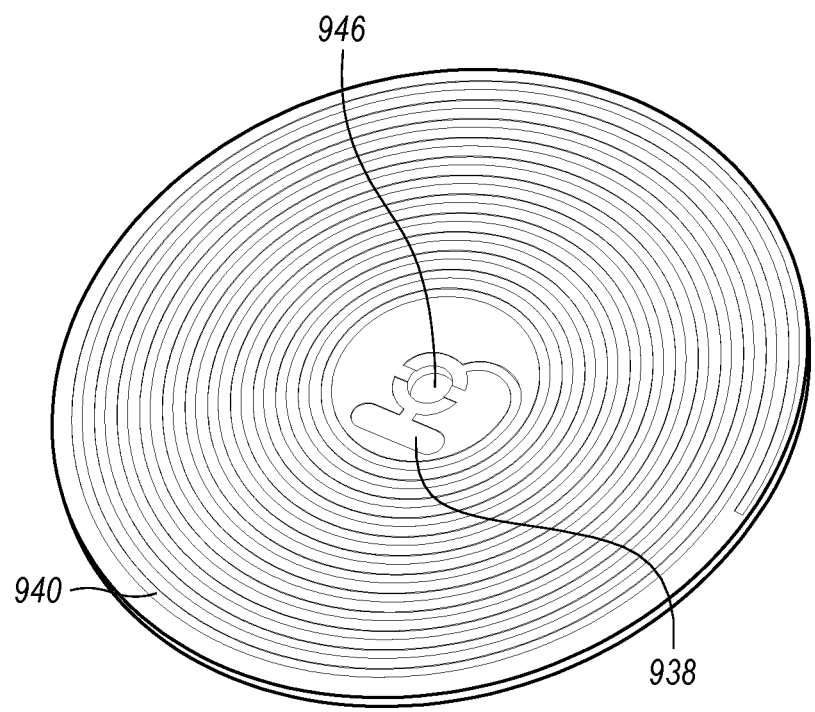
FIG. 25 illustrates an RFID tag and a spiral antenna for use with an injection system according to one embodiment.

FIG. 25 depicts an RFID chip (938) and its corresponding spiral antenna (940). This RFID chip (938) and spiral antenna (940) combination is configured to be disposed in the proximal and (932) of the plunger member (916) for use with the injection systems depicted in FIGS. 18A to 20. The RFID chip (938) includes a gap (946) that prevents power from being provided to the RFID chip (938) until the (946) is bridged to complete the circuit.

Figure 26:
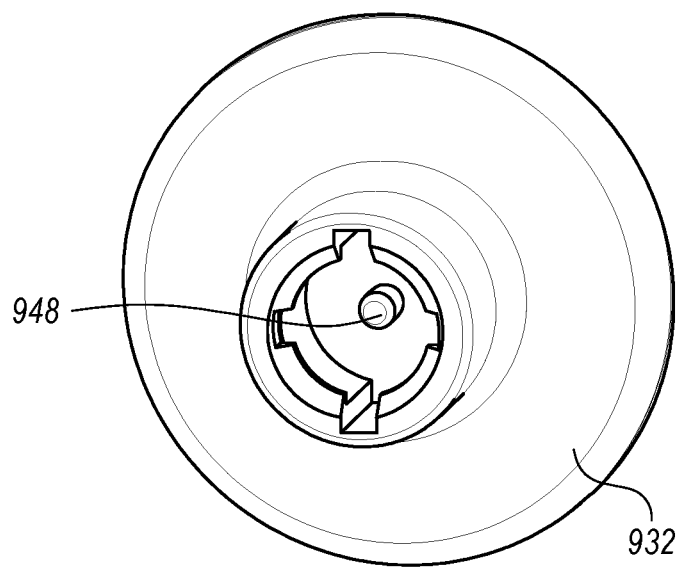
FIG. 26 illustrate a proximal end cap of a plunger rod for an injection system having an RFID tag according to one embodiment.

FIG. 26 depicts the inside of the proximal end cap (932) of the plunger member (916) for use with the RFID chip (938) and spiral antenna (940) combination depicted in FIG. 25. The proximal end cap (932) includes a conducting member (948) configured to bridge the gap (946) when a force is applied to the proximal end (932) to move the plunger member (916) in a distal direction. Bridging the gap (946) activates the RFID chip (938) by providing power to the chip. An activated RFID chip (938) can send data to an RFID receiver as described above. The proximal end cap (932) of the plunger member (916) depicted in FIG. 26 is movable along a longitudinal axis of the plunger member (916) as shown in FIGS. 23A and 23B.

Figure 27:
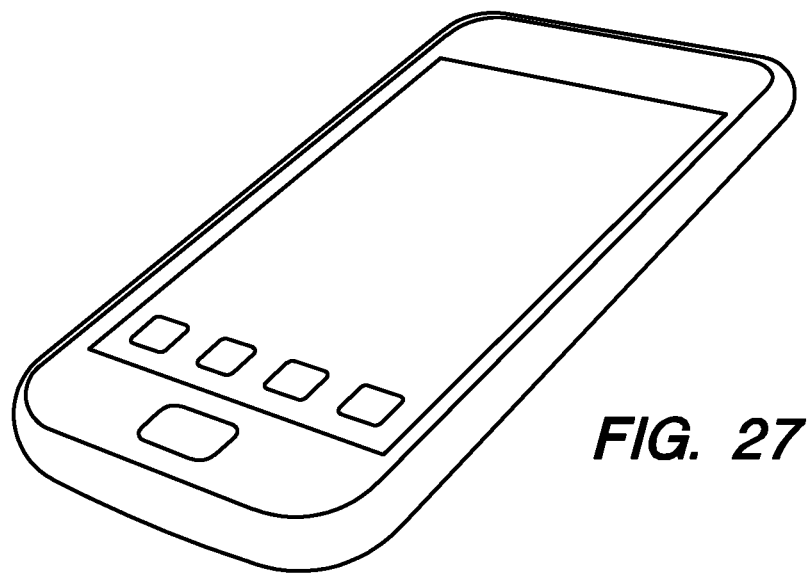
FIG. 27 illustrates a smartphone having an RFID receiver according to one embodiment.
Figure 28A:
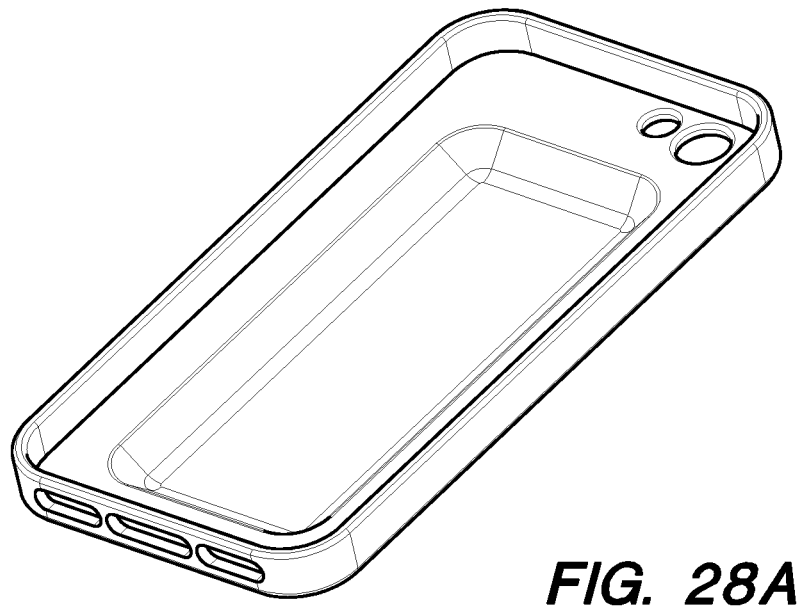
FIGS. 28A and 28B illustrate a phone case having an RFID receiver according to one embodiment.
Figure 28B:
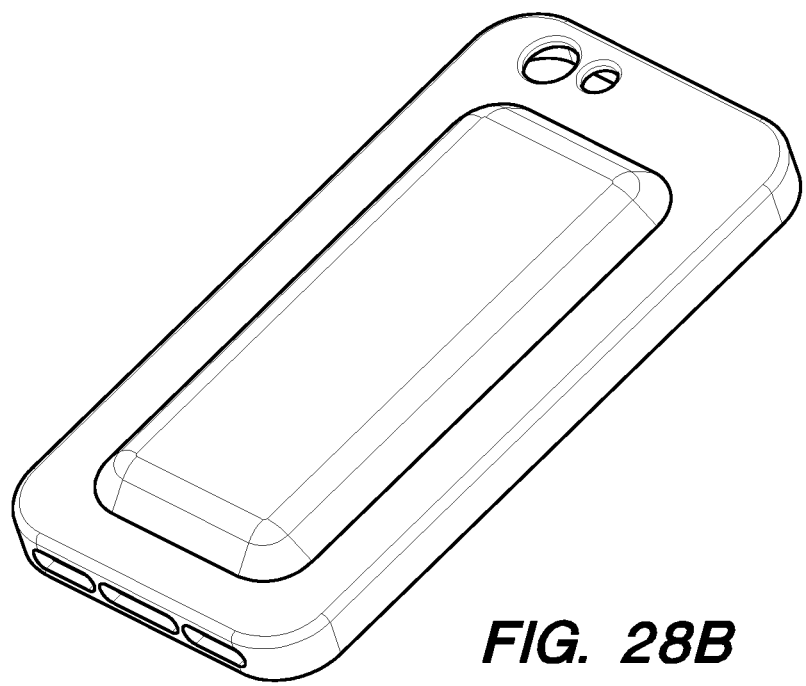

FIG. 27 shows a smart phone that may include an RFID receiver functionality and application. FIGS. 28A and 28B illustrate a phone cover that includes an RFID receiver configured to operatively coupled to a smart phone in the phone cover.

Figure 29:
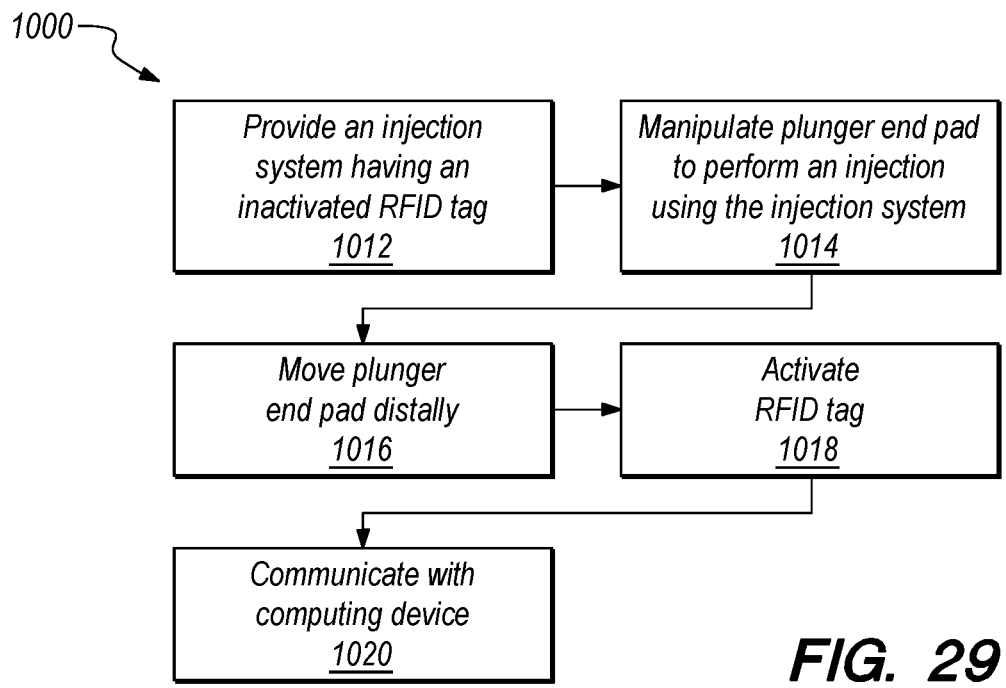
FIG. 29 illustrates a method of sending injection information using an RFID chip according to one embodiment.

FIG. 29 depicts a method (1000) of sending injection information using an RFID chip according to one embodiment. At step (1012), an injection system like the one depicted in FIGS. 18A to 28B is provided. The injection system includes an inactivated RFID chip.

At step (1014), the plunger member of the injection system is manipulated to perform the injection. For instance, force may be applied to a proximal end pad of the plunger member using a digit (e.g., a thumb) of a user's hand while one or more other digits of the user's hand provide an opposing force (e.g., against a distal side of the syringe flange or a sensor flange disposed thereon).

At step (1016), the proximal end pad is moved distally relative to the plunger member. As shown in FIGS. 23A and 23B, applying a distally directed force to the proximal end pad may move the proximal end pad distally.

At step (1018), the RFID tag is activated. In the embodiment depicted in FIGS. 18A to 24, the RFID tag is activated by severing a shunt. In the embodiment depicted in FIGS. 25 and 26, the RFID tag is activated by bridging a gap. However, other methods of activating a previously inactivated RFID tag are also included in step (1018).

At step (1020), the activated RFID tag communicates with an RFID receiver to communicate post-injection information to the RFID receiver and the computing device operatively coupled thereto. This post-injection information can include, but is not limited to, information identifying the injection system (910) and indicating that injection using the injection system (910) has been completed. The post-injection information can be used to track patient compliance, drive reward programs, inform insurance programs, etc.

While the various systems and methods described herein depict injection systems having manually actuated plunger members, the injection data collection systems and methods described herein work equally well with automated or semi-automated injection systems such as injection pens.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject injection information collection procedures may be provided in packaged combination for use in executing such interventions. These supply "kits" may further include instructions for use and/or may be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A method of measuring injection of a liquid medicine, comprising:

a sensor in a sensor flange removably coupled to a syringe body measuring an injection characteristic during an injection of a liquid medicine from the syringe body;

a processor in the sensor flange analyzing the injection characteristic to determine an occurrence of an injection event;

a mounting sensor in the sensor flange detecting when the sensor flange is removably coupled to the syringe body;

the sensor flange delivering an alarm once the injection of the liquid medicine has been completed to prevent the sensor flange from being disposed of prematurely; and the processor silencing the alarm once the mounting sensor detects the finger flange has been removed from the syringe body.

2. The method of claim 1, wherein the injection event is an injection of a dose of the liquid medicine.

3. The method of claim 2, wherein the sensor is a force sensor and the injection characteristic is a force applied to a plunger member disposed at least partially in the syringe body.

4. The method of claim 3, further comprising the processor calculating a product of the force and a time of the injection of the dose of the liquid medicine.

5. The method of claim 4, further comprising the processor comparing a measured force time product to a reference force time product to determine the occurrence of the injection event.

6. The method of claim 5, wherein the reference force time product is pre-determined based on a viscosity of the liquid medicine to be injected and a size of the needle.

7. The method of claim 5, further comprising the sensor flange recording a time and a date of the occurrence of the injection event.

8. The method of claim 2, wherein the sensor is an optical sensor and the injection characteristic is a position, a velocity, or an acceleration of a plunger member disposed at least partially in the syringe body.

9. The method of claim 8, wherein the optical sensor is an IR sensor.

10. The method of claim 8, the plunger member comprising a visual feature to be read by the optical sensor.

11. The method of claim 2, wherein the sensor is an acoustic sensor and the injection characteristic is a position, a velocity, or an acceleration of a plunger member disposed at least partially in the syringe body.

12. The method of claim 11, wherein the acoustic sensor is an acoustic reflection sensor configured to measure a distance from the sensor to a proximal end pad on the plunger member.

13. The method of claim 11, wherein the acoustic sensor is an acoustic reflection sensor configured to measure a distance from the sensor to a stopper member disposed in the syringe body and coupled to the plunger member.

14. The method of claim 2, wherein the sensor is a mechanical sensor and the injection characteristic is a position, a velocity, or an acceleration of a plunger member disposed at least partially in the syringe body.

15. The method of claim 14, wherein the mechanical sensor comprises a roller in contact with an outer surface of the plunger member, the method further comprising a reader in the mechanical sensor measuring a rotation of the roller.

16. The method of claim 15, wherein the reader is an optical sensor or a mechanical sensor.

17. The method of claim 1, wherein the sensor is a first sensor and the injection characteristic is a first injection characteristic, the sensor flange further comprising a second sensor to measure a second injection characteristic.

18. The method of claim 1, further comprising manipulating the sensor flange to insert a plunger member and a stopper member coupled thereto distally in a syringe interior relative to the syringe body.

19. The method of claim 18, the plunger member comprising a proximal end pad to be manipulated simultaneously with the sensor flange to insert the stopper member distally in the syringe interior relative to the syringe body.

20. The method of claim 1, wherein the mounting sensor comprises a mechanical switch.

* * * * *